United States Patent
Nilsson et al.

(10) Patent No.: US 11,434,237 B2
(45) Date of Patent: Sep. 6, 2022

(54) SELECTIVE LIGANDS FOR TAU AGGREGATES

(71) Applicant: KARIN & STEN MORTSTEDT CBD SOLUTIONS AB, Stockholm (SE)

(72) Inventors: Peter Nilsson, Stockholm (SE); Hamid Shirani, Stockholm (SE)

(73) Assignee: KARIN & STEN MORTSTEDT CBD SOLUTIONS AB, Stockholm (SE)

( * ) Notice: Subject to any disclaimer, the term of this patent is extended or adjusted under 35 U.S.C. 154(b) by 52 days.

(21) Appl. No.: 16/636,219

(22) PCT Filed: Aug. 3, 2018

(86) PCT No.: PCT/EP2018/071148
§ 371 (c)(1),
(2) Date: Feb. 3, 2020

(87) PCT Pub. No.: WO2019/025595
PCT Pub. Date: Feb. 7, 2019

(65) Prior Publication Data
US 2020/0369659 A1   Nov. 26, 2020

(30) Foreign Application Priority Data
Aug. 4, 2017 (GB) .................................. 1712567

(51) Int. Cl.
C07D 421/14 (2006.01)
C07D 417/14 (2006.01)
A61K 45/06 (2006.01)

(52) U.S. Cl.
CPC ......... *C07D 421/14* (2013.01); *C07D 417/14* (2013.01); *A61K 45/06* (2013.01)

(58) Field of Classification Search
CPC ... C07D 413/14; C07D 417/14; C07D 421/14
See application file for complete search history.

(56) References Cited

U.S. PATENT DOCUMENTS 7,067,507 B2 * 6/2006 Pulley ..................... A61P 43/00
514/183

FOREIGN PATENT DOCUMENTS

| EP | 1655287 A1 | 5/2006 |
| EP | 2103611 A1 | 9/2009 |
| EP | 2767532 A1 | 8/2014 |
| RO | 77770 A2 | 12/1981 |
| WO | WO 2005/095386 A1 | 10/2005 |
| WO | WO 2017/009454 A1 | 1/2017 |

OTHER PUBLICATIONS

Kornilov. STN record of Zhurnal Organicheskoi Khimii, 1973, 9(12), 2577-82 (Year: 1973).*

Panea. STN record of R077770, published Dec. 25, 1981 (Year: 1981).*
Arendt et al., "Tau and tauopathies," *Brain Research Bulletin*, 2016, 126, pp. 238-292.
Åslund et al., "Novel Pentameric Thiophene Derivatives for in Vitro and in Vivo Optical Imaging of a Plethora of Protein Aggregates in Cerebral Amyloidoses," *ACS Chemical Biology*, 2009, vol. 4, No. 8, pp. 673-684.
Bäck et al., "Anionic Oligothiophenes Compete for Binding of X-34 but not PIB to Recombinant Aβ Amyloid Fibrils and Alzheimer's Disease Brain-Derived Aβ," *Chemistry A European Journal*, Dec. 2016, vol. 22, Issue 51, pp. 18335-18338.
Ballatore et al., "Tau-mediated neurodegeneration in Alzheimer's disease and related disorders," *Nature Reviews: Neuroscience*, Sep. 2007, vol. 8, pp. 663-672.
Chemical Abstracts Service STN accession No. 1980:110128, 1 page.
Clavaguera et al., "Brain homogenates from human tauopathies induce tau inclusions in mouse brain," *Proceedings of the National Academy of Sciences*, Jun. 2013, vol. 110, No. 23, pp. 9535-9540.
Fodero-Tavoletti et al., "$^{18}$F-THK523: a novel in vivo tau imaging ligand for Alzheimer's disease," *Brain*, 2011, 134, pp. 1089-1100.
Ganushchak et al., "5-Aryl-2-furaldehydes in the Synthesis of 2-Substituted 1,3-Benzazoles," *Russian Journal of Organic Chemistry*, vol. 39, No. 9, 2003, pp. 1295-1300.
Herrmann et al., "Structure-based drug design identifies polythiophenes as antiprion compounds," *Science Translational Medicine*, vol. 7, Issue 299, Aug. 5, 2015, 299ra123, pp. 1-17.
International Search Report and Written Opinion, PCT Patent Application No. PCT/EP2018/071148, dated Oct. 16, 2018, 14 pages.
Klingstedt et al., "Distinct Spacing Between Anionic Groups: An Essential Chemical Determinant for Achieving Thiophene-Based Ligands to Distinguish b-Amyloid or Tau Polymorphic Aggregates," *Chemistry—A European Journal*, Jun. 2015, vol. 21, Issue 25, pp. 9072-9082.
Klingstedt et al., "Synthesis of a library of oligothiophenesand their utilization as fluorescent Tigands for spectral assignment of protein aggregates," *Organic & Biomolecular Chemistry*, Sep. 2011, vol. 9, Issue 24, pp. 8356-8370.

(Continued)

*Primary Examiner* — Noble E Jarrell
(74) *Attorney, Agent, or Firm* — Fenwick & West LLP

(57) ABSTRACT

The invention provides compounds of formula (I) and compositions comprising compounds of formula (I). The invention further provides uses of the compounds of formula (I) and compositions comprising compounds of formula (I), including the use of such compounds for the detection of tau deposits, and the use of such compounds and compositions as diagnostic agents in the diagnosis or monitoring of the progression of a disease or disorder such as Alzheimer's disease or corticobasal degeneration, or for the prevention or treatment of a disease or disorder such as Alzheimer's disease or corticobasal degeneration.

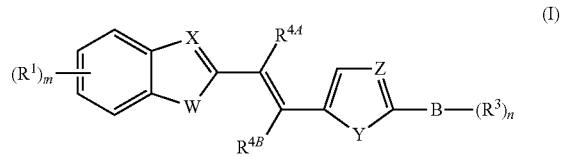

12 Claims, 7 Drawing Sheets

(56) References Cited

OTHER PUBLICATIONS

Klingstedt et al., "The Structural Basis for Optimal Performance of Oligothiophene-Based Fluorescent Amyloid Ligands: Conformational Flexibility is Essential for Spectral Assignment of a Diversity of Protein Aggregates," *Chemistry—A European Journal*, Jul. 2013, vol. 19, Issue 31, pp. 10179-1019.

Klunk et al., "Imaging Brain Amyloid in Alzheimer's Disease with Pittsburgh Compound-B," Annals of Neurology, Mar. 2004, vol. 55, Issue 3, pp. 306-319.

Kudo et al., "2-(2-[2-Dimethylaminothiazol-5-yl]Ethenyl)-6-(2-[Fluoro]Ethoxy)Benzoxazole: A Novel PET Agent for In Vivo Detection of Dense Amyloid Plaques in Alzheimer's Disease Patients," *The Journal of Nuclear Medicine*, Apr. 2007, vol. 48, No. 4, pp. 553-561.

Levine and Walker, "Molecular polymorphism of Aβ in Alzheimer's disease," *Neurobiology of Aging*, Apr. 2010, vol. 31, Issue 4, pp. 542-548.

Lu et al., "Molecular Structure of β-Amyloid Fibrils in Alzheimer's Disease Brain Tissue," *Cell*, vol. 154, Issue 6, Sep. 12, 2013, pp. 1257-1268.

Maarouf et al., "Histopathological and molecular heterogeneity among individuals with dementia associated with Presenilin mutations," *Molecular Neurodegeneration*, 2008, vol. 3, No. 20, 18 pages.

Maruyama et al., "Imaging of Tau Pathology in a Tauopathy Mouse Model and in Alzheimer Patients Compared to Normal Controls," *Neuron*, vol. 79, Issue 6, Sep. 18, 2013, pp. 1094-1108.

Mullard, A., "Pharma pumps up anti-tau Alzheimer pipeline despite first Phase III failure," *Nature Reviews: Drug Discovery*, vol. 15, Sep. 2016, pp. 591-592.

Nilsson, "Small organic probes as amyloid specific ligands—Past and recent molecular scaffolds," *FEBS Letters: Protein Folding, Misfolding and Disease*, Aug. 20, 2009, vol. 583, Issue 16, pp. 2593-2599.

Puterova et al., "Reactions of Substituted Furan-2-carboxaldehydes and Furo[b]pyrole Type Aldehydes with Benzothiazolium Salts," *Molecules*, vol. 9, No. 4, 2004, pp. 241-255.

Qiang et al., "Structural variation in amyloid- fibrils from Alzheimer's disease clinical subtypes," *Nature*, Jan. 2017, 541, pp. 217-221.

Quist et al., "Push-pull chromophores comprising benzothiazolium acceptor and thiophene auxiliary donor moieties: Synthesis, structure, linear and quadratic non-linear optical properties," *Dyes and Pigments*, vol. 81, No. 3, 2009, pp. 203-210.

Ross and Poirier, "Protein aggregation and neurodegenerative disease," *Nature Medicine*, Jul. 2004, 10, pp. S10-S17.

Shirani et al., "A Palette of Fluorescent Thiophene-Based Ligands for the Identification of Protein Aggregates," *Chemistry—A European Journal*, Oct. 2015, vol. 21, Issue 43, pp. 15133-15137.

Shirani et al., "Synthesis of Thiophene-Based Optical Ligands That Selectively Detect Tau Pathology in Alzheimer's Disease," *Chemistry—A European Journal*, Dec. 2017, vol. 23, Issue 67, pp. 17127-17135.

Small et al., "PET of Brain Amyloid and Tau in Mild Cognitive Impairment," *The New England Journal of Medicine*, Dec. 21, 2006, 355:25, pp. 2652-2663.

Taghavi et al., "N'-Benzylidene-Benzohydrazides as Novel and Selective Tau-PHF Ligands," *Journal of Alzheimer's Disease*, Dec. 12, 2011, vol. 27, No. 4, pp. 835-843.

Tralić-Kulenović et al., "Synthesis and absorption spectral properties of substituted phenylfurylbenzothiazoles and their vinylogues," *Monatshefte für Chemie / Chemical Monthly*, vol. 125, No. 2, 1994, pp. 209-215.

Xia et al., "[$^{18}$F]T807, a novel tau positron emission tomography imaging agent for Alzheimer's disease," *Alzheimer's & Dementia*, vol. 9, Issue 6, Nov. 2013, pp. 666-676.

Yang et al., "Brain Amyloid Imaging—FDA Approval of Florbetapir F18 Injection," *The New England Journal of Medicine*, Sep. 6, 2012, 367:10, pp. 885-887.

Zhang et al., "A Highly Selective and Specific PET Tracer for Imaging of Tau Pathologies," *Journal of Alzheimer's Disease*, Aug. 22, 2012, vol. 31, No. 3, pp. 601-612.

\* cited by examiner

Figure 5
| Example compound | Exc. Max. DMSO (nm) | Exc. Max. PBS (nm) | Exc. Max. NFT (nm) | Em. Max. DMSO (nm) | Em. Max. PBS (nm) | Em. Max. NFT (nm) | Stokes' shift DMSO (nm) | Stokes' shift PBS (nm) | Stokes' shift NFT (nm) |
|---|---|---|---|---|---|---|---|---|---|
| 8a | 418 | 345 | 536 | 501 | 581 | 617 | 83 | 236 | 81 |
| 3a | 458 | 457 | 526 | 594 | 575 | 599 | 136 | 118 | 73 |
| 3b | 482 | 465 | 549 | 633 | 619 | 626 | 151 | 154 | 77 |
| 3c | 482 | 458 | 535 | 610 | 595 | 608 | 128 | 137 | 73 |
| 3d | 482 | 464 | 549 | 627 | 609 | 626 | 145 | 145 | 77 |
Figure 6
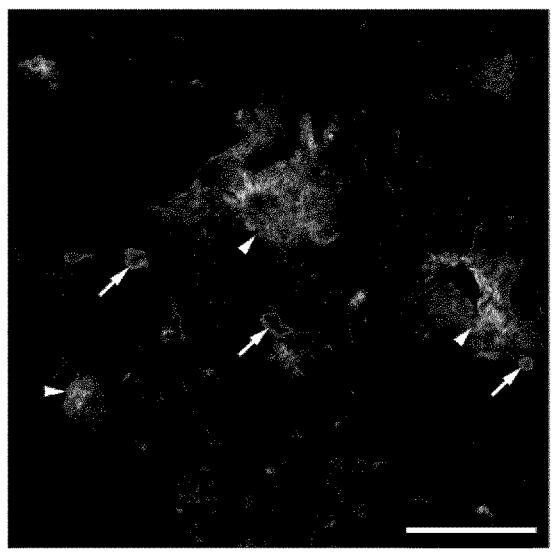 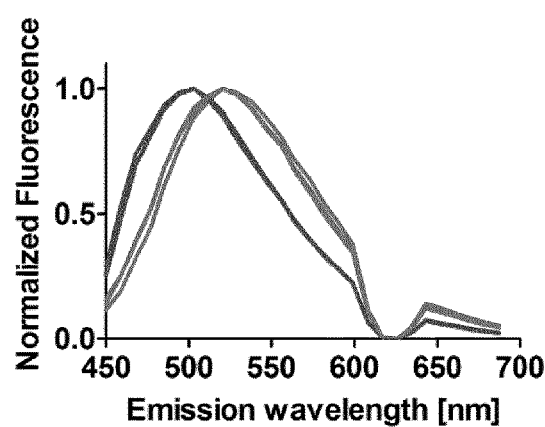
A                                    B

SELECTIVE LIGANDS FOR TAU AGGREGATES

CROSS-REFERENCE TO RELATED APPLICATIONS

This application is the National Stage of International Application No. PCT/EP2018/071148, filed Aug. 3, 2018, which claims the benefit of United Kingdom Application No. 1712567.5, filed Aug. 4, 2017, each of which is herein incorporated by reference in its entirety.

FIELD OF THE INVENTION

The present invention relates to compounds of formula (I) and compositions comprising compounds of formula (I). The compounds of the present invention are useful in the detection, diagnosis and treatment of neurodegenerative diseases, and especially tauopathies such as Alzheimer's disease.

INTRODUCTION

Alzheimer's disease is a neurodegenerative disorder causing symptoms including memory loss, difficulties with thinking, problem-solving, speech and/or language, personality changes, hallucinations, delusions, low mood and anxiety. It is the most common cause of dementia. Alzheimer's is a progressive disease and over time more symptoms develop, and the symptoms become more severe.

Protein deposits are the pathological hallmarks of a wide range of neurodegenerative diseases (C. A. Ross, M. A. Poirier, *Nat. Med.* 2004, 10, 10-17), including Alzheimer's disease and corticobasal degeneration. Small hydrophobic ligands that are selective for protein aggregates having an extensive cross β-pleated sheet conformation and sufficient structural regularity have been developed. The most common ligands are derivatives of Congo Red or thioflavins and a variety of other molecular scaffolds have also been reported (K. P. R. Nilsson, *FEBS Lett.* 2009, 583, 2593-2599). However, most of these ligands can only generally detect disease-associated protein aggregates, and they are not able to detect specific disease-associated protein aggregates consisting of a distinct protein.

The microtubule associated protein tau is one protein deposit shown to cause neurodegeneration. Tau can form intracellular fibrillary deposits in neurons and glial cells, and these tau deposits are linked to a large variety of disorders, collectively referred to as tauopathies. Tauopathies include more than 20 disorders including Alzheimer's disease, progressive supranuclear palsy, corticobasal degeneration, and Pick's disease. Although dysfunction of tau has unequivocally been shown to be able to cause neurodegeneration, the precise mechanisms of how tau is involved in neurodegenerative disorders is still poorly understood. According to currently emerging cell biological concepts, tau might play a role in the regulation of neuronal plasticity in a wide array of neuronal networks. In addition, it might be involved in regulating genome stability (Arendt, T., et al, Brain Research Bulletin, 2016, 126, 238-292).

In Alzheimer's disease, the two major proteinaceous deposits are extracellular senile plaques consisting of aggregated amyloid-β (Aβ) peptide and intraneuronal neurofibrillary tangles (NFTs) composed of aggregated tau (C. A. Ross, M. A. Poirier, *Nat. Med.* 2004, 10, 10-17; C. Ballatore, V. M. Y Lee, J. Q. Trojanowski. *Nat Rev Neurosci.* 2007, 8, 663-672). The development of ligands that can specifically target Aβ or tau deposits are essential for clinical diagnostic of Alzheimer's disease, as well as for evaluating the contribution of these respective aggregated species to the complex molecular pathology in Alzheimer's disease brain. Molecular scaffolds enabling visualization of Aβ deposits in humans with Alzheimer's disease by positron emission tomography (PET) imaging have been presented (W. E. Klunk, et al, *Ann. Neurol.* 2004, 55, 306-319; Y. Kudo, et al, *J. Nucl. Med.* 2007, 48, 553-561; and L. Yang, D., et al, *N. Engl. J. Med.* 2012, 367, 885-887). More recently, some molecular scaffolds targeting the other pathological hallmark in Alzheimer's disease, tau deposits, have also been recognized (G. W. Small, et al, *N. Eng. J. Med.* 2006, 355, 2652-2663; Taghavi, et al, *Alzheimers Dis.* 2011, 27, 835-843; M. T. Fodero-Tavoletti, et al, *Brain.* 2011, 134, 1089-1100; W. Zhang, et al, *Alzheimers Dis.* 2012, 31, 601-612; M. Maruyama, et al, *Neuron* 2013, 79, 1094-1108; and C. F. Xia, et al. *Alzheimers Dement.* 2013, 9, 666-676).

Luminescent conjugated oligothiophenes (LCOS) have been utilized for fluorescence imaging of protein aggregates. Compared to conventional ligands, LCOs have been shown to detect a wider range of disease-associated protein aggregates (A. Åslund, et al, ACS Chem. Biol. 2009, 4, 673-684; T. Klingstedt, et al, *Org. Biomol. Chem.* 2011, 9, 8356-8370; H. Shirani, et al, *Chemistry* 2015, 21, 15133-15137). In addition, LCOs having distinct chemical compositions can also be utilized for spectral assessment of distinct protein aggregates, such as Aβ or tau deposits in Alzheimer's disease (T. Klingstedt, et al, *Chemistry* 2013, 19, 10179-1019; T. Klingstedt, et al, *Chemistry* 2015, 21, 9072-9082.). Lately, a thiophene based tetrameric ligand, q-FTAA-CN with a striking higher affinity for Aβ deposits than aggregated species composed of tau was identified (M. Bäck, et al, *Chemistry.* 2016, 22, 18335-18338).

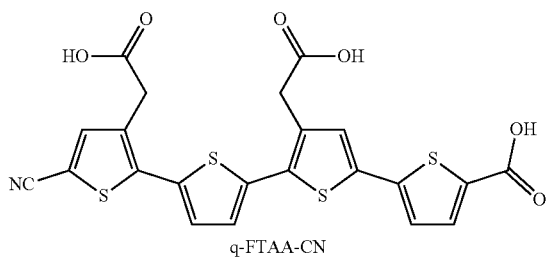 [SMILES: N#Cc1cc(CC(=O)O)c(-c2ccc(-c3sc(-c4ccc(C(=O)O)s4)cc3CC(=O)O)s2)s1]

q-FTAA-CN

PBB3 is also known to be a tau specific ligand (M. Maruyama, et al, *Neuron* 2013, 79, 1094-1108).

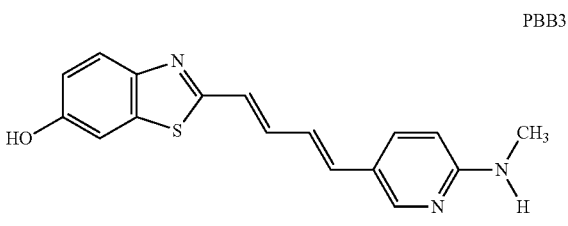 [SMILES: CNc1ccc(/C=C/C=C/c2nc3ccc(O)cc3s2)cn1]

PBB3

However, different morphotypes of Aβ and tau aggregates have been reported (C. L. Maarouf, let al, *Mol. Neurodegener.* 2008, 3, 20; H. Levine, L. C. Walker, *Neurobiol. Aging* 2010, 31, 542-548; F. Clavaguera, et al, *Proc. Natl. Acad. Sci. USA* 2013, 110, 9535-9540; J. X. Lu, et al, *Cell* 2013, 154, 1257-1268; W. Qiang, et al, *Nature.* 2017, 541, 217-221). The existence of distinct aggregate morphotypes has been suggested to explain the heterogeneous phenotype reported for several neurodegenerative protein aggregation diseases. Hence, a variety of ligands will be necessary to achieve an accurate assessment of the diversity of pathological protein deposits present in Alzheimer's disease. As such, there is a need to develop further small molecular ligands that target specific disease-associated protein aggregates, and in particular further molecular scaffolds enabling visualization of tau deposits, for example in humans with Alzheimer's disease (and other tauopathies).

SUMMARY OF INVENTION

The invention provides a compound of formula (I) or a pharmaceutically acceptable salt, ester, amide or carbamate thereof, or a salt of such an ester, amide or carbamate,

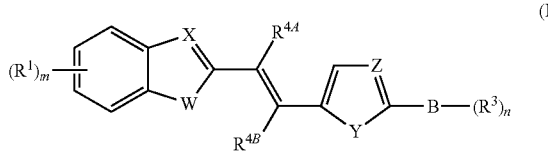

(I)

wherein
W is S, O or Se;
X is N or N$^+$—R$^2$;
Y is S or O;
Z is CH or N;
or Y is Se and Z is CH;
B is a 6 to 10 membered aromatic carbocycle or a 5 to 10 membered aromatic heterocycle having 1 to 3 heteroatoms selected from the group consisting of S, N, O and Se;
each R$^1$ is independently selected from the group consisting of —O—C$_{1-6}$alkyl, —O-monohaloC$_{1-6}$alkyl, —O-dihaloC$_{1-6}$alkyl, —O-trihaloC$_{1-6}$alkyl, C$_{1-6}$alkyl, monohaloC$_{1-6}$alkyl, dihaloC$_{1-6}$alkyl, trihaloC$_{1-6}$alkyl, OH, F, Cl, Br, I, and CN;
R$^2$ is selected from the group consisting of C$_{1-6}$alkyl, monohaloC$_{1-6}$alkyl, dihaloC$_{1-6}$alkyl, trihaloC$_{1-6}$alkyl, and C(O)C$_{1-6}$alkyl;
each R$^3$ is independently selected from the group consisting of —O—C$_{1-6}$alkyl, —O-monohaloC$_{1-6}$alkyl, —O-dihaloC$_{1-6}$alkyl, —O-trihaloC$_{1-6}$alkyl, —(CH$_2$)$_p$—O—C$_{1-6}$alkyl, —(CH$_2$)$_q$—C(O)—C$_{1-6}$alkyl, —(CH$_2$)$_r$—C(O)—O—C$_{1-6}$alkyl, —(CH$_2$)$_s$—N(R$^5$)$_2$, OH, F, Cl, Br, I, —CN, —C$_{1-6}$alkyl, monohaloC$_{1-6}$alkyl, dihaloC$_{1-6}$alkyl, and trihaloC$_{1-6}$alkyl;
R$^{4A}$ and R$^{4B}$ are independently selected from the group consisting of H, OH, F, Cl, Br, I, C$_{1-6}$alkyl, monohaloC$_{1-6}$alkyl, dihaloC$_{1-6}$alkyl, trihaloC$_{1-6}$alkyl, O—C$_{1-6}$alkyl, —O-monohaloC$_{1-6}$alkyl, —O-dihaloC$_{1-6}$alkyl, and —O-trihaloC$_{1-6}$alkyl;
each R$^5$ is independently selected from the group consisting of H and C$_{1-6}$alkyl;
m is 0, 1, 2 or 3; n is 0, 1, 2 or 3;
p is 1, 2 or 3, q is 0, 1, or 2; r is 0, 1, or 2; and s is 0, 1, 2 or 3.

The invention also provides a pharmaceutical or diagnostic composition comprising a compound of formula (I), together with a pharmaceutically suitable carrier.

The invention further provides a compound of formula (I) (or a composition comprising a compound of formula (I)) for use as a diagnostic agent wherein the compound of formula (I) comprises one or more radioisotopes selected from $^3$H, $^{11}$C, $^{13}$N, $^{15}$O, $^{18}$F, $^{120}$I, $^{123}$I, and $^{125}$I.

The invention further provides the use of a compound of formula (I) for the detection of tau deposits.

The invention further provides a method of diagnosing a patient or monitoring disease progression in a patient comprising administering a compound of formula (I) (or a composition comprising a compound of formula (I)) to the patient, wherein the compound of formula (I) comprises one or more radioisotopes selected from $^3$H, $^{11}$C, $^{13}$N, $^{15}$O, $^{18}$F, $^{120}$I, $^{123}$I, and $^{125}$I.

The invention further provides a compound of formula (I) or a composition comprising a compound of formula (I), for use as a medicament.

DESCRIPTION OF DRAWINGS

FIG. 5 is a table showing the excitation and emission maxima and the Stokes' shift for the Example Compounds 3a, 3b, 3c, 3d and 8a in DMSO, PBS or bound to intraneuronal neurofibrillary tangles (NFTs).

FIG. 6 shows fluorescence image (6a) and emission spectra (6B) of brain tissue sections with AD pathology stained with PBB3 (emission spectra of PBB3 bound to Aβ (left curve) or tau aggregates (right curve)). Scales bar represents 50 μm.

A-C) Fluorescence spectral images of frozen brain sections with Alzheimer's disease pathology simultaneously stained by 100 nM q-FTAA-CN and 100 nM example compound 3a.

D) Characteristic emission spectra (left curve) from q-FTAA-CN labelled Aβ deposits and example compound 3a stained tau aggregates (right curve).

E) Fluorescence images of frozen brain sections with AD-pathology simultaneously stained by 100 nM PBB3 and 100 nM example compound 3b.

F) Fluorescence images of frozen brain sections with AD-pathology pre-incubated with 1 µM PBB3 prior to staining with 10 nM example compound 3b.

G) Fluorescence images of frozen brain sections with AD-pathology stained with 10 nM example compound 3b.

H) Fluorescence images of frozen brain sections with AD-pathology pre-incubated with 1 βM q-FTAA-CN prior to staining with 10 nM example compound 3b.

Figure 8:
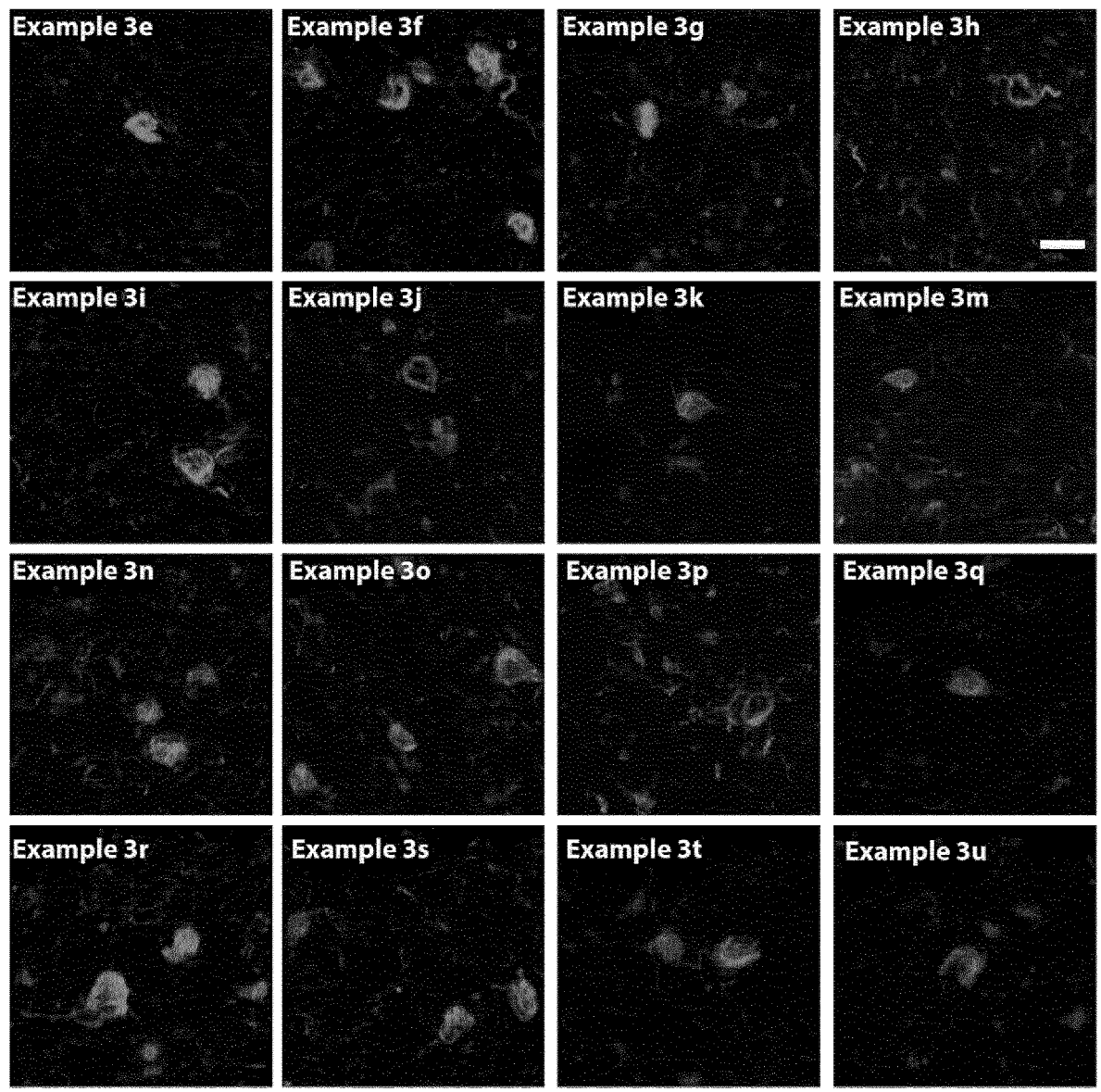

FIG. 8 shows brain tissue sections with Alzheimer's disease pathology stained by Example Compounds 3e, 3f, 3g, 3h, 3i, 3j, 3k, 3m, 3n, 3o, 3p, 3q, 3r, 3s, 3t or 3u. Scale bar represent 20 µm.

DETAILED DESCRIPTION

The present inventors have synthesized various compounds of formula (I) and shown that those compounds have a surprisingly high selectively toward tau pathology in Alzheimer's disease. As described in the Examples section, various example compounds were applied to brain tissue sections with Alzheimer's disease pathology and were shown to selectively identify tau pathology in Alzheimer's disease. Furthermore, the inventors have found that subtle changes in the structure of the compounds of formula (I) were shown to alter their capacity for selective identification of tau deposits. The compounds of formula (I) found by the present inventors find use in the clinical imaging of tau pathology in Alzheimer's disease.

Figure 7:
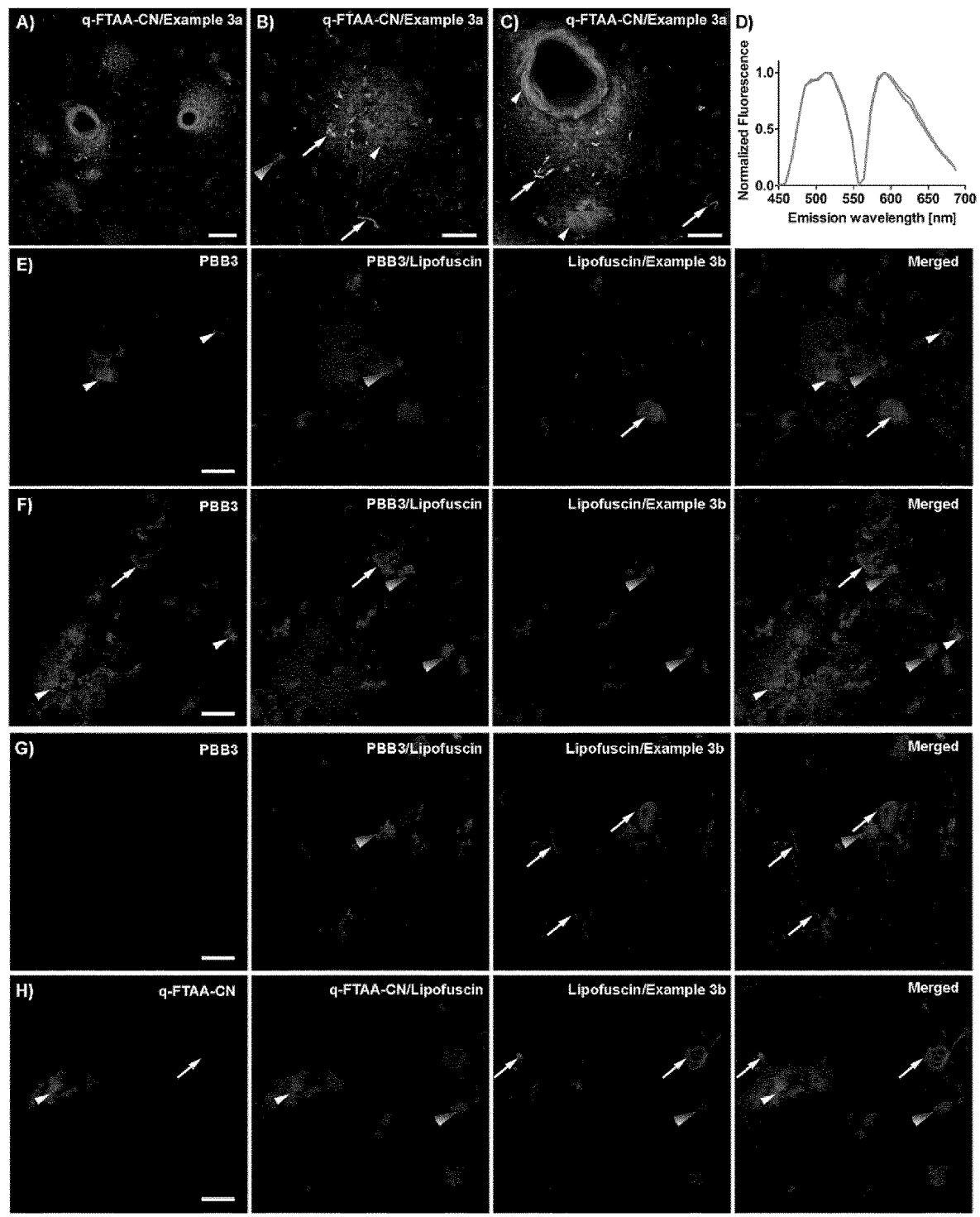
FIG. 7 shows fluorescence images of brain tissue sections with Alzheimer's disease pathology simultaneously stained by Example Compounds 3a or 3b and q-FTAA-CN or PBB3. Scale bars represent 50 μm (A) or 20 μm (B, C, E-H) and large arrow-heads indicate auto-fluorescence from lipofuscin.

The inventors have also found that compounds of the invention have a higher selectivity and most likely a higher affinity for tau deposits than the tau selective compound PBB3 in assays conducted to date (see, for example, the experiment results of part (iii) of the "Biological Testing of Example Compounds and Comparative Examples" section below, and FIG. 7).

The compounds of the invention may contain chiral (asymmetric) centres or the molecule as a whole may be chiral. The individual stereoisomers (enantiomers and diastereoisomers) and mixtures of these are within the scope of the present invention. Isotopic forms, for example where a hydrogen atom is replaced with deuterium or tritium, or a carbon atom is replaced with a $^{13}C$ atom are included within the invention. Certain isotopic forms may have beneficial biological properties, for example improved metabolic stability or enhanced therapeutic activity over other isotopic forms. Some specific isotopic forms may be useful for biological imaging purposes, for example carbon-11 ($^{11}C$), nitrogen-13 ($^{13}N$), oxygen-15 ($^{15}O$), fluorine-18 ($^{18}F$) or iodine-120 ($^{120}I$) isotopic variants may be used for positron emission tomography, and tritium ($^{3}H$) and iodine-125 (125I) may be used for in vitro studies.

The compounds of the invention contain a vinylene moiety (i.e. the —C($R^{4A}$)═C($R^{4B}$)— moiety/group in the compound of formula (I)). This may also be referred to as an ethenylene or 1,2-ethenediyl group or moiety. The vinylene moiety of the compounds of the invention is the isomer in which the heterocyclic groups attached to the vinylene moiety are trans to each other (and the two $R^4$ groups ($R^{4A}$ and $R^{4B}$) are trans to each other), herein referred to as the "trans isomer". The vinylene moiety in which the heterocyclic groups are cis to each other (and the two $R^4$ groups ($R^{4A}$ and $R^{4B}$) are cis to each other), is herein referred to as the "cis isomer". The individual trans isomer, and mixtures including the trans and cis isomers are within the scope of the present invention.

Where appropriate, a conterion is present. For example, if X is $N^+$—$R^2$, then a counter anion is present. Such a counter anion may be, for example, selected from the group consisting of I⁻ (Iodide), Br⁻ (bromide), Cl⁻ (Chloride), F⁻ (Fluoride), and H⁻ (Hydride), and especially I⁻.

The present invention provides compounds of formula (I):

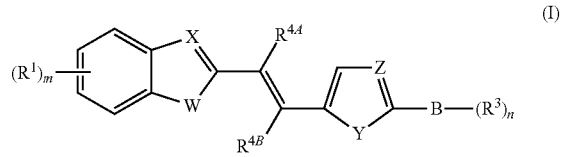

The present inventors have surprisingly found that the trans isomer of the vinylene moiety in the compounds of the invention has a major effect on the compounds' ability to detect Aβ and tau aggregates. If the trans vinylene moiety is replaced with a thiophene the ability to detect Aβ and tau aggregates is either reduced (see, for example, the results for Comparative Example 2 and 4 in part (i) of the Biological Results section, below), or the selectivity for tau over Aβ is lost (see, for example, the results for Comparative Example 3 in part (i) of the Biological Results section, below).

In one embodiment the present invention provides a compound of formula (I)

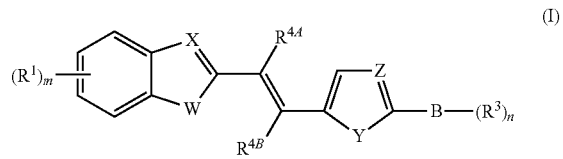

wherein
W is S, O or Se;
X is N or $N^+$—$R^2$;
Y is S or O;
Z is CH or N;
or Y is Se and Z is CH;
B is a 6 to 10 membered aromatic carbocycle or a 5 to 10 membered aromatic heterocycle having 1 to 3 heteroatoms selected from the group consisting of S, N, O and Se;
each $R^1$ is independently selected from the group consisting of —O—$C_{1-6}$alkyl, —O-monohalo$C_{1-6}$alkyl, —O-diha-lo$C_{1-6}$alkyl, —O-trihalo$C_{1-6}$alkyl, $C_{1-6}$alkyl, monohalo$C_{1-6}$alkyl, dihalo$C_{1-6}$alkyl, trihalo$C_{1-6}$alkyl, OH, F, Cl, Br, I, and CN;
$R^2$ is selected from the group consisting of $C_{1-6}$alkyl, monohalo$C_{1-6}$alkyl, dihalo$C_{1-6}$alkyl, trihalo$C_{1-6}$alkyl, and C(O)$C_{1-6}$alkyl;
each $R^3$ is independently selected from the group consisting of —O—$C_{1-6}$alkyl, —O-monohalo$C_{1-6}$alkyl, —O-diha-lo$C_{1-6}$alkyl, —O-trihalo$C_{1-6}$alkyl, —$(CH_2)_p$—O—$C_{1-6}$al-kyl, —$(CH_2)_q$—C(O)—$C_{1-6}$alkyl, —$(CH_2)_r$—C(O)—O—

$C_{1-6}$alkyl, —$(CH_2)_s$—$N(R^5)_2$, OH, F, Cl, Br, I, —CN, —$C_{1-6}$alkyl, monohalo$C_{1-6}$alkyl, dihalo$C_{1-6}$alkyl, and trihalo$C_{1-6}$alkyl;

$R^{4A}$ and $R^{4B}$ are independently selected from the group consisting of H, OH, F, Cl, Br, I, $C_{1-6}$alkyl, monohalo$C_{1-6}$alkyl, dihalo$C_{1-6}$alkyl, trihalo$C_{1-6}$alkyl, O—$C_{1-6}$alkyl, —O-monohalo$C_{1-6}$alkyl, —O-dihalo$C_{1-6}$alkyl, and —O-trihalo$C_{1-6}$alkyl;

each $R^5$ is independently selected from the group consisting of H and $C_{1-6}$alkyl;

m is 0, 1, 2 or 3; n is 0, 1, 2 or 3;

p is 1, 2 or 3, q is 0, 1, or 2; r is 0, 1, or 2; and s is 0, 1, 2 or 3.

In the compound of formula (I), W may be S, O or Se. In one preferred embodiment, W is S or O, and more preferably W is S. In another preferred embodiment, W is Se when X is N.

It is noted that W must not be N. As shown in the Examples section below, compounds having W=N are no longer selective for tau, but instead are selective for Aβ. Hence, the present inventors have found that by having a N atom at the W position, the specificity toward tau-only pathology is abolished. It is surprising that this minor chemical alteration can have such a significant impact on the compounds' ability to selectively bind to protein deposits.

In the compound of formula (I), X may be N or $N^+$—$R^2$. In certain embodiments it is preferable that X is N. In other embodiments, it is preferable that X is $N^+$—$R^2$.

$R^2$ is selected from the group consisting of $C_{1-6}$alkyl, monohalo$C_{1-6}$alkyl, dihalo$C_{1-6}$alkyl, trihalo$C_{1-6}$alkyl, and $C(O)C_{1-6}$alkyl. Preferably, $R^2$ is selected from the group consisting of $C_{1-6}$alkyl, monofluoro$C_{1-6}$alkyl, difluoro$C_{1-6}$alkyl, and trifluoro$C_{1-6}$alkyl; more preferably $R^2$ is selected from the group consisting of $C_{1-4}$alkyl, monofluoro$C_{1-4}$alkyl, difluoro$C_{1-4}$alkyl, and trifluoro$C_{1-4}$alkyl; and even more preferably $R^2$ is selected from the group consisting of methyl, ethyl, propyl, isopropyl, butyl, isobutyl, tertbutyl and trifluoromethyl. In one very preferred embodiment, $R^2$ is selected from the group consisting of methyl and ethyl.

In the compound of formula (I), Y may be S or O. In certain preferred embodiments, Y is S.

In the compound of formula (I), Z may be CH or N. In certain preferred embodiments, Z is CH.

In the compound of formula (I), Y may also be Se when Z is CH.

In especially preferred embodiments of the invention Y is S and Z is CH. It is also preferred that Y is Se and Z is CH. In very especially preferred embodiments of the invention Y is S.

In another preferred embodiment of the invention Y is S, O or Se (preferably S or O, and more preferably S), and Z is CH, and W is S or Se (preferably S). Even more preferably, Y is S, O or Se (preferably S or O, and more preferably S), Z is CH, W is S or Se (preferably S), and X is $N^+$—$R^2$.

In the compound of formula (I) each $R^1$ may be independently selected from the group consisting of —O—$C_{1-6}$alkyl, —O-monohalo$C_{1-6}$alkyl, —O-dihalo$C_{1-6}$alkyl, —O-trihalo$C_{1-6}$alkyl, $C_{1-6}$alkyl, monohalo$C_{1-6}$alkyl, dihalo$C_{1-6}$alkyl, trihalo$C_{1-6}$alkyl, OH, F, Cl, Br, I, and CN. Preferably each $R^1$ may be independently selected from the group consisting of —O—$C_{1-6}$alkyl, —O-monohalo$C_{1-6}$alkyl, —O-dihalo$C_{1-6}$alkyl, —O-trihalo$C_{1-6}$alkyl, $C_{1-6}$alkyl, monohalo$C_{1-6}$alkyl, dihalo$C_{1-6}$alkyl, trihalo$C_{1-6}$alkyl, OH, F, Br, I, and CN. More preferably each $R^1$ is independently selected from the group consisting of —O—$C_{1-6}$alkyl, —O-monohalo$C_{1-6}$alkyl, —O-dihalo$C_{1-6}$alkyl, —O-trihalo$C_{1-6}$alkyl, $C_{1-6}$alkyl, monohalo$C_{1-6}$alkyl, dihalo$C_{1-6}$alkyl, trihalo$C_{1-6}$alkyl, OH and F. Even more preferably each $R^1$ is independently selected from the group consisting of —O—$C_{1-4}$alkyl, —O-monofluoro$C_{1-4}$alkyl, —O-difluoro$C_{1-4}$alkyl, —O-trifluoro$C_{1-4}$alkyl, $C_{1-4}$alkyl, monofluoro$C_{1-4}$alkyl, difluoro$C_{1-4}$alkyl, trifluoro$C_{1-4}$alkyl, OH and F. In another preferred embodiment each $R^1$ is independently selected from the group consisting of —O—$C_{1-6}$alkyl, —O-monofluoro$C_{1-6}$alkyl, —O-difluoro$C_{1-6}$alkyl, —O-trifluoro$C_{1-6}$alkyl. Most preferably each $R^1$ is independently selected from the group consisting of —O—$C_{1-6}$alkyl, for example —O—$C_{1-4}$alkyl (e.g. —O-methyl, —O-ethyl, —O-propyl, —O-isopropyl, —O-butyl, —O-isobutyl or —O-tertbutyl).

In the compound of formula (I), $R^{4A}$ and $R^{4B}$ are independently selected from the group consisting of H, OH, F, Cl, Br, I, $C_{1-6}$alkyl (for example, $C_{2-6}$alkyl; preferably $C_{1-4}$alkyl, or $C_{2-4}$alkyl), monohalo$C_{1-6}$alkyl, dihalo$C_{1-6}$alkyl, trihalo$C_{1-6}$alkyl, O—$C_{1-6}$alkyl, —O-monohalo$C_{1-6}$alkyl, —O-dihalo$C_{1-6}$alkyl, and —O-trihalo$C_{1-6}$alkyl (i.e. $R^{4A}$ may be selected from the group consisting of H, OH, F, Cl, Br, I, $C_{1-6}$alkyl (for example, $C_{2-6}$alkyl; preferably $C_{1-4}$alkyl, or $C_{2-4}$alkyl), monohalo$C_{1-6}$alkyl, dihalo$C_{1-6}$alkyl, trihalo$C_{1-6}$alkyl, O—$C_{1-6}$alkyl, —O-monohalo$C_{1-6}$alkyl, —O-dihalo$C_{1-6}$alkyl, and —O-trihalo$C_{1-6}$alkyl; and $R^{4B}$ may be selected from the group consisting of H, OH, F, Cl, Br, I, $C_{1-6}$alkyl (for example, $C_{2-6}$alkyl; preferably $C_{1-4}$alkyl, or $C_{2-4}$alkyl), monohalo$C_{1-6}$alkyl, dihalo$C_{1-6}$alkyl, trihalo$C_{1-6}$alkyl, O—$C_{1-6}$ alkyl, —O-monohalo$C_{1-6}$alkyl, —O-dihalo$C_{1-6}$alkyl, and —O-trihalo$C_{1-6}$alkyl)). Preferably $R^{4A}$ and $R^{4B}$ are independently selected from the group consisting of H, F, $C_{1-4}$alkyl (for example, $C_{2-4}$alkyl), monofluoro$C_{1-4}$alkyl, difluoro$C_{1-4}$alkyl, and trifluoro$C_{1-4}$alkyl. Even more preferably, $R^{4A}$ and $R^{4B}$ are independently selected from the group consisting of H, F, methyl, ethyl, propyl, isopropyl, butyl, tertbutyl, isobutyl, and trifluoromethyl.

In certain preferred embodiments, one $R^4$ group (i.e. $R^{4A}$ or $R^{4B}$) is H and one $R^4$ group (i.e. $R^{4A}$ or $R^{4B}$) is selected from the group consisting of H, F, methyl, ethyl, propyl, isopropyl, butyl, tertbutyl, isobutyl, and trifluoromethyl. For example, $R^{4A}$ is H and $R^{4B}$ is selected from the group consisting of H, F, methyl, ethyl, propyl, isopropyl, butyl, tertbutyl, isobutyl, and trifluoromethyl; or $R^{4B}$ is H and $R^{4A}$ is selected from the group consisting of H, F, methyl, ethyl, propyl, isopropyl, butyl, tertbutyl, isobutyl, and trifluoromethyl (and preferably H, F, ethyl, propyl, isopropyl, butyl, tertbutyl, isobutyl, and trifluoromethyl). In such embodiments, optionally $R^{4A}$ and $R^{4B}$ may also be independently selected from the group consisting of F, methyl, ethyl, propyl, isopropyl, butyl, tertbutyl, isobutyl, and trifluoromethyl.

In another embodiment, $R^{4A}$ and $R^{4B}$ are independently selected from the group consisting of OH, F, Cl, Br, I, $C_{1-6}$alkyl (for example, $C_{2-6}$alkyl; preferably $C_{1-4}$alkyl, or $C_{2-4}$alkyl), monohalo$C_{1-6}$alkyl, dihalo$C_{1-6}$alkyl, trihalo$C_{1-6}$alkyl, O—$C_{1-6}$alkyl, —O-monohalo$C_{1-6}$alkyl, —O-dihalo$C_{1-6}$alkyl, and —O-trihalo$C_{1-6}$alkyl; or $R^{4A}$ is selected from the group consisting of OH, F, Cl, Br, I, $C_{2-6}$alkyl (for example, $C_{2-6}$alkyl; preferably $C_{2-4}$alkyl), monohalo$C_{1-6}$alkyl, dihalo$C_{1-6}$alkyl, trihalo$C_{1-6}$alkyl, O—$C_{1-6}$alkyl, —O-monohalo$C_{1-6}$alkyl, —O-dihalo$C_{1-6}$alkyl, and —O-trihalo$C_{1-6}$alkyl, and $R^{4B}$ is selected from the group consisting of OH, F, Cl, Br, I, $C_{1-6}$alkyl (for example, $C_{2-6}$alkyl; preferably $C_{1-4}$alkyl, or $C_{2-4}$alkyl), monohalo$C_{1-6}$alkyl, dihalo$C_{1-6}$alkyl, trihalo$C_{1-6}$alkyl, O—$C_{1-6}$alkyl, —O-monohalo$C_{1-6}$alkyl, —O-dihalo$C_{1-6}$alkyl, and —O-trihalo$C_{1-6}$alkyl.

In another embodiment, $R^{4A}$ and $R^{4B}$ are independently selected from the group consisting of H, OH, F, Cl, Br, I, $C_{2-6}$alkyl monohalo$C_{1-6}$alkyl, dihalo$C_{1-6}$alkyl, trihalo$C_{1-6}$alkyl, O—$C_{1-6}$alkyl, —O-monohalo$C_{1-6}$alkyl, —O-dihalo$C_{1-6}$alkyl, and —O-trihalo$C_{1-6}$alkyl, for example $R^{4A}$ and $R^{4B}$ are independently selected from the group consisting of H, F, $C_{2-4}$alkyl monofluoro$C_{1-4}$alkyl, difluoro$C_{1-4}$alkyl, and trifluoro$C_{1-4}$alkyl.

$R^{4A}$ and $R^{4B}$ may be the same or may be different. In especially preferred embodiments, $R^{4A}$ and $R^{4B}$ are the same and are, for example, H.

In one preferred embodiment, $R^{4A}$ and $R^{4B}$ are H. For example, in one preferred embodiment, the compound of formula (I) is the compound of formula (Ia):

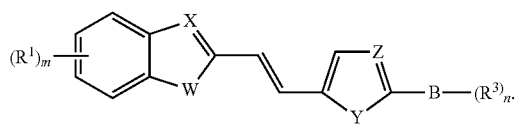
(Ia)

In another preferred embodiment, the compound of formula (I) is the compound of formula (Ib):

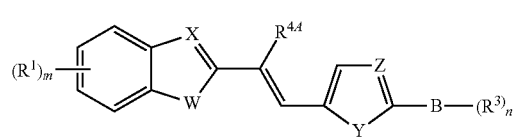
(Ib)

wherein $R^{4A}$ is as defined above. For example, the compound of formula (I) is a compound of formula (Ib) wherein $R^{4A}$ is selected from the group consisting of H, F, $C_{1-4}$alkyl, monofluoro$C_{1-4}$alkyl, difluoro$C_{1-4}$alkyl, and trifluoro$C_{1-4}$alkyl; or wherein $R^{4A}$ is selected from the group consisting of H, F, $C_{2-4}$alkyl, monofluoro$C_{1-4}$alkyl, difluoro$C_{1-4}$alkyl, and trifluoro$C_{1-4}$alkyl; or wherein $R^{4A}$ is selected from the group consisting of H, F, monofluoro$C_{1-4}$alkyl, difluoro$C_{1-4}$alkyl, and trifluoro$C_{1-4}$alkyl.

In another preferred embodiment, the compound of formula (I) is a compound of formula (Ic),

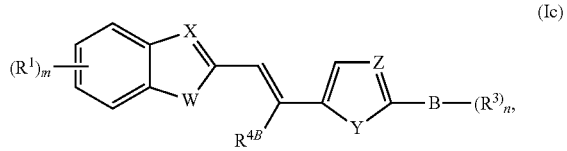
(Ic)

wherein $R^{4B}$ is as defined above. For example, the compound of formula (I) is a compound of formula (Ib) wherein $R^{4B}$ is selected from the group consisting of H, F, $C_{1-4}$alkyl, monofluoro$C_{1-4}$alkyl, difluoro$C_{1-4}$alkyl, and trifluoro$C_{1-4}$alkyl.

In one preferred embodiment, the compound of formula (I) is selected from the group consisting of the compound of formula (Ia), (Ib) and (Ic), for example: the compound of formula (Ia) or (Ib); or the compound of formula (Ia) or (Ic).

In the compound of formula (I), m may be 0, 1, 2 or 3. Preferably m is 0 or 1. In certain preferred embodiments, m is 0, and the compound of formula (I) has the following structure:

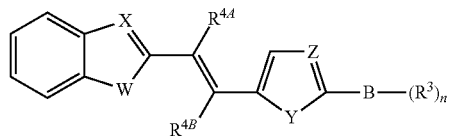

In another preferred embodiment, m is 1. In embodiments wherein m is 1, the compound of formula (I) may be is selected from:

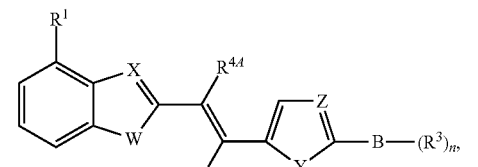

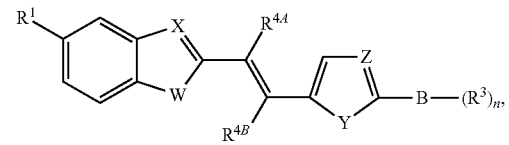

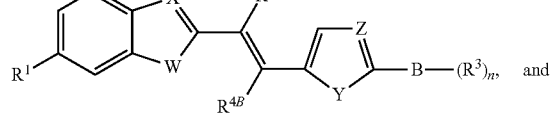
and

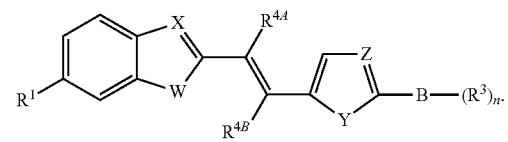

Preferably in embodiments where m is 1, the compound of formula (I) has the following structure:

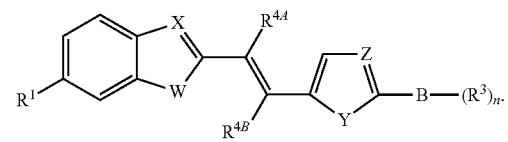

In the compound of formula (I), B may be a 6 to 10 membered aromatic carbocycle or a 5 to 10 membered aromatic heterocycle having 1 to 3 heteroatoms selected from the group consisting of S, N, O and Se (preferably S, N and O). B may be monocyclic or bicyclic. More preferably B is a 5 to 10 membered aromatic heterocycle having 1 to 3 (for example 1 or 2) heteroatoms selected from the group consisting of S, N, O and Se (preferably S, N and O). When B is a 5 to 10 membered aromatic heterocycle it may be monocyclic or bicyclic. For example, B may be one of the heterocycles listed below comprising one or more of S, N, O and Se.

For example, B may be selected from the group consisting of phenyl, naphthyl, indanyl, furanyl, pyrrolyl, imidazolyl, pyridinyl (also known as pyridyl), pyrimidinyl, pyridazinyl, pyrazinyl, pyrazolyl, thiophenyl (also known as thienyl), oxazolyl, isoxazolyl, dioxazolyl, oxadiazolyl, thiazolyl, isothiazolyl, thiadiazolyl, triazolyl, triazinyl, pyridazyl, indolyl, isoindolyl, indolizinyl, quinolinyl, isoquinolinyl, purinyl, benzopyranyl, benzofuranyl, benzothiazolyl, benzothiophenyl, benzoxazolyl, benzodioxolyl, benzothiadiazolyl, quinoxalinyl, quinazolinyl, pyridopyrazinyl, benzimidazolyl, naphthyridinyl, oxazolyl[4,5-b]pyridinyl, pyridopyrimidinyl, isoquinolinyl, benzoxazole, dihydrobenzofuranyl, indolinyl, isoindolinyl, tetrahydroisoquinolinyl, tetrahydroquinolyl, benzoazepanyl, selenophene, selenazole, isoselenazole and benzoselenazole. Preferably B is selected from the group consisting of indanyl, furanyl, pyrrolyl, imidazolyl, pyridinyl (also known as pyridyl), pyrimidinyl, pyridazinyl, pyrazinyl, pyrazolyl, thiophenyl (also known as thienyl), oxazolyl, isoxazolyl, dioxazolyl, oxadiazolyl, thiazolyl, isothiazolyl, thiadiazolyl, triazolyl, triazinyl, pyridazyl, indolyl, isoindolyl, indolizinyl, quinolinyl, isoquinolinyl, purinyl, benzopyranyl, benzofuranyl, benzothiazolyl, benzothiophenyl, benzoxazolyl, benzodioxolyl, benzothiadiazolyl, quinoxalinyl, quinazolinyl, pyridopyrazinyl, benzimidazolyl, naphthyridinyl, oxazolyl[4,5-b]pyridinyl, pyridopyrimidinyl, isoquinolinyl, benzoxazole, dihydrobenzofuranyl, indolinyl, isoindolinyl, tetrahydroisoquinolinyl, tetrahydroquinolyl, benzoazepanyl, selenophene, selenazole, isoselenazole and benzoselenazole.

Preferably B is a 6 to 10 membered aromatic carbocycle or a 5 to 10 membered aromatic heterocycle having 1 to 3 heteroatoms selected from the group consisting of S, N and O. For example, B may be one of the carbocycles listed above, or heterocycles listed above comprising one or more of S, N and O. Even more preferably B is a 5 to 10 membered aromatic heterocycle having 1 to 3 (for example 1 or 2) heteroatoms selected from the group consisting of S, N and O. For example, B may be one of the heterocycles listed above comprising one or more of S, N and O.

In a very especially preferred embodiments, B is a 5 or 6 membered monocyclic aromatic heterocycle having 1 to 3 heteroatoms selected from the group consisting of S, N, O and Se (and more preferably S, N and O); or a 9 or 10 membered bicyclic aromatic heterocycle having 1 to 3 heteroatoms selected from the group consisting of S, N O and Se (and more preferably S, N and O). For example, B may be one of the 5 or 6 membered monocyclic aromatic heterocycles, or 9 or 10 membered bicyclic aromatic heterocycles, listed above. More preferably B is furanyl, pyrrolyl, imidazolyl, imidazolyl, pyridinyl, pyrimidinyl, pyridazinyl, pyrazinyl, thiophenyl, thiophenyl, isoxazolyl, dioxazolyl, thiazolyl, isathiazolyl, thiadiazolyl, indolyl, isoindolyl, indolizinyl, quinolinyl, isoquinolinyl, purinyl, benzopyranyl, benzofuranyl, benzothiazolyl, benzothiophenyl, benzoxazolyl, benzodioxolyl, benzothiadiazolyl, selenophene, selenazole and isoselenazole. In certain preferred embodiments, B is furanyl, thiophenyl, pyridinyl, benzoioxolanyl, or benzothiadiazolyl.

In certain preferred embodiments, B is a 5 or 6 membered monocyclic aromatic heterocycle having 1 to 3 heteroatoms selected from the group consisting of S, N, O and Se. For example, B may be one of the 5 or 6 membered monocyclic aromatic heterocycles listed above. More preferably B is a 5 or 6 membered monocyclic aromatic heterocycle having 1 or 2 heteroatoms selected from the group consisting of S, N, O and Se (preferably S, N or O). For example, B may be selected from the group consisting of furanyl, pyrrolyl, imidazolyl, imidazolyl, pyridinyl, pyrimidinyl, pyridazinyl, pyrazinyl, thiophenyl, thiophenyl, isoxazolyl, dioxazolyl, thiazolyl, isathiazolyl, selenophene, selenazole and isoselenazole. In certain preferred embodiments, B is furanyl or thiophenyl or pyridinyl or selenophene, and even more preferably furanyl or thiophenyl or pyridinyl.

In certain preferred embodiments, B is a 5 or 6 membered monocyclic aromatic heterocycle having 1 to 3 heteroatoms selected from the group consisting of S, N, and O (preferably S and N). For example, B may be one of the 5 or 6 membered monocyclic aromatic heterocycles comprising a S, N or O above listed. More preferably B is a 5 or 6 membered monocyclic aromatic heterocycle having 1 or 2 heteroatoms selected from the group consisting of S, N and O (preferably S and N). For example, B may be selected from the group consisting of furanyl, pyrrolyl, imidazolyl, imidazolyl, pyridinyl, pyrimidinyl, pyridazinyl, pyrazinyl, thiophenyl, thiophenyl, isoxazolyl, dioxazolyl, thiazolyl, and isathiazolyl. In certain preferred embodiments, B is furanyl or thiophenyl or pyridinyl. In certain preferred embodiments, the B is a 5 or 6 membered monocyclic aromatic heterocycle having 1 or 2 heteroatoms (preferably 1 heteroatom) selected from the group consisting of S and N, for example B is thiophenyl or pyridinyl.

In certain preferred embodiments, B is a 9 or 10 membered bicyclic aromatic heterocycle having 1 to 3 heteroatoms selected from the group consisting of S, N, O and Se (and more preferably S, N and O). For example, B may be one of the 9 or 10 membered bicyclic aromatic heterocycles listed above. More preferably, B is a 9 or 10 membered bicyclic aromatic heterocycle having 2 or 3 heteroatoms selected from the group consisting of S and N, or O. For example, B may be selected from the group consisting of indolyl, isoindolyl, indolizinyl, quinolinyl, isoquinolinyl, purinyl, benzopyranyl, benzofuranyl, benzothiazolyl, benzothiophenyl, benzoxazolyl, benzodioxolyl and benzothiadiazolyl. In certain preferred embodiments, B is benzodioxolyl or benzothiadiazolyl.

In certain preferred embodiments, the B—(R³)$_n$ group is selected from the group consisting of:

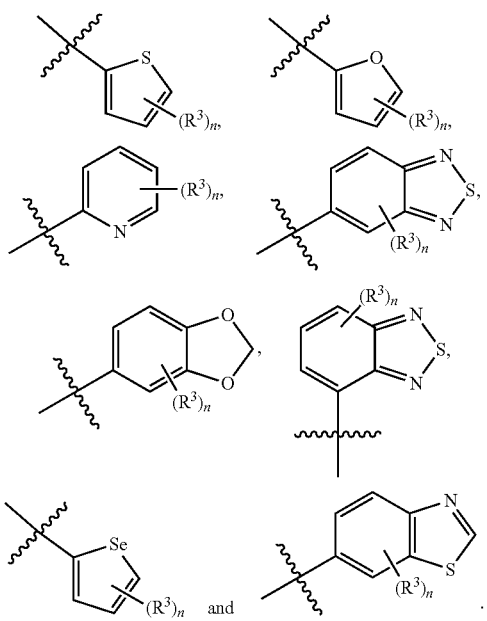

For example, the B—(R³)ₙ group is

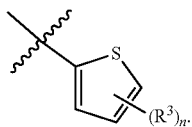

In another preferred embodiment, n is 0 or 1 and the B—(R³)ₙ group is selected from the group consisting of:

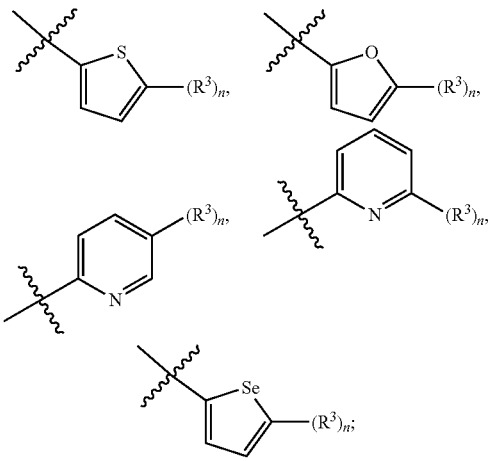

or n is 0 and the B—R³ group is selected from the group consisting of:

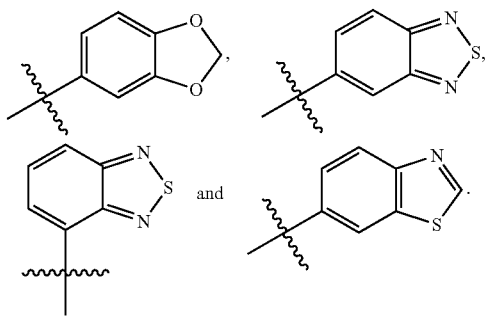

For example, n is 0 or 1 and the B—(R³)ₙ group is

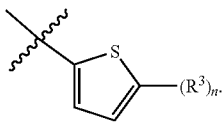

In another preferred embodiment, n is 1 and the B—(R³)ₙ group is selected from the group consisting of:

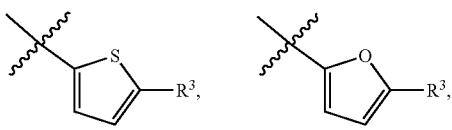

-continued

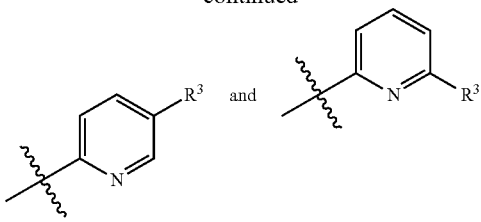

For example, B is

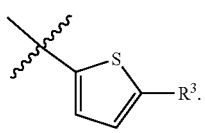

In one especially preferred embodiment Y is S; and B is a 5 to 10 membered aromatic heterocycle having 1 to 3 (for example 1 or 2) heteroatoms selected from the group consisting of S, N and O. More preferably Y is S; and B is a 5 or 6 membered monocyclic aromatic heterocycle having 1 to 3 heteroatoms selected from the group consisting of S, N, and O (preferably S and N) (for example one of the 5 or 6 membered monocyclic aromatic heterocycles comprising a S, N or O above listed). Even more preferably Y is S; and B is a 5 or 6 membered monocyclic aromatic heterocycle having 1 or 2 heteroatoms selected from the group consisting of S, N and O (preferably S and N) (for example, B may be selected from the group consisting of furanyl, pyrrolyl, imidazolyl, imidazolyl, pyridinyl, pyrimidinyl, pyridazinyl, pyrazinyl, thiophenyl, thiophenyl, isoxazolyl, dioxazolyl, thiazolyl, and isathiazolyl, and preferably furanyl or thiophenyl or pyridinyl). Even more preferably Y is S; and B is a 5 or 6 membered monocyclic aromatic heterocycle having 1 or 2 heteroatoms (preferably 1 heteroatom) selected from the group consisting of S and N, for example B is thiophenyl or pyridinyl (e.g. the B—(R³)ₙ group is

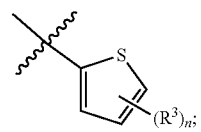

or the B—(R³)ₙ group

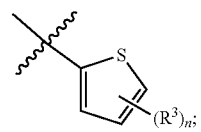

is wherein is 0 or 1).

R³ is independently selected from the group consisting of —O—C₁₋₆alkyl, —O-monohaloC₁₋₆alkyl, —O-dihaloC₁₋₆alkyl, —O-trihaloC₁₋₆alkyl, —(CH₂)ₚ—O—C₁₋₆alkyl, —(CH₂)_q—C(O)—C₁₋₆alkyl, —(CH₂)ᵣ—C(O)—O—C₁₋₆alkyl, —(CH₂)ₛ—N(R⁵)₂ (for example —(CH₂)—N(R⁵)₂, —(CH₂)₂—N(R⁵)₂, —(CH₂)₃—N(R⁵)₂, or —N(R⁵)₂; and when it is —N(R⁵)₂ preferably one R⁵ is C₁₋₆alkyl (for example C₁₋₄alkyl), and the other R⁵ is H or C₁₋₆alkyl (for example C$_{1-6}$alkyl); and even more preferably the other R$^5$ is H), OH, F, Cl, Br, I, —CN, —C$_{1-6}$alkyl, monohaloC$_{1-6}$alkyl, dihaloC$_{1-6}$alkyl, and trihaloC$_{1-6}$alkyl.

n may be 0, 1, 2 or 3. In embodiments wherein n is 2 or 3, each R$^3$ group may be the same or may be different. In preferred embodiments, n is 0 or 1.

p is 1, 2 or 3. Preferably, p is 1 (when p is 1 the R$^3$ group —(CH$_2$)$_p$—O—C$_{1-6}$alkyl=—(CH$_2$)—O—C$_{1-6}$alkyl). q is 0, 1, or 2. Preferably q is 0 or 1, and more preferably q is 0 (when q is 0 the R$^3$ group —(CH$_2$)$_q$—C(O)—C$_{1-6}$alkyl=—C(O)—C$_{1-6}$alkyl). r is 0, 1, or 2. Preferably r is 0 or 1 (when r is 0 or 1 the R$^3$ group —(CH$_2$)$_r$—C(O)—O—C$_{1-6}$alkyl=—C(O)—O—C$_{1-6}$alkyl or —(CH$_2$)—C(O)—O—C$_{1-6}$alkyl). s is 0, 1, 2 or 3. Preferably, s is 0 (when s is 0 the R$^3$ group —(CH$_2$)$_s$—N(R$^5$)$_2$ is —N(R$^5$)$_2$). In another very preferred embodiment, s is 1, 2, or 3 (i.e. s is not 0).

In certain preferred embodiments, R$^3$ is independently selected from the group consisting of —O—C$_{1-6}$alkyl, —O-monohaloC$_{1-6}$alkyl, —O-dihaloC$_{1-6}$alkyl, —O-trihaloC$_{1-6}$alkyl, —(CH$_2$)$_p$—O—C$_{1-6}$alkyl, —(CH$_2$)$_q$—C(O)—C$_{1-6}$alkyl, —(CH$_2$)$_r$—C(O)—O—C$_{1-6}$alkyl, —(CH$_2$)$_s$—N(R$^5$)$_2$ (for example —(CH$_2$)—N(R$^5$)$_2$, —(CH$_2$)$_2$—N(R$^5$)$_2$, —(CH$_2$)$_3$—N(R$^5$)$_2$, or —N(R$^5$)$_2$; and when it is —N(R$^5$)$_2$ preferably one R$^5$ is C$_{1-6}$alkyl (for example C$_{1-4}$alkyl), and the other R$^5$ is H or C$_{1-6}$alkyl (for example C$_{1-4}$alkyl); and even more preferably the other R$^5$ is H), OH, F, Cl, Br, I, and —CN (and preferably p is 1; q is 0 or 1; r is 0 or 1; and s is 0, 1 or 2). More preferably R$^3$ is independently selected from the group consisting of —O—C$_{1-4}$alkyl, —O-monofluoroC$_{1-4}$alkyl, —O-difluoroC$_{1-4}$alkyl, —O-trifluoroC$_{1-4}$alkyl, —(CH$_2$)$_p$—O—C$_{1-4}$alkyl, —(CH$_2$)$_q$—C(O)—C$_{1-4}$alkyl, —(CH$_2$)$_r$—C(O)—O—C$_{1-4}$alkyl, —N(R$^5$)$_2$ (preferably one R$^5$ is C$_{1-6}$alkyl (for example C$_{1-4}$alkyl), and the other R$^5$ is H or C$_{1-6}$alkyl (for example C$_{1-4}$alkyl); and even more preferably the other R$^5$ is H), F, Cl, Br, I, and —CN (and preferably p is 1; q is 0 or 1; and r is 0 or 1). In another preferred embodiment, R$^3$ is independently selected from the group consisting of —O—C$_{1-4}$alkyl, —(CH$_2$)—O—C$_{1-6}$alkyl, —(CH$_2$)$_q$—C(O)—C$_{1-6}$alkyl, —(CH$_2$)$_r$—C(O)—O—C$_{1-6}$alkyl, —N(R$^5$)$_2$ (preferably one R$^5$ is C$_{1-6}$alkyl (for example C$_{1-4}$alkyl), and the other R$^5$ is H or C$_{1-6}$alkyl (for example C$_{1-4}$alkyl); and even more preferably the other R$^5$ is H), F, I, and —CN, (and preferably p is 1; q is 0 or 1; and r is 0 or 1;); and more preferably is independently selected from the group consisting of —O—C$_{1-4}$alkyl, —(CH$_2$)—O—C$_{1-4}$alkyl, —(CH$_2$)$_q$—C(O)—C$_{1-4}$alkyl, —(CH$_2$)$_r$—C(O)—O—C$_{1-4}$alkyl, NH(C$_{1-4}$alkyl), F, I, and —CN, (and preferably p is 1; q is 0 or 1; and r is 0 or 1).

In an especially preferred embodiment, R$^3$ is independently selected from the group consisting of O-methyl, —C(O)—O-methyl, —C(O)-methyl, —CH$_2$—C(O)—O-methyl, NH(methyl), F, I and CN.

In the compound of formula (I), n may be 0, 1, 2 or 3. Preferably n is 0 or 1. In one preferred embodiment, n is 0. In another preferred embodiment, n is 1.

Each R$^5$ is independently selected from the group consisting of H and C$_{1-6}$alkyl, and more preferably H and C$_{1-4}$alkyl. In certain preferred embodiments, one R$^5$ of a "N(R$^5$)$_2$" (e.g. a—N(R$^5$)$_2$ or a —(CH$_2$)$_s$N(R$^5$)$_2$) group is H, and the other R$^5$ of the "N(R$^5$)$_2$" group is H or C$_{1-6}$alkyl (and more preferably the other R$^5$ of the "N(R$^5$)$_2$" group is C$_{1-6}$alkyl). In another embodiment, one R$^5$ of a "N(R$^5$)$_2$" group is C$_{1-6}$alkyl, and the other R$^5$ of the "N(R$^5$)$_2$" group is H or C$_{1-6}$alkyl. In another especially preferred embodiment, one R$^5$ of a "N(R$^5$)$_2$" group is C$_{1-6}$alkyl (for example C$_{1-4}$alkyl), and the other R$^5$ of the "N(R$^5$)$_2$" group is H or C$_{1-6}$alkyl (for example C$_{1-4}$alkyl); and even more preferably one R$^5$ of a "N(R$^5$)$_2$" group is C$_{1-6}$alkyl (for example C$_{1-4}$alkyl), and the other R$^5$ of the "N(R$^5$)$_2$" group is H.

Compounds of formula (I) include, but are not limited to, the compounds specifically mentioned in the Examples herein, including pharmaceutically acceptable esters, amides, carbamates or salts thereof, including salts of such esters, amides or carbamates.

The compound of formula (I) may be selected from the group consisting of:

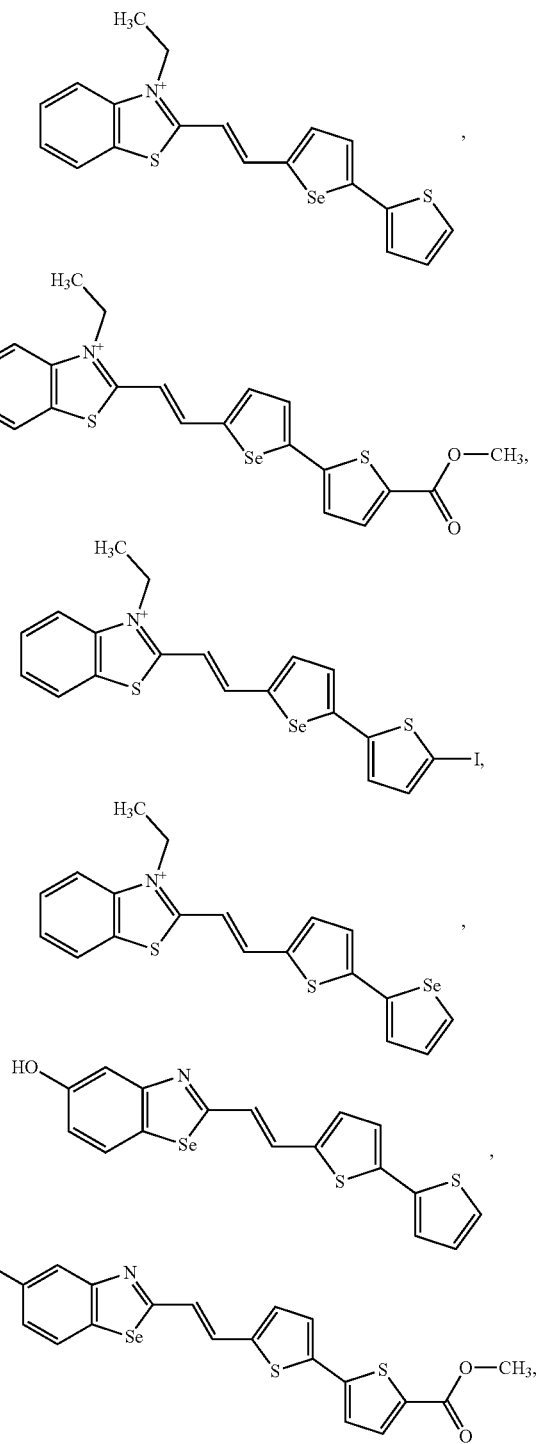

-continued

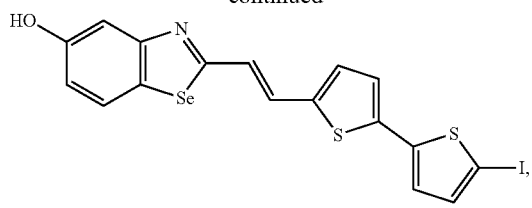

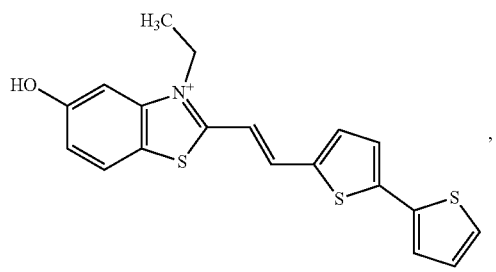 [SMILES: CC[n+]1c(/C=C/c2ccc(-c3cccs3)s2)sc2ccc(O)cc21 ; ","],

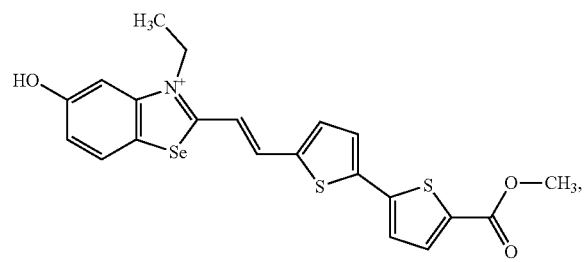,

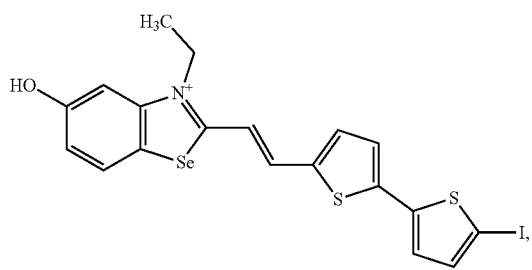,

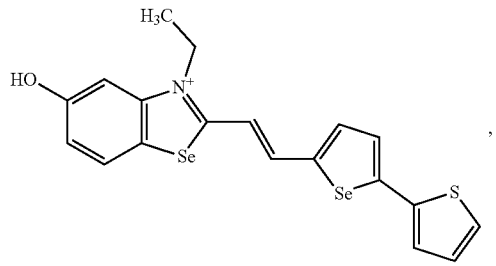,

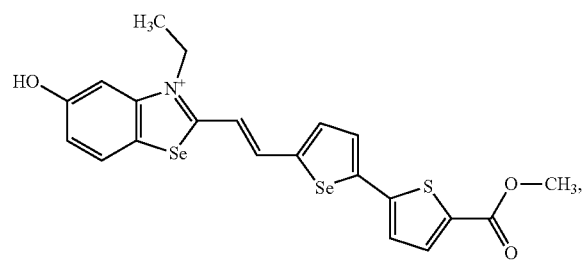

-continued

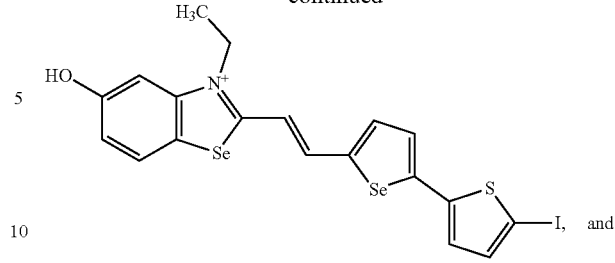, and

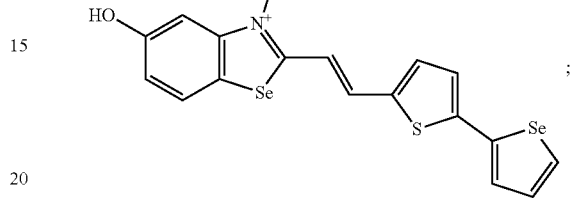;

or a pharmaceutically acceptable ester, amide, carbamate or salt thereof, including salts of such esters, amides or carbamates.

Depending upon the substituents present in compounds of the formula (I), the compounds may form esters, amides, carbamates and/or salts. Salts of compounds of formula (I) which are suitable for use in medicine are those wherein a counter-ion is pharmaceutically acceptable. However, salts having non-pharmaceutically acceptable counter-ions are within the scope of the present invention, for example, for use as intermediates in the preparation of the compounds of formula (I) and their pharmaceutically acceptable salts, and physiologically functional derivatives. By the term "physiologically functional derivative" is meant a chemical derivative of a compound of formula (I) having the same physiological function as the free compound of formula (I), for example, by being convertible in the body thereto. Esters, amides and carbamates are examples of physiologically functional derivatives.

Suitable salts according to the invention include those formed with organic or inorganic acids or bases. In particular, suitable salts formed with acids include those formed with mineral acids, strong organic carboxylic acids, such as alkanecarboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as ($C_1$-$C_4$)-alkyl- or aryl-sulfonic acids which are unsubstituted or substituted, for example by halogen. Pharmaceutically acceptable acid addition salts include those formed from hydrochloric, hydrobromic, hydroiodic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine. Other acids such as oxalic, while not in themselves pharmaceutically acceptable, may be useful as intermediates in obtaining the compounds of the invention and their pharmaceutical acceptable acid addition salts.

Compounds of the invention wherein X is $N^+$—$R^3$ are cationic, and exist in the form of a salt with a suitable anionic counter ion. Suitable anionic counter ions include, but are not limited to, iodide, bromide, chloride, tosylate, acetate, and triflate.

Compounds of formula (I) may have an appropriate group converted to an ester, an amide or a carbamate. Typical ester and amide and carbamate groups formed from an —OH or a basic nitrogen of an aromatic heterocycle in the compound of the formula (I) include —OC(O)$R^G$, >NC(O) $R^G$, >NCO$_2R^G$, —OSO$_2R^G$, and >NSO$_2R^G$, where $R^G$ is selected from the group consisting of $C_{1-8}$alkyl, $C_{2-8}$alkenyl, $C_{2-8}$alkynyl, $C_{3-8}$cycloalkyl and $C_{3-8}$cycloalkyl$C_{1-8}$alkyl, halo$C_{1-8}$alkyl, dihalo$C_{1-8}$alkyl, trihalo$C_{1-8}$alkyl, phenyl and phenyl$C_{1-4}$alkyl; more preferably $R^G$ is selected from the group consisting of $C_{1-6}$alkyl, $C_{2-6}$alkenyl, $C_{2-6}$alkynyl, $C_{3-8}$cycloalkyl and $C_{3-8}$cycloalkyl$C_{1-6}$alkyl.

Those skilled in the art of organic chemistry will appreciate that many organic compounds can form complexes with solvents in which they are reacted or from which they are precipitated or crystallized. These complexes are known as "solvates". For example, a complex with water is known as a hydrate. Solvates, such as hydrates, exist when the drug substance incorporates solvent, such as water, in the crystal lattice in either stoichiometric or non-stoichiometric amounts. Drug substances are routinely screened for the existence of hydrates since these may be encountered at any stage of the drug manufacturing process or upon storage of the drug substance or dosage form. Solvates are described in S. Byrn et al, Pharmaceutical Research 12(7), 1995, 954-954, and Water-Insoluble Drug Formulation, 2$^{nd}$ ed. R. Liu, CRC Press, page 553, which are incorporated herein by reference. Accordingly, it will be understood by the skilled person that the compounds of formula (I), as well as esters, amides, carbamates and/or salts thereof may therefore be present in the form of solvates. Solvates of compounds of formula (I) which are suitable for use in medicine are those wherein the associated solvent is pharmaceutically acceptable. For example, a hydrate is an example of a pharmaceutically acceptable solvate. However, solvates having non-pharmaceutically acceptable associated solvents may find use as intermediates in the preparation of the compounds of formula (I) and their pharmaceutically acceptable esters, amides, carbamates and/or salts thereof.

A compound which, upon administration to the recipient, is capable of being converted into a compound of formula (I) as described above, or an active metabolite or residue thereof, is known as a "prodrug". A prodrug may, for example, be converted within the body, e.g. by hydrolysis in the blood, into its active form that has medical effects. Pharmaceutical acceptable prodrugs are described in T. Higuchi and V. Stella, Prodrugs as Novel Delivery Systems, Vol. 14 of the A. C. S. Symposium Series (1976); "Design of Prodrugs" ed. H. Bundgaard, Elsevier, 1985; and in Edward B. Roche, ed., Bioreversible Carriers in Drug Design, American Pharmaceutical Association and Pergamon Press, 1987, which are incorporated herein by reference.

The following definitions apply to the terms as used throughout this specification, unless otherwise limited in specific instances.

As used herein, the term "alkyl" means both straight and branched chain saturated hydrocarbon groups. Examples of alkyl groups, and in particular examples of $C_{1-6}$alkyl groups, include methyl, ethyl, n-propyl, iso-propyl, n-butyl, t-butyl, i-butyl, sec-butyl, pentyl and hexyl groups. Among unbranched alkyl groups, these are preferably methyl, ethyl, n-propyl, n-butyl groups. Among branched alkyl groups, there may be mentioned isopropyl, tertbutyl, isobutyl, 1-ethylpropyl and 1-ethylbutyl groups.

As used herein, the term "haloalkyl" means an alkyl group having a halogen substituent, the term "alkyl" being understood to have the meanings outlined above. Similarly, the term "monohaloalkyl" means an alkyl group having one halogen substituent, the term "dihaloalkyl" means an alkyl group having two halogen substituents, and the term "trihaloalkyl" means an alkyl group having three halogen substituents. Examples of monohaloalkyl groups include fluoromethyl, chloromethyl, bromomethyl, fluoromethyl, fluoropropyl and fluorobutyl groups; examples of dihaloalkyl groups include difluoromethyl and difluoroethyl groups; examples of trihaloalkyl groups include trifluoromethyl and trifluoroethyl groups.

As used herein, the term "aromatic carbocycle" means an aromatic cyclic group of carbon atoms. A carbocycle group may, for example, be monocyclic or bicyclic. An example of a monocyclic aromatic carbocyclyl groups is phenyl; examples of a bicyclic aromatic carbocycle groups are naphthyl and indanyl. Aromatic carbocycle groups include bicyclic carbocycle groups in which one of the rings is non-aromatic.

As used herein, the term "aromatic heterocycle" means an aromatic cyclic group of carbon atoms wherein from one to three of the carbon atoms is/are replaced by one or more heteroatoms independently selected from nitrogen, oxygen, sulfur or selenium. A heterocycle group may, for example, be monocyclic or bicyclic. In a bicyclic heterocycle group there may be one or more heteroatoms in each ring, or only in one of the rings. A heteroatom may be S, O, N or Se, and is preferably S, O or N. Heterocyclyl groups containing a suitable nitrogen atom include the corresponding N-oxides. Aromatic heterocycle groups include bicyclic heterocycle groups in which one of the rings is non-aromatic.

Labelled Compounds of the Invention

Compounds of the invention may be labelled. A "label" (which may be a radiolabel or other detectable label, or a tag, marker, detectable marker, tracer, radiotracer or equivalent) is any atom or group suitable for imaging and/or assaying (for example, identifying, imaging, diagnosing, evaluating, detecting and/or quantitating) in vivo or in vitro, and in particular imaging and diagnosing. Suitable labels include, for example, radioisotopes, radionuclides, isotopes, positron emitters, gamma emitters, fluorescent groups, luminescent groups, chromogenic groups, biotin (in conjunction with streptavidin complexation) or photoaffinity groups. They type of label chosen will depend on the desired detection method. The position at which the label is integrated or attached to the compounds of the present invention is not particularly limited.

Examples of isotopes (such as radioisotopes, radionuclides, positron emitters and gamma emitters) which may be used to label compounds of the invention, include but are not limited to: $^2$H, $^3$H, $^{18}$F, $^{123}$I, $^{124}$I, $^{125}$I, $^{131}$I, $^{11}$C, $^{13}$N, $^{15}$O. and $^{77}$Br; preferably $^2$H, $^3$H, $^{11}$C, $^{13}$N, $^{15}$O, $^{18}$F, $^{120}$I, $^{123}$I and $^{125}$I; more preferably $^{11}$C, $^{13}$N, $^{15}$O, $^{18}$F, $^{120}$I, and $^{123}$I; and even more preferably $^{18}$F.

Isotopic variants of the compounds of the invention can generally be prepared by conventional procedures such as by the methods described in the Examples section using appropriate isotopic variations of suitable reagents, commercially available or prepared by known synthetic techniques. Radioisotopes, radionuclides, positron emitters and gamma emitters can be included into the compounds of the present invention by methods which are routine in the field of organic chemistry. For example, they may be introduced by using a correspondingly labeled starting material when the desired compound of the present invention is prepared. Illustrative methods of introducing detectable labels are described, for instance, in US 2012/0302755.

In certain preferred embodiments, compounds of the invention are labelled. In the compounds of the invention, one or more C, one or more N, one or more O, one or more F, and/or one or I may be replaced with a $^{11}$C, $^{13}$N, $^{15}$O, $_{18}$F and $^{120}$I, respectively. $^{11}$C, $^{13}$N, $^{15}$O, $^{18}$F and $^{120}$I are radioactive isotopes. They decay mainly by positron emission. Therefore, the inclusion of such atoms in a compound of the invention makes the compound detectable by positron emission tomography. As such compounds of the invention comprising one or more $^{11}$C, $^{13}$N, $^{15}$O, $^{18}$F and $^{120}$I are especially useful as a radioactive tracers, also referred to as a radioactive ligands, for positron emission tomography (PET).

In the compounds of the invention, one or more I may be replaced with an $^{123}$I radioactive isotope. The inclusion of such an atom in a compound of the invention makes the compound detectable by single-photon emission computed tomography (SPECT). As such compounds of the invention comprising one or more $^{123}$I are especially useful as a radioactive tracers for SPECT.

In the compounds of the invention, one or more H may be replaced with an $^{3}$H radioactive isotope. The inclusion of such an atom in a compound of the invention makes the compound detectable by autoradiography or liquid scintillation counting. Compounds of the invention comprising one or more $^{3}$H are especially useful as a radioactive tracers for in vitro studies.

In the compounds of the invention, one or more I may be replaced with an $^{125}$I radioactive isotope. The inclusion of such an atom in a compound of the invention makes the compound detectable by autoradiography, gamma-counter crystal detectors, scintigraphy, gamma imaging, and SPECT. Compounds of the invention comprising one or more $^{125}$I are especially useful as a radioactive tracers for in vitro studies and in vitro SPECT.

In certain preferred embodiments, labelled compounds of the invention may be labelled so that they may be detected in vivo using in vivo magnetic resonance spectroscopy (MRS), magnetic resonance imaging, PET, single-photon SPECT and combinations thereof. For example, a compound of the invention may be labeled with $^{19}$F or $^{13}$C for MRS/MRI; may be radiolabeled with $^{11}$C, $^{13}$N, $^{18}$F and $^{120}$I for PET imaging; or may be radiolabeled with $^{123}$I or $^{125}$I for SPECT.

Preferably the compounds of the invention comprise one or more radioisotopes selected from carbon-11 ($^{11}$C), nitrogen-13 ($^{13}$N), oxygen-15 ($^{15}$O), fluorine-18 ($^{18}$F) and iodine-120 ($^{120}$I). The compounds of the invention comprise a number of C atoms. One or more C in a compound of the invention may be replaced with a $^{11}$C. For example, one C is replaced with one $^{11}$C; or two C are replaced with two $^{11}$C; or three C are replaced with three$^{11}$ C. Preferably, one C is replaced with one $^{11}$C.

The compounds of the invention comprise one or more N. One or more N in a compound of the invention may be replaced with a $^{13}$N. For example, one N is replaced with a $^{13}$N; or (if present) two N are replaced with two $^{13}$N; or (if present) three N are replaced with three $^{13}$N. Preferably, if one at least one N is present in the compound of the invention, one N is replaced with a $^{13}$N.

For compounds of the invention comprising one or more O, one or more O in the compound may be replaced with an $^{15}$O. For example, (if present) one O is replaced with an $^{15}$O; or (if present) two O are replaced with two $^{15}$O; or (if present) three O are replaced with three $^{15}$O. Preferably, if one at least one O is present in the compound of the invention, one O is replaced with an $^{15}$O.

For compounds of the invention comprising one or more F, one or more F in the compound may be replaced with a $^{18}$F. For example, (if present) one F is replaced with a $^{18}$F; or (if present) two F are replaced with two $^{18}$F; or (if present) three F are replaced with three $^{18}$F. Preferably, if at least one F is present in the compound of the invention, one F is replaced with a $^{18}$F.

For compounds of the invention comprising one or more I, one or more I in the compound may be replaced with an $^{120}$I. For example, (if present) one I is replaced with an $^{120}$I; or (if present) two I are replaced with two $^{120}$I; or (if present) three I are replaced with three $^{120}$I. Preferably, if at least one I is present in the compound of the invention, one I is replaced with an $^{120}$I.

For compounds of the invention comprising one or more I, one or more I in the compound may alternatively be replaced with an $^{123}$I or $^{125}$I. For example, (if present) one I is replaced with an $^{123}$I or $^{125}$I; or (if present) two I are replaced with two an $^{123}$I or $^{125}$I; or (if present) three I are replaced with three an $^{123}$I or $^{125}$I. Preferably, if at least one I is present in the compound of the invention, one I is replaced with an $^{123}$I or $^{125}$I.

The compounds of the invention comprise a number of H atoms. One or more H in a compound of the invention may be replaced with a $^{3}$H. For example, one H is replaced with one $^{3}$H; or two H are replaced with two $^{3}$H; or three H are replaced with three $^{3}$H, or at least three H are replaced with at least three $^{3}$H.

Uses of Compounds of the Invention

The present invention provides compounds that are selective tau deposit/aggregate ligands. The terms "tau deposit ligand" and "tau aggregate ligand" as used herein is intended to cover any moiety which binds to a tau deposit (a tau deposit may also be referred to as a tau aggregate). For example, the compounds of the present invention may bind to one or more of: pathologically aggregated tau, hyperphosphorylated tau, neurofibrillary tangles, paired helical filaments, straight filaments, neurotoxic soluble oligomers, polymers and fibrils. The compounds of the present invention are particularly suitable for binding to various types of tau deposits (i.e. tau aggregates).

Preferred compounds of the present invention are selective tau deposit ligands. "Selective", in this context, means any tau deposit ligand that binds to a tau deposit in preference to an Aβ deposit. For example, the binding affinity for tau is at least 2 times that for Aβ, preferably at least 5 times, more preferably at least 10 times, more preferably at least 20 times, more preferably at least 50 times and even more preferably at least 100 times, for example at least 150 times, at least 200 times, at least 300 times, at least 500 times, or at least 1000 times. In one preferred embodiment, the binding affinity for tau is at least 50 times that for Aβ. In another preferred embodiment, the binding affinity for tau is at least 100 times that for Aβ.

The compounds of the present invention find utility in the diagnosis and/or the treatment or prophylaxis of conditions associated with tau deposits. For example, the compounds of the present invention find utility in the diagnosis and/or treatment or prophylaxis of tauopathies, for example: Alzheimer's disease, corticobasal degeneration, Pick's disease, progressive supranuclear palsy, Parkinson's disease, Creutzfeldt-Jacob disease, familial Alzheimer's disease, tangle predominant senile dementia, argyrophilic grain disease, prion protein cerebral amyloid angiopathy, traumatic brain injury, amyotrophic lateral sclerosis, frontotemporal dementia and Parkinsonism linked to chromosome 17, postencephalitic Parkinsonism, Guadeloupean parkinsonism, globular glial tauopathies, ageing-related tau astrogliopathy, Parkinsonismdementia complex of Guam, Niemann-Pick disease type C, myotonic dystrophy, inclusion-body myositis, chronic traumatic encephalopathy, Down's syndrome, Gerstman-Sträussler-Scheinker syndrome, British dementia, familial Danish dementia, dementia pugiiistica, Huntington's disease, Lewy body disorders, Prion disease, subacute sclerosing panencephalitis, subacute sclerosing panencephalitis, diffuse neurofibrillary tangles with calcification, neurodegeneration with brain iron accumulation, mutation affecting the sodium/proton exchanger, cerebrotendinous xanthomatosis with the c.379C>T (p.R127W) mutation in the CYP27A1 gene, TARDBP mutation p.lle383Val associated with semantic dementia, non-Guamanian motor neuron disease with neurofibrillary tangles, argyrophilic grain disease, Hallervorden-Spatz disease, multiple system atrophy, pallido-ponto-nlgral degeneration, progressive subcortical gliosis, tangle only dementia, myotonic dystrophy, tau panencephalopathy, AD-like with astrocytes, Gerstmann-Sträussler-Scheinker with tau, mutations in LRRK2, SLC9A6-related mental retardation, and white matter tauopathy with globular glial inclusions. The compounds of the present invention are especially useful in the diagnosis and/or treatment (in particular diagnosis) of Alzheimer's disease, Corticobasal Degeneration, Pick's disease, Parkinson's disease, chronic traumatic encephalopathy and progressive supranuclear palsy; and even more especially Alzheimer's disease and Corticobasal Degeneration.

As such, the compound of the invention may be for use as a therapeutic agent (or medicament) in the treatment of a disease or disorder associated with tau deposits (i.e. tauopathies), such as the tauopathies listed above.

The invention also provides a method for the treatment or prophylaxis of a condition associated with a disease or disorder associated with tau deposits (i.e. tauopathies) in a mammal (in particular in a human), which comprises administering to the mammal a therapeutically effective amount of a compound according to the invention, or a composition comprising a compound according to the invention together with a pharmaceutically acceptable carrier. Clinical conditions mediated by tau deposits that may be treated by the method of the invention are tauopathies, for example the tauopathies listed above.

The invention also provides the use of a compound according to the invention, for the manufacture of a medicament for the treatment or prophylaxis of a condition associated with a disease or disorder associated with tau deposits (i.e. tauopathies), for example the tauopathies listed above.

The compound of the invention may be for use as a diagnostic agent (for in vivo and/or in vitro diagnostic use) for the detection of tau deposits, and preferably for the selective detection of tau deposits.

The compound of the invention may be used for diagnostic purposes because it has the ability to target a desired pathology (tau deposits) and the compound can be detected at the desired site. The compounds of the invention are especially useful because they selectively bind to tau deposits over Aβ deposits. This makes the compounds of the invention especially useful for diagnosis of tauopathies, such as the tauopathies listed above, and in particular Alzheimer's disease and corticobasal degeneration. For example, compounds of the invention are able to detect the presence and the level of tau deposits in a patient with or suspected of having a tauopathy, such as Alzheimer's disease or corticobasal degeneration.

The compounds of the invention can bind tau deposits both in vivo and in vitro. The compound of the invention may be for use as a diagnostic agent (for in vivo and/or in vitro diagnostic use) in the diagnosis of disease or disorder associated with tau deposits (i.e. tauopathies), such as the tauopathies listed above.

When used as a diagnostic agent, the compounds of the invention may be detected by fluorescence spectroscopy. As such, the compounds of the invention may be used for fluorescence imaging, and more specifically fluorescence imaging of protein aggregates, and in particular of tau aggregates (tau aggregates may also be referred to as tau deposits).

When used as a diagnostic agent, the compounds of the invention may optionally be in labelled form, as described above. Thus the present invention also provides the use of a compound of the invention in a labelled form for use as a diagnostic agent for the diagnosis of conditions associated with a disease or disorder associated with tau deposits (i.e. a tauopathy). In such embodiments, preferably the compound of the invention in labelled form comprises one or more radioisotopes selected from $^{3}H$, $^{11}C$, $^{13}N$, $^{15}O$, $^{18}F$, $^{120}I$, $^{123}I$, and $^{125}I$. When used as a diagnostic agent (especially for in vivo use), and the compound is radioactively labelled, for example with $^{11}C$, $^{13}N$, $^{15}O$, $^{18}F$, or $^{120}I$, the compounds of the invention may be detected by positron emission topography. When used as a diagnostic agent (especially for in vivo use), and the compound is radioactively labelled, for example with $^{123}I$ or $^{125}I$, the compounds of the invention may be detected by SPECT. When used as a diagnostic agent (especially for in vitro use), and the compound is radioactively labelled, for example with $^{3}H$ or $^{125}I$, the compounds of the invention may be detected by autoradiography.

As mentioned above, a compound of the invention may be used for diagnostic purposes because it has the ability to target a desired pathology (tau deposits) and the compound can be detected at the desired site. As such, the compounds of the invention when used as diagnosis agents are especially useful as imaging agents. Imaging agents are compounds that allow the imaging of specific organs, tissues, diseases and physiological functions. Such imaging allows for diagnosing disease, monitoring disease progression, and tracking therapeutic response.

A compound of the invention when used as a diagnostic agent, and in particular as an imaging agent, may be detected via radioscintigraphy, assays, chemilumensence, electrochemiluminescence, near infrared luminescence, fluorescence, spectroscopy, autoradiography, liquid scintillation counting, gamma imaging, magnetic resonance imaging (MRI), magnetic resonance spectroscopy (MRS), fluorescence spectroscopy, scintigraphy, single-photon emission computed tomography (SPECT), computed tomography (CT scan), and/or positron emission tomography (PET).

In embodiments of the invention wherein the compound of the invention is for use as a diagnostic agent, and in particular as an imaging agent, the type of detection instrument available is a major factor in selecting if a label is required, and what label to choose. For example, where imaging requires an isotope to be detected, the type of detection instrument used will guide if a label is needed (i.e. is the isotope naturally occurring or not, and at what abundance is it present in when it occurs naturally), and, if so, what isotope to use. In one aspect, the compound of the invention is labelled, and the form of labelling chosen must have a type of decay detectable by a given type of instrument. Moreover, other considerations such as the half-life of the radioisotopes are taken into account when selecting an isotope label for in vivo imaging.

The compounds of the invention for use as diagnostic agents for in vivo imaging (in particular imaging of tau deposits and/or quantification of tau deposits) are preferably used in conjunction with non-invasive neuroimaging techniques such as in vivo MRS, MRI, PET, SPECT and combinations thereof. A compound of the invention may be labeled with $^{11}$C, $^{13}$N, $^{15}$O, $^{18}$F, or $^{120}$I for PET imaging; or may be radiolabeled with $^{123}$I (or $^{125}$I) for SPECT imaging. No labelling may be required for in vivo MRS or MRI, or a compound may be labelled with $^{13}$C for MRS or MRI.

The present invention also provides method of diagnosing a patient or monitoring disease progression in a patient comprising administering a compound of the invention to the patient. The method may further comprise detecting the compound of the invention in vivo at the site of interest in a patient (e.g. the brain) using PET or SPECT, or detecting the compound in a sample from the patient. Preferably in such embodiments the compound of the invention comprises one or more radioisotopes selected from $^{11}$C, $^{13}$N, $^{15}$O, $^{18}$F, and $^{120}$I. Alternatively, the method of diagnosis may further comprise detecting the compound of the invention using fluorescence spectroscopy. The present invention also provides method of diagnosing a patient or monitoring disease progression in a patient comprising contacting a compound of the invention with a sample taken from the patient.

Alternatively, the method may further comprise detecting the compound of the invention using radioscintigraphy, assays, chemilumensence, electrochemiluminescence, autoradiography, near infrared luminescence, fluorescence, spectroscopy, liquid scintillation counting, gamma imaging, scintigraphy, magnetic resonance imaging (MRI), magnetic resonance spectroscopy (MRS), single-photon emission computed tomography (SPECT), or computed tomography (CT scan).

In the methods of diagnosing a disease or disorder associated with tau deposits as described herein, the method may comprise:
i) administering to the subject a diagnostically effective amount of a compound of the invention;
ii) allowing the compound of the invention to distribute into the tissue of interest (such as brain or body fluids such as cerebrospinal fluid (CSF)): and
iii) imaging the tissue of interest, wherein an increase in binding of the compound of the invention to the tissue of interest compared to a normal or control level of binding indicates that the subject is suffering from or is at risk of developing a disorder associated with tau deposits.

The compounds of the present invention can be used for imaging tau deposits in any sample or a specific body part or body area of a patient which suspected to contain tau deposits.

The compounds of the present invention are particularly suitable for imaging of tau deposits in the brain, as well as in body fluids such as cerebrospinal fluid (CSF).

Diagnosis of a disease or disorder associated with tau deposits in a patient may be achieved by detecting the specific binding of a compound according to the invention to the tau deposits in a sample or in situ, which includes:

(a) bringing the sample or a specific body part or body area suspected to contain the tau deposits into contact with a compound of the invention which binds the tau deposits.
(b) allowing the compound of the invention to bind to the tau deposits to form a compound/tau deposits complex,
(c) detecting the formation of the compound/tau deposits complex,
(d) optionally correlating the presence or absence of the compound/tau deposits complex with the presence or absence of tau deposits in the sample or specific body part or area, and
(e) optionally comparing the amount of the compound/tau deposits complex to a normal or control value, wherein an increase in the amount of the compound/tau deposits complex compared to a normal control value may indicate that the patient is suffering from or is at risk of developing a tau-associated disorder.

After the sample or a specific body part or body area has been brought into contact with the compound of the present invention, the compound is allowed to bind to the tau deposits. The amount of time required for binding will depend on the type of test (e.g. in vitro or in vivo) and can be determined by a person skilled in the art by routine experiments.

The presence or absence of the compound/tau deposits is then optionally correlated with the presence or absence of tau deposits in the sample or specific body part or area. Finally, the amount of the compound/tau deposits complex can be compared to a normal or control value which has been determined in a sample or a specific body part or body area of a healthy subject, wherein an increase in the amount of the compound/tau deposits complex compared to a normal or control value may indicate that the patient is suffering from or is at risk of developing a disease or disorder associated with tau deposits (i.e. a tauopathy). The present invention also relates to a method of determining the amount of tau deposits in a tissue and/or a body fluid. This method comprises the steps of:
(1) providing a sample representative of the tissue and/or body fluid under Investigation;
(2) testing the sample for the presence of tau deposits with a compound of the present invention;
(3) determining the amount of compound bound to the tau deposits; and
(4) calculating the amount of tau deposits in the tissue and/or body fluid.

The sample can be tested for the presence of tau deposits with a compound of the present invention by bringing the sample into contact with a compound of the invention, allowing the compound of the invention to bind to the tau deposits to form a compound/tau deposit complex and detecting the formation of the compound/tau deposit as explained above.

Monitoring minimal residual disorder in a patient suffering from a disorder associated with tau deposits who has been treated with a therapeutic agent useful in the prevention or treatment of a disorder associated with tau deposits (for example a therapeutic agent useful in the prevention or treatment of one or more or the tauopathies listed abov) may be achieved by:
carrying out steps (a) to (d) above; and (e) optionally comparing the amount of the compound/tau deposit complex to a normal or control value, wherein an increase in the amount of the complex compared to a normal or control value may indicate that the patient may still suffer from a minimal residual disease.

How steps (a) to (e) can be conducted has already been explained above.

Predicting responsiveness of a patient suffering from a disorder associated with tau deposits and being treated with a therapeutic agent useful in the prevention or treatment of a disorder associated with tau deposits can be achieved by carrying out steps (a) to (d) above; and (e) optionally comparing the amount of the compound/tau deposit complex to a normal or control value.

How steps (a) to (e) can be conducted has already been explained above.

In the method for predicting responsiveness the amount of the compound/tau deposits complex can be optionally compared at various points of time during the treatment, for instance, before and after onset of the treatment or at various points of time after the onset of the treatment. A change, especially a decrease, in the amount of the compound/tau deposits complex may indicate that the patient has a high potential of being responsive to the respective treatment.

A compound according to the present invention can also be incorporated into a test kit for detecting tau deposits. The test kit typically comprises a container holding one or more compounds according to the present Invention and instructions for using the compound for the purpose of binding to tau deposits to form a compound/tau deposit complex and detecting the formation of the compound/tau deposit complex such that presence or absence of the compound/tau deposit complex correlates with the presence or absence of the tau deposits.

Dosing

The amount of compound of the invention which is required to achieve a diagnostic or therapeutic effect will, of course, vary with the particular compound, the route of administration, the subject under treatment, including the type, species, age, weight, sex, and medical condition of the subject and the renal and hepatic function of the subject, and the particular disorder or disease being treated, as well as its severity. An ordinarily skilled physician, veterinarian or clinician can readily determine and prescribe the effective amount of the drug required to prevent, counter or arrest the progress of the condition or be used to diagnose a condition or the progression of a condition.

Oral dosages of the present invention, when used for as a diagnostic of therapeutic agent, will range between about 0.01 mg per kg of body weight per day (mg/kg/day) to about 100 mg/kg/day, preferably 0.01 mg per kg of body weight per day (mg/kg/day) to 10 mg/kg/day, and most preferably 0.1 to 5.0 mg/kg/day, for adult humans. For oral administration, the compositions are preferably provided in the form of tablets or other forms of presentation provided in discrete units containing 0.01, 0.05, 0.1, 0.5, 1.0, 2.5, 5.0, 10.0, 15.0, 25.0, 50.0, 100, and 500 milligrams of the compound of the invention for the symptomatic adjustment of the dosage to the patient to be treated. A medicament typically contains from about 0.01 mg to about 500 mg of the compound of the invention, preferably from about 1 mg to about 100 mg of compound of the invention. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. For diagnostic use, preferably the compounds of the present invention may be administered in a single daily dose. Furthermore, preferred compounds for the present invention can be administered in intranasal form via topical use of suitable intranasal vehicles, or via transdermal routes, using those forms of transdermal skin patches well known to those of ordinary skill in the art.

While it is possible for the compound of the invention to be administered alone, it is preferable for it to be present in a pharmaceutical formulation or composition. Accordingly, the invention provides a pharmaceutical formulation or composition comprising a compound according to the invention, and a pharmaceutically acceptable diluent, excipient or carrier. Pharmaceutical compositions of the invention may take the form of a pharmaceutical formulation as described below.

Formulations

"Pharmaceutical" as used here does not necessarily mean therapeutic, for example, a pharmaceutical formulation may be used as a diagnostic agent or imaging agent. The pharmaceutical formulations according to the invention include those suitable for oral, parenteral (including subcutaneous, intradermal, intramuscular, intravenous [bolus or infusion], and intraarticular), inhalation (including fine particle dusts or mists which may be generated by means of various types of metered dose pressurized aerosols), nebulizers or insufflators, rectal, intraperitoneal and topical (including dermal, buccal, sublingual, and intraocular) administration, although the most suitable route may depend upon, for example, the condition and disorder of the recipient to be treated or diagnosed.

The formulations may conveniently be presented in unit dosage form and may be prepared by any of the methods well known in the art of pharmacy. All methods include the step of bringing the compound of the invention into association with the carrier which constitutes one or more accessory ingredients. In general the formulations are prepared by uniformly and intimately bringing into association the compound of the invention with liquid carriers or finely divided solid carriers or both and then, if necessary, shaping the product into the desired formulation.

Formulations of the present invention suitable for oral administration may be presented as discrete units such as capsules, cachets, pills or tablets each containing a predetermined amount of the compound of the invention; as a powder or granules; as a solution or a suspension in an aqueous liquid or a non-aqueous liquid, for example as elixirs, tinctures, suspensions or syrups; or as an oil-in-water liquid emulsion or a water-in-oil liquid emulsion. The compound of the invention may also be presented as a bolus, electuary or paste.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for nasal, aerosol or inhalation administration include solutions in saline, which can contain, for example, benzyl alcohol or other suitable preservatives, absorption promoters to enhance bioavailability, and/or other solubilizing or dispersing agents such as those known in the art.

Formulations for topical administration in the mouth, for example buccally or sublingually, include lozenges comprising the compound of the invention in a flavoured basis such as sucrose and acacia or tragacanth, and pastilles comprising the compound of the invention in a basis such as gelatin and glycerine or sucrose and acacia. Exemplary compositions for topical administration include a topical carrier such as Plastibase (mineral oil gelled with polyethylene).

Preferred unit dosage formulations are those containing an effective dose, as hereinbefore recited, or an appropriate fraction thereof, of the compound of the invention. It should be understood that in addition to the ingredients particularly mentioned above, the formulations of this invention may include other agents conventional in the art having regard to the type of formulation in question, for example those suitable for oral administration may include flavouring agents.

Whilst a compound of the invention may be used as the sole active ingredient (i.e. sole therapeutic agent or sole diagnostic agent) in a medicament, it is also possible for the compound to be used in combination with one or more further active ingredient. For example, a compound of the invention may be used as the sole diagnostic agent in a diagnostic composition, or it is also possible for the compound to be used in combination with one or more further diagnostic agents and/or one or more therapeutic agents. Alternatively, a compound of the invention may be used as the sole therapeutic agent in a medicament, or it is also possible for the compound to be used in combination with one or more further therapeutic agents and/or one or more diagnostic agents.

Thus, the invention also provides a compound according to the invention together with a further diagnostic agent, for simultaneous, sequential or separate administration. Such further diagnostic agents may be further compounds according to the invention, or they may be different diagnostic agents. The further diagnostic agent may be an agent useful in the diagnosis of tauopathies (for example the tauopathies listed above).

In certain preferred embodiments, the further diagnostic agent may be an agent that is selective for Aβ deposits useful in diagnosis of Alzheimer's disease. The further diagnostic agent may be detectable by radioscintigraphy, magnetic resonance imaging (MRI), assays, chemilumensence, near infrared luminescence, fluorescence, autoradiography, liquid scintillation counting, gamma imaging, scintigraphy, magnetic resonance imaging, magnetic resonance spectroscopy, fluorescence spectroscopy, SPECT, computed tomography (CT scan) and/or positron emission tomography (PET). Preferably, the further diagnostic agent is detectable by positron emission tomography. For example, the further agent may be a PET ligand.

For example, the compounds of the invention may be effectively administered in combination with (or may be used in vitro for in vitro diagnosis with) effective amounts of one or more other diagnostic agents such as luminescent conjugated oligothiophenes (e.g. q-FTAA-CN, p-FTAA-CN, h-FTAA-CN), Pittsburgh compound B (PiB), fludeoxyglucose F 18 (FDG), florbetapir, flutemetamol, NAV4694, PBB3, AT-100, 4G8, Congo red, Thioflavin S, Thioflavin T, m-l-stilbene, chrysamine G, BF-277, TZDM, FDDNP, MeO-X-04, IMPY, NIAD-4 $^3$H-X-34, luminescent conjugated polythiophenes (e.g. polythiophene acetic acid (PTAA), tPTAA, POWT, tPOWT, POMT, tPOMY) and GTP1 (Genentech Tau Probe 1).

The invention further provides a compound according to the invention together with a further therapeutic agent, for simultaneous, sequential or separate administration. Such further therapeutic agents may be further compounds according to the invention, or they may be different therapeutic agents, for example an agent useful in the prevention or treatment of one or more or the tauopathies listed above.

For example, the compounds of the instant invention may be effectively administered in combination with effective amounts of other agents such as antibodies (for example active immunisation (e.g. ACI-35 (AC Immune/Janssen), and AADvac1 (Axon Neuroscience)), passive immunization (e.g. tau antibodies, such as BMS-986168 (IPN007, Bristol-Myers Squibb Company), C2N-8E12 (C2N/AbbVie), and RG6100 (RO7105705, AC Immune/Genentech; aducanumab; solanezumab; gantenerumab; and crenezumab), RG7345 (RO6926496, MAb86, F. Hoffmann-La Roche), PHF1, 4E6G7, 6B2G12), MK-8719 (Merck & Co.), TPI-287 (Cortice Biosciences), methylene blue (for example TRx 0327 and Rember), dopaminergic treatments (for example levodopa, caridopa, dopamine agonists (e.g. bromocriptine, perfolide, pramipexole, ropinirole)), cholinesterase inhibitors (e.g. tacrine, donepezil, rivastigmine, galantamine), monoamine oxidase inhibitors (e.g. selegiline), antocholinerginc agents (e.g. trihexyphenidyl, benztropine mesylate, biperiden, procyclidine), antihistamine (e.g. diphenhydramine), antipsychotic drugs, analgesic drugs, anti-inflammatories, riluzole, non-steroidal anti-inflammatory drugs, caffein A2A receptor antagonists, CERE-120 (adeno-associated virus serotype 2-neurturin), amantadine, tolcapone, entacapone, ethosuximide, trazodone, and dibenzoylmethane.

The above other diagnostic and therapeutic agents, when employed in combination with the compounds of the present invention, may be used, for example, in those amounts indicated in the Physicians' Desk Reference (PDR) or as otherwise determined by one of ordinary skill in the art.

The compounds of the invention as described above, optionally in labelled form, also find use as a reference compound in methods of identifying ligands for the tau deposits. Thus, the invention provides a method of identifying a ligand for tau deposits which comprises use of a compound of the invention or a compound of the invention in labelled form, as a reference compound. For example, such a method may involve a competitive binding experiment in which binding of a compound of the invention to the tau deposits is reduced by the presence of a further compound which has tau deposits-binding characteristics, for example stronger tau deposits-binding characteristics than the compound of the invention in question.

In another aspect, the present invention provides a compound selected from the group consisting of:

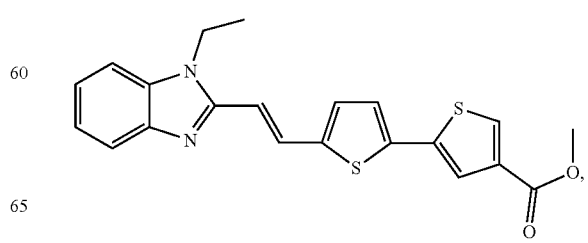

-continued

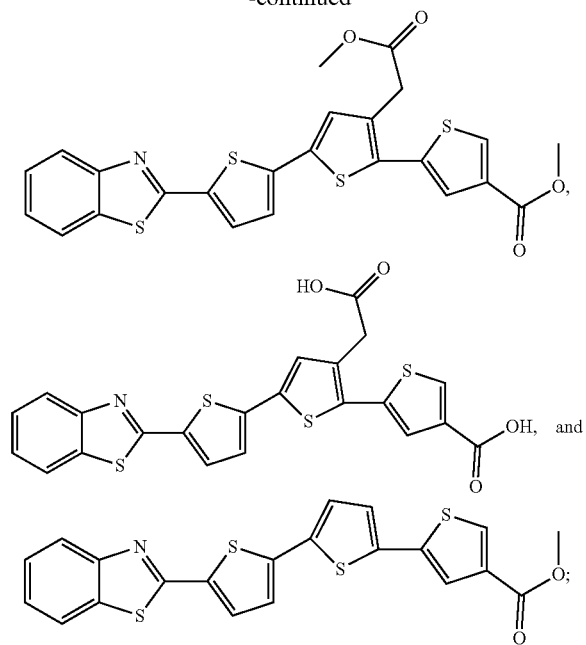

or a pharmaceutically acceptable salt thereof (or where applicable an ester, amide or carbamate thereof or a salt of such an ester, amide or carbamate. These compound are Comparative Examples 1, 2, 3 and 4, below. Although not selective for tau deposits, these compound have other advantageous properties. All aspects of the first invention (i.e. the compound of formula (I)) apply to the compounds of this aspect of the invention.

Experimental
Synthesis of Compounds of the Invention
General Information

All reagents and solvents were purchased from commercial sources and used as received without further purification unless indicated otherwise. NMR spectra were recorded on a Varian 300 instrument (Varian Inc., Santa Clara, Calif., USA) operating at 300 MHz for $^1$H and 75.4 MHz for $^{13}$C, using the residual solvent signal as reference. The IR spectra were performed on an Avatar 330 FT-IR spectrometer (Thermo Nicolet). TLC was carried out on Merck pre coated 60 F254 aluminum plates using UV-light ($\lambda$=254 nm and 366 nm) for visualization. MALDI-TOF spectra were recorded on a Voyager-DE STR Biospectrometry Workstation using α-cyano-4-hydroxycinnamic acid as a matrix and reference.

General Procedure for Condensation Reactions of 3-alkyl-2-methylbenzothiazolium Salts (G1): A few drops of pyridine were added to a cold solution of the aromatic aldehydes 2a-p (1 equiv) and the corresponding 2-methyl-3-alkylbenzothiazolium salt 1a-f (1 equiv.) in anhydrous MeOH/THF (15 mL/mmol) (structures of compounds 2a-p and 1a-f shown below; compounds 2a-p and 1a-f were purchased from commercial sources and used as received without further purification). The mixture was refluxed until it reached completion (monitored by TLC, eluent: DCM/MeOH 1%). The reaction mixture was evaporated in vacuo to provide a dark red solid residue, which was crystallized from appropriate solvent or purified by column chromatography on silica gel. The red crystals was collected, washed with cold MeOH and dried in vacuum to afford 3a-u in good purity and yield (structures of compounds 3a-u shown below).

General Procedure for Condensation Reactions of 2-methylbenzothiazole or 2-methylbenzoxazole (G2): To a solution of the 5-Bromo-2-thiophenecarboxaldehyde (4) (1 equiv.) and 2-methylbenzothiazole/oxazole 5a or 5b (1.1 equiv.) in DMSO was added a few drops of aqueous solution of KOH (1M) (structures of compounds 5a and 5b shown below; compounds 5a and 5b were purchased from commercial sources and used as received without further purification). The resulting mixture was stirred at room temperature and monitored by TLC until completion, thereafter water was added and the mixture neutralized with HCl (2M). The product was extracted with EtOAc (3×30 mL/mmol) and the combined organic phase was washed with water, brine, dried over MgSO$_4$ and concentrated in vacuo. The residue was purified by column chromatography on silica gel (eluent: n-heptane/EtOAc) to give the products 6a and 6b (structures of compounds 6a and 6b shown below).

General procedure for Suzuki coupling (G3): A mixture of stilbenes, the desired boronic pinacol esters 7a-d, K$_2$CO$_3$ (3 equiv./bromine, in 1,4-dioxane/methanol (8: 2, 8 mL/mmol, degassed)) and PEPPS-IPr (5 mol %) was heated to 80° C. for 20 min. After cooling to room temperature the pH was adjusted to pH 4 by addition of 1 M HCl, and the residue was extracted with DCM (3×30 mL/mmol), washed with water (3×30 mL/mmol) and brine (30 mL). The combined organic phase was dried over MgSO$_4$ and solvent evaporated. The crude product was either subjected to column chromatography or treated with appropriate solvent to give desired products 8a-e (structures of compounds 8a-e shown below).

(G1) Procedure:

Structures of Starting Materials 1a-f and 2a-p

| Starting Materials 1a-f |
|---|
| 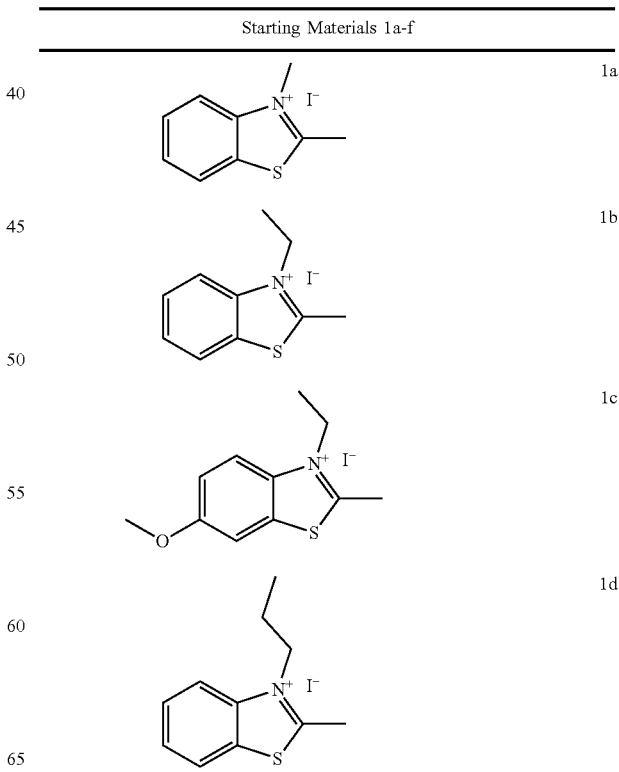 |

| | |
|---|---|
| 1e | |
| 1f | |
| Starting Materials 2a-p | |
| 2a | 2i |
| 2b | 2j |
| 2c | 2k |
| 2d | 2l |
| 2e | 2m |
| 2f | 2n |
| 2g | 2o |
| 2h | 2p |

Compounds of the Invention:
Example Compound 3a

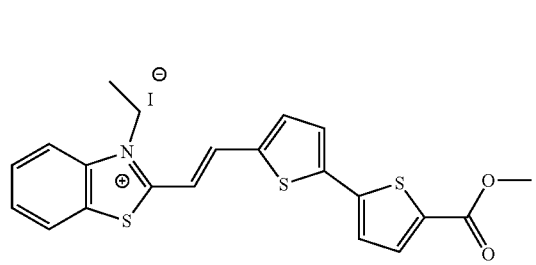

General procedure of condensation reactions (G1) was applied with 1b and 2a. The residue was purified by crystallization from MeOH to give stilbene 3a. $^1$H NMR (300 MHz, DMSO-d6) δ8.50-8.42 (m, 2H), 8.29 (d, J=8.2 Hz, 1H), 8.00 (d, J=4.2 Hz, 1H), 7.93-7.71 (m, 5H), 7.62 (d, J=4.2 Hz, 1H), 4.94 (q, J=7.2 Hz, 2H), 3.86 (s, 3H), 1.47 (t, J=7.2 Hz, 3H). $^{13}$C NMR (75 MHz, DMSO-d6) δ170.6, 161.4, 142.0, 141.9, 140.9, 140.6, 139.4, 136.5, 135.0, 132.5, 129.6, 128.4, 128.3, 127.9, 126.7, 124.4, 116.6, 112.1, 52.51, 44.4, 14.2. MALDI-TOF: m/z calcd for $C_{21}H_{18}NO_2S_3$ (M+H)$^+$: 413.0. Found: 413.0.

Example Compound 3b

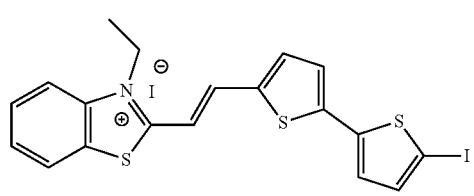

General procedure of condensation reactions (G1) was applied with 1b and 2b. The residue was purified by crystallization from MeOH/THF (1:1) to give stilbene 3b. $^1$H NMR (300 MHz, DMSO-d6) δ8.46-8.37 (m, 2H), 8.25 (d, J=8.3 Hz, 1H), 7.92 (d, J=4.2 Hz, 1H), 7.88-7.72 (m, 2H), 7.67 (d, J=15.4 Hz, 1H), 7.53 (d, J=4.0 Hz, 1H), 7.42 (d, J=3.8 Hz, 1H), 7.27 (d, J=3.8 Hz, 1H), 4.90 (q, J=7.1 Hz, 2H), 1.44 (t, J=7.1 Hz, 3H). MALDI-TOF: m/z calcd for $C_{19}H_{15}INS_3$ (M+H)$^+$: 481.0. Found: 481.0.

Example Compound 3c

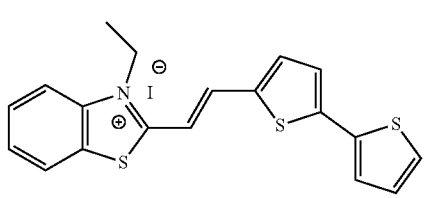

General procedure of condensation reactions (G1) was applied with 1b and 2c. The residue was purified by crystallization from MeOH to give stilbene 3c. $^1$H NMR (300 MHz, DMSO-d6)) δ8.50-8.35 (m, 1H), 8.25 (d, J=8.3 Hz, 1H), 7.93 (d, J=4.1 Hz, 1H), 7.88-7.61 (m, 2H), 7.59-7.50 (m, 1H), 7.19 (dd, J=5.1, 3.7 Hz, 1H), 4.90 (q, J=7.1 Hz, 1H), 1.44 (t, J=7.1 Hz, 1H). $^{13}$C NMR (75 MHz, DMSO) δ170.7, 144.4, 141.2, 140.9, 137.6, 137.3, 135.5, 129.5, 129.0, 128.2, 128.1, 126.4, 125.8, 124.4, 116.4, 110.8, 44.3, 14.1. MALDI-TOF: m/z calcd for $C_{19}H_{16}NS_3$ (M+H)$^+$: 355.0. Found: 355.0.

Example Compound 3d

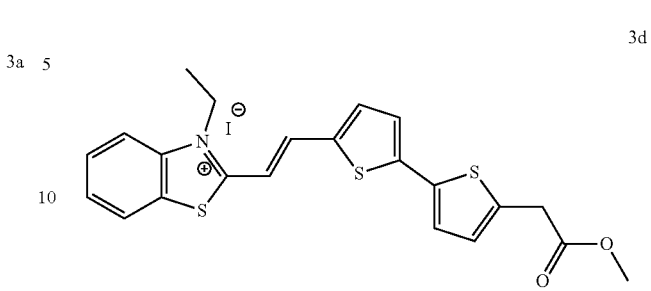

General procedure of condensation reactions (G1) was applied with 1b and 2d. The residue was purified by column chromatography using [DCM/MeOH (145%)]. This compound was dissolved in a mixture of 1,4-dioxane/water (7:3) and the solution was lyophilized to give stilbene 3d. $^1$H NMR (300 MHz, DMSO-d6) δ8.46-8.37 (m, 2H), 8.24 (d, J=8.3 Hz, 1H), 7.92 (d, J=4.2 Hz, 1H), 7.88-7.71 (m, 2H), 7.64 (d, J=15.4 Hz, 1H), 7.51 (d, J=4.0 Hz, 1H), 7.41 (d, J=3.6 Hz, 1H), 7.03 (d, J=3.7 Hz, 1H), 4.90 (q, J=7.2 Hz, 2H), 4.01 (s, 2H), 3.66 (s, 3H), 1.44 (t, J=7.2 Hz, 3H). $^{13}$C NMR (75 MHz, DMSO-d6) δ170.6, 170.3, 144.4, 141.2, 140.9, 137.9, 137.5, 137.3, 134.9, 129.4, 129.0, 128.2, 128.1, 126.0, 125.6, 124.4, 116.4, 110.7, 52.1, 44.3, 34.6, 14.1. MALDI-TOF: m/z calcd for $C_{22}H_{20}NO_2S_3$ (M+H)$^+$: 427.1. Found: 427.0.

Example Compound 3e

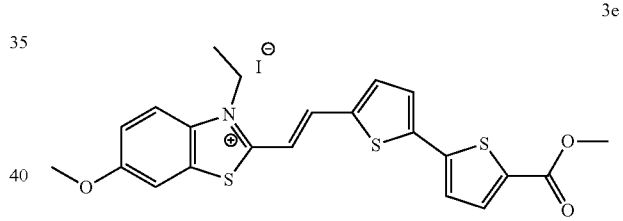

General procedure of condensation reactions (G1) was applied with 1c and 2a. The residue was purified by crystallization from MeOH/THF (1:1) to give stilbene 3e. $^1$H NMR (300 MHz, DMSO-d6) δ8.38 (d, J=15.5 Hz, 1H), 8.28 (d, J=9.0 Hz, 1H), 7.95 (d, J=4.1 Hz, 1H), 7.81 (d, J=4.0 Hz, 1H), 7.72 (m, 3H), 7.59 (d, J=4.0 Hz, 1H), 7.40 (dd, J=9.0, 2.3 Hz, 1H), 4.91 (q, J=7.0 Hz, 2H), 3.95 (s, 3H), 3.84 (s, 3H), 1.44 (t, J=7.0 Hz, 3H). $^{13}$C NMR (75 MHz, dmso) δ170.7, 161.4, 161.0, 142.5, 141.9, 141.6, 139.5, 139.5, 136.2, 135.0, 132.4, 127.9, 126.6, 125.1, 120.1, 118.0, 112.3, 99.8, 56.5, 52.6, 44.3, 14.1. MALDI-TOF: m/z calcd for $C_{22}H_{20}NO_3S_3$ (M+H)$^+$: 443.1. Found: 443.3.

Example Compound 3f

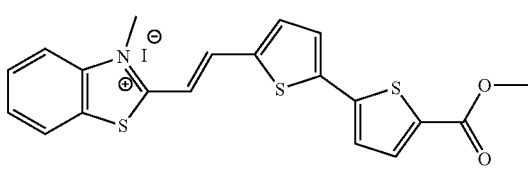

General procedure of condensation reactions (G1) was applied with 1a and 2a. The residue was purified by crystallization from MeOH to give stilbene 3f. $^1$H NMR (300 MHz, DMSO-d6) δ8.48-8.36 (m, 2H), 8.22 (d, J=8.2 Hz, 1H), 7.99-7.67 (m, 6H), 7.59 (d, J=4.0 Hz, 1H), 4.31 (s, 3H), 3.84 (s, 3H). $^{13}$C NMR (75 MHz, DMSO-d6) δ170.9, 161.3, 142.0, 141.85, 141.8, 140.0, 139.5, 136.4, 135.0, 132.5, 129.4, 128.3, 127.9, 127.8, 126.7, 124.2, 116.7, 112.7, 52.5, 36.3. MALDI-TOF: m/z calcd for $C_{20}H_{16}NO_2S_3$ (M+H)$^+$: 399.0. Found: 399.1.

Example Compound 3g

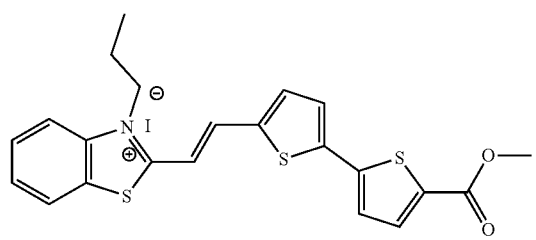

3g

General procedure of condensation reactions (G1) was applied with 1d and 2a. The residue was purified by crystallization from MeOH to give stilbene 3g. $^1$H NMR (300 MHz, DMSO-d6) δ8.50-8.42 (m, 2H), 8.31 (d, J=8.0 Hz, 1H), 8.00 (d, J=4.3 Hz, 1H), 7.91-7.74 (m, 5H), 7.63 (d, J=4.0 Hz, 1H), 4.88 (t, J=7.2 Hz, 2H), 3.86 (s, 3H), 1.89 (dd, J=14.5, 7.2 Hz, 2H), 1.01 (t, J=7.4 Hz, 3H). $^{13}$C NMR (75 MHz, DMSO-d6) δ170.9, 161.4, 142.0, 141.9, 141.3, 140.5, 139.4, 136.5, 135.0, 132.5, 129.5, 128.4, 128.2, 127.9, 126.7, 124.4, 116.8, 112.2, 52.5, 50.0, 22.2, 10.7. MALDI-TOF: m/z calcd for $C_{22}H_{20}NO_2S_3$ (M+H)$^+$: 427.1. Found: 427.1.

Example Compound 3h

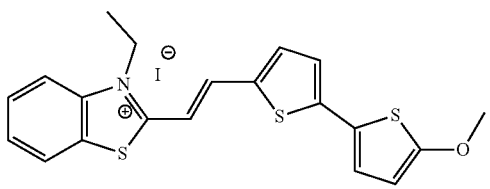

3h

General procedure of condensation reactions (G1) was applied with 1b and 2e. The residue was purified by crystallization from MeOH to give stilbene 3h. $^1$H NMR (300 MHz, DMSO-d6) δ8.45-8.37 (m, 2H), 8.24 (d, J=8.3 Hz, 1H), 7.90 (d, J=4.2 Hz, 1H), 7.88-7.71 (m, 3H), 7.57 (d, J=15.3 Hz, 1H), 7.40 (d, J=4.0 Hz, 1H), 7.31 (d, J=4.1 Hz, 1H), 6.45 (d, J=4.1 Hz, 1H), 4.89 (q, J=7.1 Hz, 2H), 3.95 (s, 3H), 1.45 (t, J=7.1 Hz, 3H). $^{13}$C NMR (75 MHz, DMSO-d6) δ171.0, 167.9, 146.1, 141.7, 141.3, 138.3, 136.8, 129.8, 128.5, 128.4, 126.0, 124.8, 124.7, 122.0, 116.7, 110.2, 106.6, 61.1, 44.6, 14.5. MALDI-TOF: m/z calcd for $C_{20}H_{18}NOS_3$ (M+H)$^+$: 385.1. Found: 385.1.

Example Compound 3i

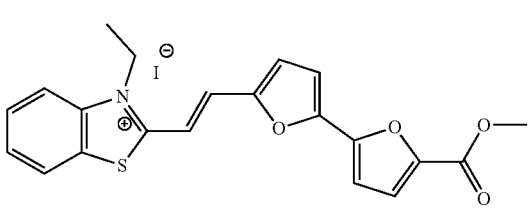

3i

General procedure of condensation reactions (G1) was applied with 1b and 2f. The residue was purified by crystallization from MeOH to give stilbene 3i. $^1$H NMR (300 MHz, DMSO-d6) δ8.45 (dd, J=8.1, 0.8 Hz, 1H), 8.31 (d, J=8.4 Hz, 1H), 8.19 (d, J=15.5 Hz, 1H), 7.92-7.75 (m, 2H), 7.70 (d, J=15.6 Hz, 1H), 7.57 (dd, J=5.0, 3.8 Hz, 2H), 7.35 (d, J=3.7 Hz, 1H), 7.32 (d, J=3.8 Hz, 1H), 4.95 (q, J=6.9 Hz, 2H), 3.87 (s, 3H), 1.49 (t, J=7.2 Hz, 3H). $^{13}$C NMR (75 MHz, DMSO-d6) δ170.9, 159.0, 154.1, 148.4, 141.9, 140.9, 139.3, 137.3, 136.7, 129.4, 128.2, 128.1, 125.8, 124.3, 116.4, 110.7, 107.5, 44.3, 27.7, 14.1. MALDI-TOF: m/z calcd for $C_{21}H_{18}NO_4S$ (M+H)$^+$: 381.1. Found: 381.1.

Example Compound 3j

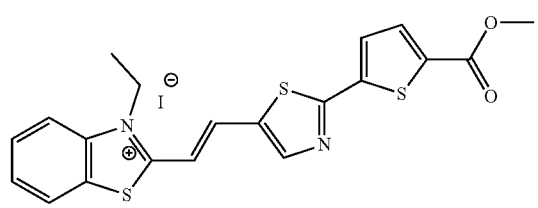

3j

General procedure of condensation reactions (G1) was applied with 1b and 2g. The residue was purified by crystallization from MeOH to give stilbene 3j. $^1$H NMR (300 MHz, DMSO-d6) δ8.59 (s, 1H), 8.56 (d, J=15.6 Hz, 1H), 8.45 (dd, J=8.1, 1.2 Hz, 1H), 8.30 (d, J=8.2 Hz, 1H), 7.92-7.76 (m, 5H), 4.94 (q, J=7.1 Hz, 2H), 3.87 (s, 3H), 1.46 (t, J=7.1 Hz, 3H). $^{13}$C NMR (75 MHz, DMSO-d6) δ170.5, 163.8, 161.3, 150.6, 141.4, 140.9, 137.8, 136.0, 135.4, 134.8, 129.7, 129.3, 128.6, 124.6, 116.8, 114.9, 52.7, 44.7, 14.2. MALDI-TOF: m/z calcd for $C_{20}H_{17}N_2O_2S_3$ (M+H)$^+$: 414.0. Found: 414.4.

Example Compound 3k

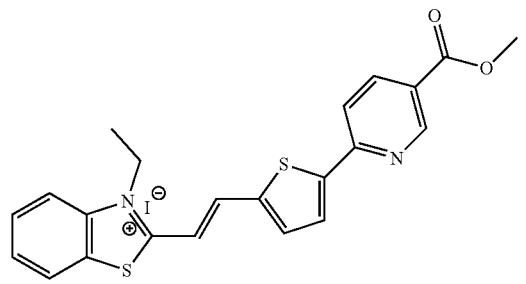

3k

General procedure of condensation reactions (G1) was applied with 1b and 2h. The residue was purified by crystallization from MeOH/THF (80:20) to give stilbene 3k. $^1$H NMR (300 MHz, DMSO-d6) δ 9.08 (dd, J=2.1, 0.8 Hz, 1H), 8.51-8.37 (m, 3H), 8.30 (d, J=8.4 Hz, 1H), 8.23 (dd, J=8.4, 0.8 Hz, 1H), 8.15 (d, J=4.1 Hz, 1H), 8.02 (d, J=4.1 Hz, 1H), 7.92-7.75 (m, 3H), 4.96 (q, J=7.2 Hz, 2H), 1.48 (t, J=7.2 Hz, 3H). $^{13}$C NMR (75 MHz, DMSO-d6) δ170.7, 164.7, 154.0, 150.4, 149.8, 142.1, 141.0, 140.9, 138.1, 136.5, 129.6, 128.8, 128.4, 128.4, 124.7, 124.5, 119.4, 116.6, 112.6, 52.5, 44.5, 14.2.

Example Compound 3*l*

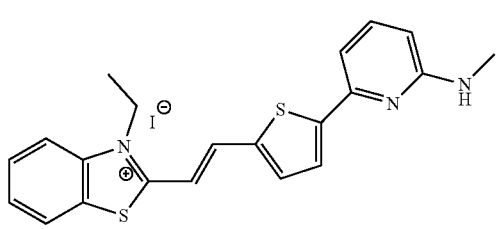

General procedure of condensation reactions (G1) was applied with 1b and 2i. The residue was purified by crystallization from MeOH to give stilbene 3l. $^1$H NMR (300 MHz, DMSO-d6) δ8.45-8.39 (m, 2H), 8.25 (d, J=8.5 Hz, 1H), 7.96 (d, J=4.0 Hz, 1H), 7.87-7.67 (m, 4H), 7.50-7.42 (m, 1H), 7.17 (d, J=7.3 Hz, 1H), 6.70 (q, J=4.2 Hz, 1H), 6.47 (d, J=8.3 Hz, 1H), 4.92 (q, J=7.1 Hz, 2H), 2.86 (d, J=4.7 Hz, 3H), 1.45 (t, J=7.1 Hz, 3H). $^{13}$C NMR (75 MHz, DMSO-d6) δ171.0, 159.0, 154.1, 148.4, 141.9, 140.9, 139.3, 137.3, 136.7, 129.4, 128.2, 128.1, 125.8, 124.3, 116.4, 110.7, 108.9, 107.5, 44.3, 27.7, 14.1. MALDI-TOF: m/z calcd for $C_{21}H_{20}N_3S_2$ (M+H)$^+$: 379.1. Found: 379.3.

Example Compound 3*m*

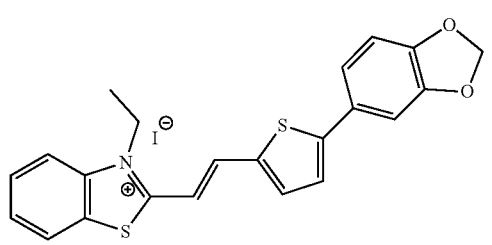

General procedure of condensation reactions (G1) was applied with 1b and 2j. The residue was purified by crystallization from MeOH/THF (80:20) to give stilbene 3m. $^1$H NMR (300 MHz, DMSO-d6) δ8.40 (dd, J=11.2, 5.9 Hz, 2H), 8.24 (d, J=8.4 Hz, 1H), 7.95 (d, J=4.1 Hz, 1H), 7.89-7.55 (m, 4H), 7.38 (d, J=1.8 Hz, 1H), 7.28 (dd, J=8.1, 1.8 Hz, 1H), 7.02 (d, J=8.1 Hz, 1H), 6.10 (s, 2H), 4.89 (q, J=7.1 Hz, 2H), 1.44 (t, J=7.1 Hz, 3H). $^{13}$C NMR (75 MHz, DMSO-d6) δ170.6, 151.5, 148.5, 148.3, 141.4, 140.9, 137.4, 137.3, 129.4, 128.2, 128.0, 126.8, 125.4, 124.3, 120.2, 116.4, 110.3, 109.1, 106.0, 101.8, 44.2, 14.1. MALDI-TOF: m/z calcd for $C_{22}H_{18}NO_2S_2$ (M+H)$^+$: 393.1. Found: 393.1.

Example Compound 3*n*

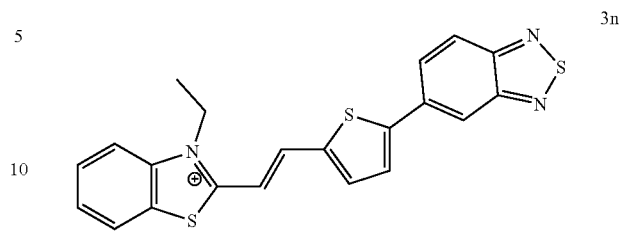

General procedure of condensation reactions (G1) was applied with 1b and 2k. The residue was purified by crystallization from MeOH to give stilbene 3n. $^1$H NMR (300 MHz, DMSO-d6) δ8.54-8.42 (m, 3H), 8.32-8.13 (m, 3H), 8.09 (s, 2H), 7.91-7.75 (m, 3H), 4.95 (q, J=7.1 Hz, 2H), 1.49 (t, J=7.1 Hz, 3H). $^{13}$C NMR (75 MHz, DMSO-d6) δ170.6, 154.5, 154.1, 148.7, 140.9, 140.8, 139.9, 136.6, 133.9, 129.5, 128.5, 128.4, 128.3, 124.4, 122.2, 117.0, 116.5, 111.9, 44.5, 14.2. MALDI-TOF: m/z calcd for $C_{21}H_{16}N_3S_3$ (M+H)$^+$: 407.1. Found: 407.1.

Example Compound 3*o*

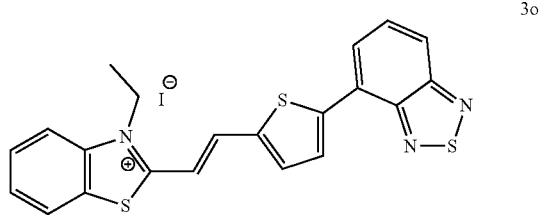 [SMILES: CC[n+]1c(/C=C/c2ccc(-c3cccc4nsnc34)s2)sc2ccccc21 ; [I-]]

General procedure of condensation reactions (G1) was applied with 1b and 2l. The residue was purified by crystallization from MeOH/THF (80:20) to give stilbene 3o. $^1$H NMR (300 MHz, DMSO-d6) δ8.54-8.41 (m, 3H), 8.31-8.14 (m, 3H), 8.09 (s, 2H), 7.91-7.74 (m, 3H), 4.96 (q, J=7.1 Hz, 2H), 1.49 (t, J=7.1 Hz, 3H). $^{13}$C NMR (75 MHz, DMSO-d6) δ171.1, 155.0, 154.6, 149.2, 141.4, 141.3, 140.4, 140.3, 137.1, 134.4, 130.0, 129.0, 128.8, 128.7, 124.9, 122.7, 117.4, 117.0, 112.4, 44.9, 14.7. MALDI-TOF: m/z calcd for $C_{21}H_{16}N_3S_3$ (M+H)$^+$: 407.1. Found: 407.2.

Example Compound 3*p*

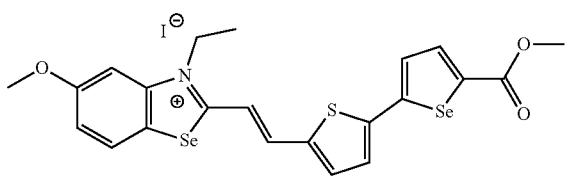

General procedure of condensation reactions (G1) was applied with 1f and 2m. The residue was purified by crystallization from MeOH to give stilbene 3p.

Example Compound 3q

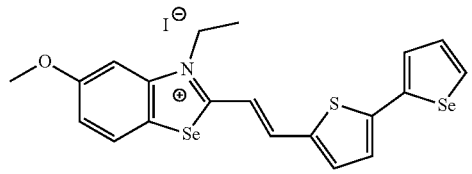

3q

General procedure of condensation reactions (G1) was applied with 1f and 2n. The residue was purified by crystallization from MeOH to give stilbene 3q.

Example Compound 3r

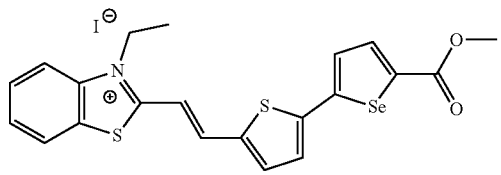

3r

General procedure of condensation reactions (G1) was applied with 1b and 2m. The residue was purified by crystallization from MeOH to give stilbene 3r.

Example Compound 3s

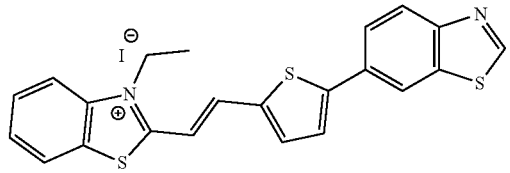

3s

General procedure of condensation reactions (G1) was applied with 1b and 2o. The residue was purified by crystallization from MeOH to give stilbene 3s.

Example Compound 3t

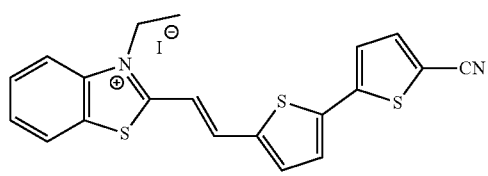

3t

General procedure of condensation reactions (G1) was applied with 1b and 2p. The residue was purified by crystallization from MeOH to give stilbene 3t.

Example Compound 3u

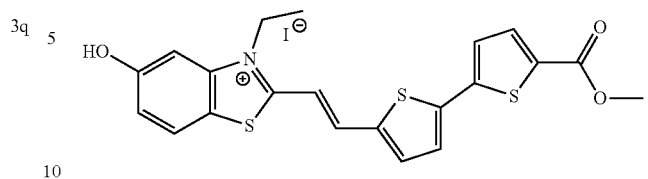

3u

General procedure of condensation reactions (G1) was applied with 1e and 2a. The residue was purified by crystallization from MeOH to give stilbene 3u.

(G2 & G3) Procedure:
Starting Materials 5a and 5b and 7a-d

| Structures of staring materials 5a and 5b | |
|---|---|
| 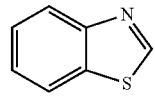 | 5a |
| 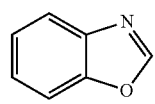 | 5b |
| Structures of starting materials 7a-7d | |
| 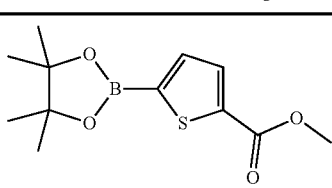 | 7a |
| 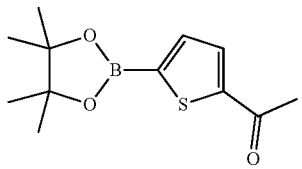 [SMILES: CC(=O)c1ccc(B2OC(C)(C)C(C)(C)O2)s1] | 7b |
| 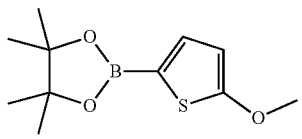 | 7c |
| 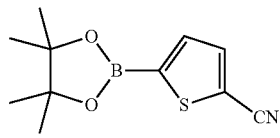 [SMILES: CC1(C)OB(c2ccc(C#N)s2)OC1(C)C] | 7d |

Intermediate Compounds 6a and 6b
Intermediate 6a

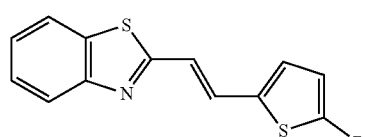

6a

General procedure of condensation reactions (G2) was applied starting with 2-methylbenzothiazole (5a) (200 mg, 1.34 mmol) and 5-bromothiophene-2-carbaldehyde (4) (256 mg, 1.34 mmol). The residue was subjected to column chromatography using [heptane/EtOAc (10:1→6:1)] to give stilbene 6a (220 mg, 51%) as yellow solid. $^1$H NMR (300 MHz, CDCl$_3$) δ7.99-7.95 (m, 1H), 7.83 (ddd, J=7.9, 1.3, 0.6 Hz, 1H), 7.52 (dd, J=16.0, 0.6 Hz, 1H), 7.49-7.32 (m, 2H), 7.07 (d, J=16.0 Hz, 1H), 7.00 (d, J=3.9 Hz, 1H), 6.96 (d, J=3.9 Hz, 1H). $^{13}$C NMR (75 MHz, CDCl$_3$) δ166.0, 154.0, 142.5 134.5, 131.1, 129.5, 129.4, 126.6, 125.6, 123.1, 121.7, 121.6, 114.7. MALDI-TOF: m/z calcd for C$_{13}$H$_8$BrNS$_2$ (M+H)$^+$: 322.0. Found: 322.1.

Intermediate 6b

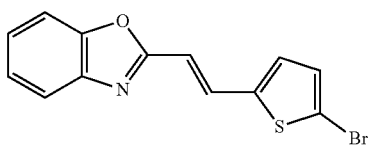

6b

General procedure of condensation reactions (G2) was applied starting with 2-methylbenzoxazole (5b) (200 mg, 1.50 mmol) and 5-bromothiophene-2-carbaldehyde (4) (287 mg, 1.50 mmol). The residue was subjected to column chromatography using [heptane/EtOAc (10:1)] followed by crystallization from MeOH to give stilbene 6b (220 mg, 48%) as yellow solid. $^1$H NMR (300 MHz, CDCl$_3$) δ7.75 (d, J=16.1 Hz, 1H), 7.72-767 (m, 1H), 7.55-7.45 (m, 1H), 7.37-7.28 (m, 2H), 7.04-7.00 (m, 2H), 6.76 (d, J=16.0 Hz, 1H). $^{13}$C NMR (75 MHz, CDCl$_3$) δ162.3, 150.6, 142.4, 142.2, 131.3, 131.2, 130.0, 125.5, 124.8, 120.0, 115.3, 113.4, 110.4. MALDI-TOF: m/z calcd for C$_{13}$H$_8$BrNOS (M+H)$^+$: 306.0. Found: 306.1.

Compounds of the Invention

Example Compound 8a

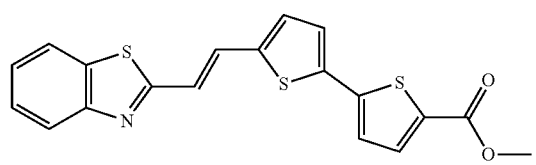

8a

General procedure of Suzuki coupling (G3) with 6a and 7a. The residue was treated with warm MOH, collected by filtration and the product was further crystallized from DMF to give 8a as yellow solid. $^1$H NMR (300 MHz, CDCl$_3$) δ7.99 (d, J=8.1 Hz, 1H), 7.86 (d, J=7.3 Hz, 1H), 7.72 (d, J=4.0 Hz, 1H), 7.62 (d, J=16.0 Hz, 1H), 7.52-7.33 (m, 2H), 7.24-7.17 (m, 4H), 3.91 (s, 3H). $^{13}$C NMR (75 MHz, CDCl$_3$) δ166.1, 162.5, 154.1, 143.6, 141.3, 137.8, 134.6, 134.5, 132.3, 130.4, 129.6, 126.6, 126.1, 125.6, 124.7, 123.1, 121.9, 121.7, 52.4. MALDI-TOF: m/z calcd for C$_{19}$H$_{13}$NO$_2$S$_3$ (M+H)$^+$: 384.0. Found: 384.3.

Example Compound 8b

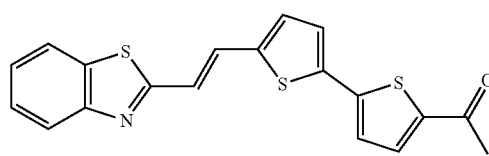

8b

General procedure of Suzuki coupling (G3) with 6a and 7b. The residue was treated with warm MOH and collected by filtration to give 8b as red solid. $^1$H NMR (300 MHz, CDCl$_3$) δ8.03-7.94 (m, 1H), 7.85 (ddd, J=7.9, 1.2, 0.6 Hz, 1H), 7.66-7.54 (m, 2H), 7.54-7.31 (m, 2H), 7.29-7.13 (m, 4H), 2.55 (s, 3H). $^{13}$C NMR (75 MHz, CDCl$_3$) δ190.4, 166.0, 154.0, 145.0, 143.3, 141.7, 137.8, 134.6, 133.4, 130.5, 129.5, 126.6, 126.5, 125.6, 125.0, 123.1, 122.1, 121.7, 26.7. MALDI-TOF: m/z calcd for C$_{19}$H$_{13}$NOS$_3$ (M+H)$^+$: 368.0. Found: 368.3.

Example Compound 8c

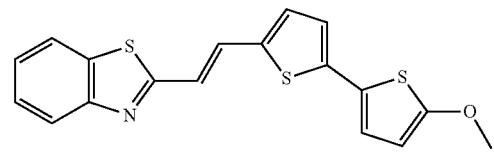

8c

General procedure of Suzuki coupling (G3) with 6a and 7c. The residue was treated with warm MOH and collected by filtration to give 8c as red solid. $^1$H NMR (300 MHz, CDCl$_3$) δ7.97 (d, J=7.8 Hz, 1H), 7.84 (dd, J=8.0, 0.7 Hz, 1H), 7.59 (d, J=15.8 Hz, 1H), 7.49-7.31 (m, 2H), 7.10 (dd, J=9.8, 6.0 Hz, 2H), 6.93 (d, J=3.8 Hz, 1H), 6.89 (d, J=4.0 Hz, 1H), 6.15 (d, J=4.0 Hz, 1H), 3.92 (s, 3H). $^{13}$C NMR (75 MHz, CDCl$_3$) δ166.7, 166.6, 154.0, 154.0, 140.3, 138.4, 134.5, 130.7, 130.4, 126.5, 125.3, 123.5, 122.9, 122.7, 121.6, 120.3, 105.0, 60.5. MALDI-TOF: m/z calcd for C$_{18}$H$_{13}$NOS$_3$ (M+H)$^+$: 356.0. Found: 356.1.

Example Compound 8d

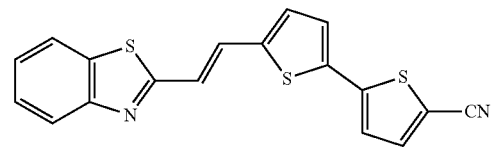

8d

General procedure of Suzuki coupling (G3) with 6a and 7d. The residue was treated with warm MOH and collected by filtration to give 8d as dark red solid. $^1$H NMR (300 MHz, CDCl$_3$) δ8.00 (ddd, J=8.0, 1.3, 0.7 Hz, 1H), 7.86 (ddd, J=7.9, 1.3, 0.7 Hz, 1H), 7.61 (dd, J=16.0, 0.5 Hz, 1H), 7.54 (d, J=3.9 Hz, 1H), 7.52-7.35 (m, 2H), 7.26-7.18 (m, 4H). $^{13}$C NMR (75 MHz, CDCl$_3$) δ165.8, 154.0, 144.0, 142.2, 138.4, 136.1, 134.7, 130.3, 129.2, 126.9, 126.7, 125.7, 124.2, 123.2, 122.5, 121.7, 114.1, 108.4. MALDI-TOF: m/z calcd for C$_{18}$H$_{10}$N$_2$S$_3$ (M+H)$^+$: 351.0. Found: 351.1.

Example Compound 8e

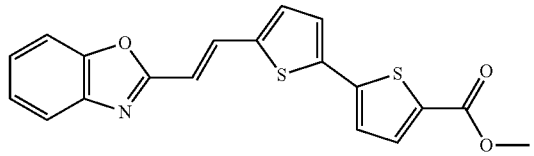

General procedure of Suzuki coupling (G3) with 6b and 7a. The residue was treated with warm MOH and collected by filtration to give 7e as yellow solid. $^1$H NMR (300 MHz, CDCl$_3$) δ7.86-7.69 (m, 3H), 7.54-7.49 (m, 1H), 7.37-7.30 (m, 2H), 7.22 (dt, J=3.8, 3.0 Hz, 3H), 6.86 (d, J=16.0 Hz, 1H), 3.91 (s, 3H). $^{13}$C NMR (75 MHz, CDCl$_3$) δ162.5, 162.4, 150.6, 143.4, 142.4, 141.0, 138.4, 134.5, 132.4, 131.5, 130.9, 126.1, 125.5, 124.9, 124.8, 120.1, 113.7, 110.5, 52.5. MALDI-TOF: m/z calcd for C$_{19}$H$_{13}$NO$_3$S$_2$ (M+H)$^+$: 368.0. Found: 368.3.

COMPARATIVE EXAMPLE 1

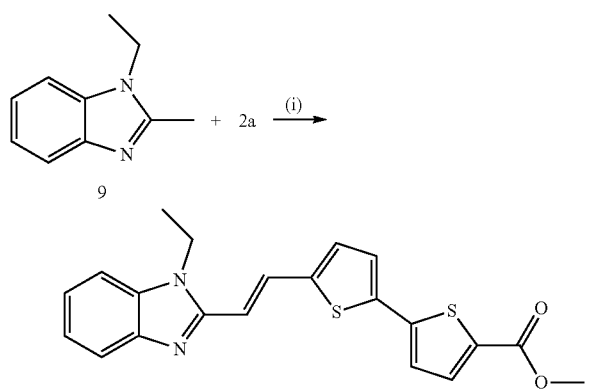

Comparative Example 1

Reagents and conditions: (i) DMF, TMSCI, 110° C., 2 h.

Comparative Example 1 was synthesized according to known procedure described in literature (Cao, C., et al, *CHINESE. J. CHEM.*, 2015, 1077-1083) from 2-Methyl-1-ethyl-benzimidazol (9) (32 mg, 0.2 mmol), the 2a (50 mg, 0.2 mmol), TMSCI (65 mg, 0.60 mmol) and dry DMF (5 ml) as solvent. The residue, red oil, was purified by column chromatography using [n-heptane/EtOAc (3:1)] to give Comparative Example 1 (32.0 mg, 41%) as yellow solid. The product was dissolved in 1,4-dioxane and the solution was lyophilized. IR (neat) 1708, 1439, 1408, 1314, 1277, 1244, 1232, 1213, 1190, 1093, 961, 788, 739, 704 cm$^{-1}$. $^1$H NMR (300 MHz, CDCl$_3$) δ8.00 (d, J=15.5 Hz, 1H), 7.72-7.66 (m, 1H), 7.64 (d, J=4.0 Hz, 1H), 7.29-7.08 (m, 6H), 6.77 (d, J=15.5 Hz, 1H), 4.23 (q, J=7.3 Hz, 2H), 3.83 (s, 3H), 1.41 (t, J=7.3 Hz, 3H). $^{13}$C NMR (75 MHz, CDCl$_3$) δ162.5, 149.8, 143.8, 143.4, 142.0, 136.9, 135.1, 134.5, 132.1, 130.3, 129.7, 126.1, 124.5, 122.9, 122.9, 119.5, 112.7, 109.4, 52.4, 38.4, 15.7. MALDI-TOF: m/z calcd for C$_{21}$H$_{18}$N2O$_2$S$_2$ (M+H)$^+$: 395.1. Found: 395.6.

COMPARATIVE EXAMPLES 2 to 4

Intermediates:

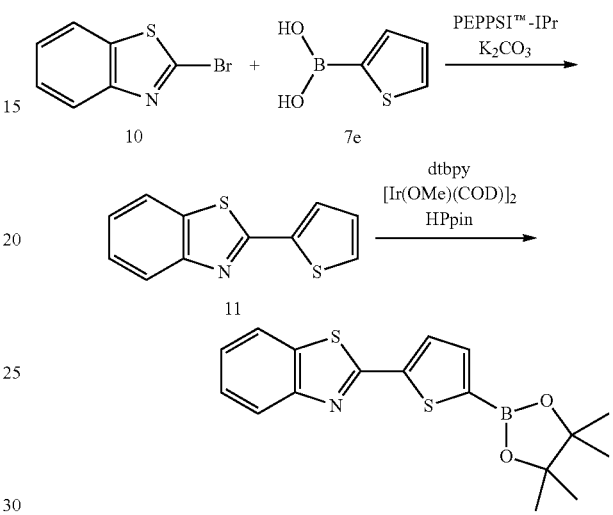

2-(thiophen-2-yl)benzo[d]thiazole (11): General procedure of Suzuki coupling (G3) was applied starting with 2-Bromobenzothiazole (400 mg, 1.87 mmol) and 2-Thienylboronic acid (7e) (263 mg, 2.1 mmol). The residue was subjected to column chromatography using [heptane/EtOAc 2%] to give dimer 11 (260 mg, 64%) as white solid. The spectral and physical data for 11 were in excellent agreement with those reported previously (Park, N., et al, *Eur. J. Org. Chem.*, 2012, 1984-1993).

2-(5-(4,4,5,5-tetramethyl-1,3,2-dioxaborolan-2-yl)thiophen-2-yl)benzo[d]thiazole (12): To a mixture of (1,5-Cyclooctadiene)(methoxy)indium(1) dimer [Ir(OMe)(COD)]$_2$ (0.0025 equvi.), 4,4'-di-tert-butyl-2,2'-bipyridine (dtbpy) (0.0050 equvi.) and the dimer 10 (150 mg, 0.690 mmol) in dry in dry THF was added 4,4,5,5-tetramethyl-1,3,2-dioxaborolane (HBPin) (133 mg, 1.0 mmol) and heated at 75° C. under argon for 18 h. The solvent was evaporated and the residue, dark oil, was purified by column chromatography using [n-heptane/EtOAc (3:1→1:1)] to give compound 12 (200 mg, 84%) as white solid. IR (neat) 1535, 1495, 1445, 1429, 1371, 1346, 1290, 1266, 1231, 1139, 1076, 1015, 906, 853, 821, 754, 726 cm$^{-1}$. 1H NMR (300 MHz, cdcl$_3$) δ8.07-7.83 (m, 2H), 7.73 (d, J=3.7 Hz, 1H), 7.62 (d, J=3.7 Hz, 1H), 7.50-7.34 (m, 2H), 1.36 (s, 12H). $^{13}$C NMR (75 MHz, CDCl$_3$) δ161.1, 154.0, 143.4, 137.7, 135.2, 129.4, 126.6, 125.5, 123.4, 121.6, 84.6, 24.9. MALDI-TOF: m/z calcd for C$_{17}$H$_{18}$BNO$_2$S$_2$ (M+H)$^+$: 344.1. Found: 344.5.

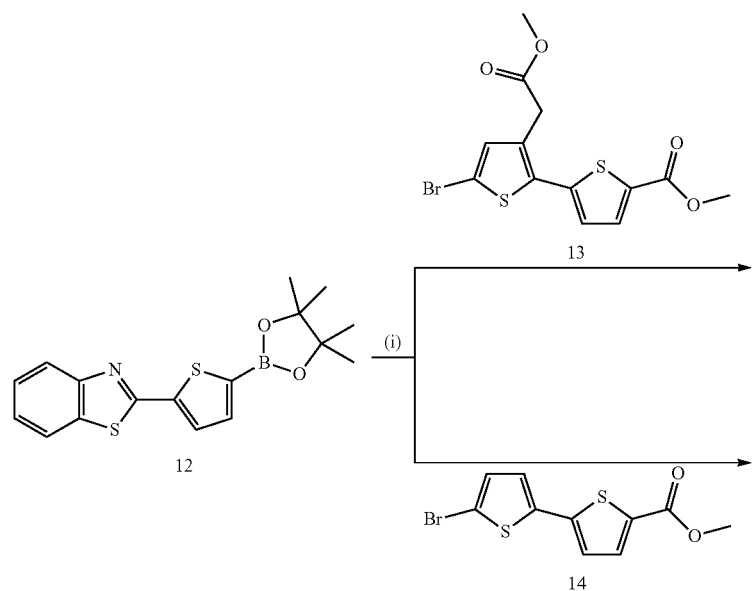
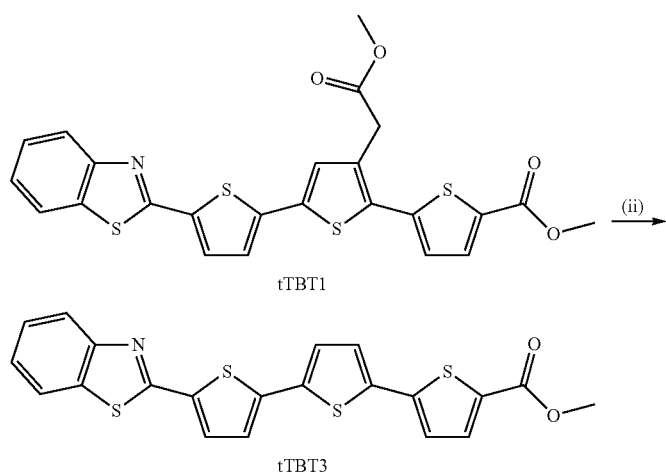
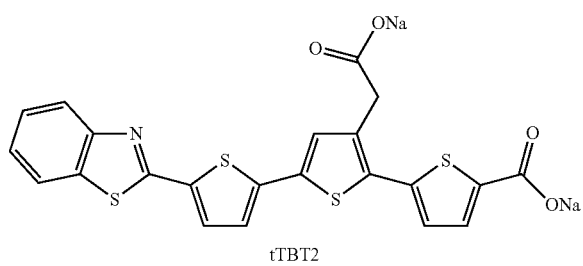

Reagents and conditions: (i) 1,4-dioxane/MeOH, PEPPSI-IPr, $K_2CO_3$, 80° C., 20 min.; (ii) NaOH (1M), 1,4-dioxane, 70° C., 5 h.

COMPARATIVE EXAMPLE 2

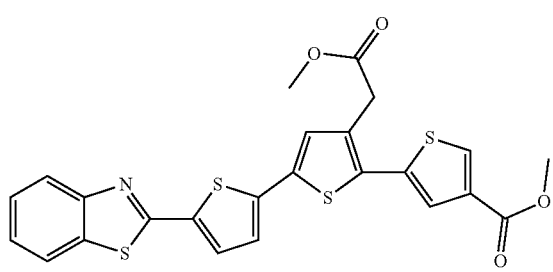 [SMILES: COC(=O)Cc1cc(-c2ccc(-c3nc4ccccc4s3)s2)sc1-c1cc(C(=O)OC)cs1]

General procedure of Suzuki coupling (G3) was applied starting with compound 12 (70 mg, 0.204 mmol) and dimer 13 (77.0 mg, 0.204 mmol). The residue was treated with warm acetonitrile and collected by filtration to give Comparative Example 2 (65 mg, 62%) as brownish solid.

IR (neat) 1735, 1689, 1433, 1414, 1329, 1314, 1293, 1221, 1169, 1101, 1048, 1014, 973, 909, 850, 808, 749, 733, 701 $cm^{-1}$. $^1H$ NMR (300 MHz, $CDCl_3$) δ8.05-7.99 (m, 1H), 7.88-7.83 (m, 1H), 7.77 (d, J=4.0 Hz, 1H), 7.56 (d, J=4.0 Hz, 1H), 7.48 (ddd, J=8.0, 7.3, 1.2 Hz, 1H), 7.37 (ddd, J=8.0, 7.3, 1.2 Hz, 1H), 7.25 (s, 1H), 7.22 (d, J=1.6 Hz, 1H), 7.20 (d, J=1.6 Hz, 1H), 3.91 (s, 3H), 3.80 (s, 2H), 3.76 (s, 3H). $^{13}C$ NMR (75 MHz, $cdcl_3$) δ170.8, 162.5, 160.8, 153.8, 141.5, 140.1, 136.5, 136.4, 134.9, 134.2, 133.6, 132.5, 132.4, 129.4, 128.1, 127.3, 126.7, 125.5, 125.0, 123.1, 121.6, 52.6, 52.5, 35.0. MALDI-TOF: m/z calcd for $C_{24}H_{17}NO_4S_4$ $(M+H)^+$: 512.0. Found: 512.0.

COMPARATIVE EXAMPLE 3

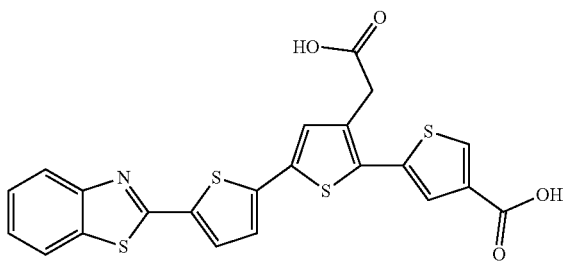 [SMILES: O=C(O)Cc1cc(-c2ccc(-c3nc4ccccc4s3)s2)sc1-c1cc(C(=O)O)cs1]

NaOH (1 M, 1.5 equiv./ester) was added to a solution of the tTBT2 (25 mg, 0.233 mmol) in 1,4-dioxane/$H_2O$ (8/2, 10 ml) and heated to 70° C. for 5 h. The solvents was evaporated and the residue was dissolved in water and the solution was lyophilized to give Comparative Example 3 as red solid with quantitative yield. IR (neat) 1567, 1518, 1443, 1370, 1311, 1256, 1228, 1033, 1014, 910, 832, 799, 770, 752, 723 $cm^{-1}$. $^1H$ NMR (300 MHz, DMSO-d6) δ8.12-8.10 (m, 1H), 8.01-7.99 (m, 1H), 7.80 (d, J=4.0 Hz, 1H), 7.57-7.49 (m, 1H), 7.48-7.41 (m, 1H), 7.39 (s, 1H), 7.38 (d, J=4.0 Hz, 1H), 7.34 (d, J=3.7 Hz, 1H), 7.16 (d, J=3.7 Hz, 1H), 3.35 (s, 2H). $^{13}C$ NMR (75 MHz, DMSO-d6) δ172.5, 164.1, 160.3, 153.1, 148.7, 140.7, 138.0, 135.8, 134.2, 134.0, 131.5, 131.1, 130.8, 130.5, 127.6, 126.8, 126.3, 125.5, 124.6, 122.4, 122.3[(a)]. MALDI-TOF: m/z calcd for $C_{22}H_{13}NO_4S_4$ $(M+H)^+$: 484.0. Found: 484.1.

COMPARATIVE EXAMPLE 4

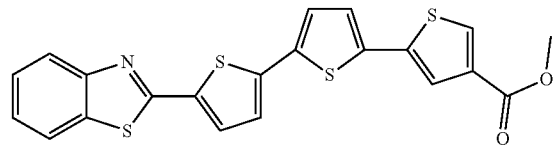 [SMILES: COC(=O)c1csc(-c2ccc(-c3ccc(-c4nc5ccccc5s4)s3)s2)c1]

General procedure of Suzuki coupling (G3) was applied starting with compound 7 (80 mg, 0.233 mmol) and dimer 14 (71 mg, 0.233 mmol). The residue was re-crystallized from acetonitrile and collected by filtration to give Comparative Example 4 (55 mg, 54%) as greenish solid.

IR (neat) 1705, 1433, 1292, 1278, 1239, 1229, 1095, 913, 860, 774, 754, 743, 731, 704 $cm^{-1}$. $^1H$ NMR (300 MHz, $CDCl_3$) δ8.05-8.01 (m, 1H), 7.88-7.84 (m, 1H), 7.71 (d, J=3.9 Hz, 1H), 7.56 (d, J=4.0 Hz, 1H), 7.60-7.32 (m, 3H), 7.26-7.13 (m, 7H), 3.91 (s, 3H). $^{13}C$ NMR (75 MHz, $CDCl_3$) δ162.5, 160.8, 153.9, 143.6, 140.4, 137.2, 136.4, 134.9, 134.5, 131.9, 129.4, 126.7, 126.3, 125.8, 125.5, 124.8, 124.3, 123.1, 121.6, 52.4. MALDI-TOF: m/z calcd for $C_{21}H_{13}NO_2S_4$ $(M+H)^+$: 440.0. Found: 440.0.

Biological Testing of Example Compounds and Comparative Examples (i) Histological Staining of Alzheimer's Disease (AD) Brain Tissue Sections with Example Compounds and Comparative Examples Reagents and Procedure Compound and Antibody Double Staining of Tissue Samples To achieve compound and antibody double staining of Aβ or tau aggregates, tissue sections (20 μm) from human AD brain were fixed in 70% EtOH at 4° C. for 3 min, rehydrated in distilled water and then incubated in PBS for 30 min. Sections were blocked and permeabilized in PBS with 5% normal goat serum and 0.1% triton X-100 (blocking buffer) for 1 h at room temperature (RT). Antibody 4G8 (Biolegend, San Diego, Calif., USA) reactive to Aβ, and AT100 (Thermo Fisher Scientific, Waltham, Mass., USA) directed against tau phosphorylated at serine 212 and threonine 214 (3) were diluted 1:500 and 1:1000, respectively, in blocking buffer and added to the sections. After 16 h incubation at 4° C. unbound antibody was removed by washing in PBS with 0.1% triton X-100 (PBS-T) 3×10 min. To visualize antibody binding to Aβ or tau aggregates sections were incubated with goat anti-mouse secondary antibody labelled with Alexa 647 (Thermo Fisher Scientific). The antibody was diluted 1:200 in blocking buffer and after 1 h incubation at RT sections were washed in PBS 3×10 min. Example Compound 3a, Example Compound 3b, Example Compound 3c, Example Compound 3d, Example Compound 3e, Example Compound 3f, Example Compound 3g, Example Compound 3h, Example Compound 3i, Example Compound 3j, Example Compound 3k, Example Compound 3m, Example Compound 3n, Example Compound 3o, Example Compound 3p, Example Compound 3q, Example Compound 3r, Example Compound 3s, Example Compound 3t, Example Compound 3u, Example Compound 8a, Comparative Example 1, Comparative Example 2, Comparative Example 3 and Comparative Example 4 were dissolved in DMSO to a concentration of 1.5 mM and then further diluted in PBS to a final concentration of 100 nM compound prior to staining. The tissue sections were then stained for 30 min at RT with these freshly prepared solutions containing 100 nM of the respective compound in PBS. After three washes in PBS the sections were mounted in Dako mounting medium for fluorescence (Dako Cytomation, Glostrup, Denmark) and allowed to dry overnight before analysis. Fluorescence images were collected using an inverted LSM 780 confocal microscope (Carl Zeiss, Oberkochen, Germany) with the following excitation/emission wavelengths optimized for each compound: 458/484-600 (Comparative Example 1, Comparative Example 3), 561/569-648 (Example Compound 3a, Example Compound 3b, Example Compound 3c, Example Compound 3d, Example Compound 3e, Example Compound 3f, Example Compound 3g, Example Compound 3h, Example Compound 3i, Example Compound 3j, Example Compound 3k, Example Compound 3m, Example Compound 3n, Example Compound 3o, Example Compound 3p, Example Compound 3q, Example Compound 3r, Example Compound 3s, Example Compound 3t, Example Compound 3u, Example Compound 8a, Comparative Example 2 and Comparative Example 4) and 633/638-755 (Alexa 647). To visualize autofluorescent lipofuscin excitation/emission wavelengths 405/410-480 or 405/410-514 were used.

Compound Staining and Spectral Analysis of Tissue Samples

Frozen brain sections (20 μm) were fixed in 96% EtOH, rehydrated in 50% EtOH and de-ionized water and then incubated in phosphate buffered saline (PBS, 10 mM phosphate, 140 mM NaCl, 2.7 mM KCl, pH 7.4) for 10 min. Example Compound 3a, Example Compound 3b, Example Compound 3c, Example Compound 3d, Example Compound 8a and PBB3 were dissolved in DMSO to a concentration of 1.5 mM and then further diluted to 100 nM in PBS and added to the sections. After 30 min, the sections were washed with PBS and mounted with Dako fluorescent mounting medium (Dako Cytomation, Glostrup, Denmark). The mounting medium was allowed to solidify over night before collecting emission spectra of the compounds bound to misfolded Aβ and tau using an inverted LSM 780 confocal microscope (Carl Zeiss, Oberkochen, Germany) with excitation wavelength at 561 nm. Emission spectra were collected between 561 nm to 687 nm. Main beam splitter was MBS458/561, and the pinhole was set to 52 μm. For Example Compound 3a, Example Compound 3b, Example Compound 3c, Example Compound 3d and Example Compound 8a, excitation spectra were recorded with the same microscope system using a tunable In Tune laser and the excitation wavelength were scanned between 490 to 600 nm having the emission fixed at 612 to 639 nm.

Results of Histological staining of Alzheimer's Disease (AD) Brain Tissue Sections with Example Compounds and Comparative Examples In order to evaluate if the compounds of the invention were interacting with Aβ or tau aggregates, 100 nM of the Example Compounds 3a, 3b, 3c, 3d, 3e, 3f, 3g, 3h, 3i, 3j, 3k, 3m, 3n, 3o, 3p, 3q, 3r, 3s, 3t, 3u and 8a were applied for histological staining of brain tissue sections with AD pathology, as described above.

Figure 1:
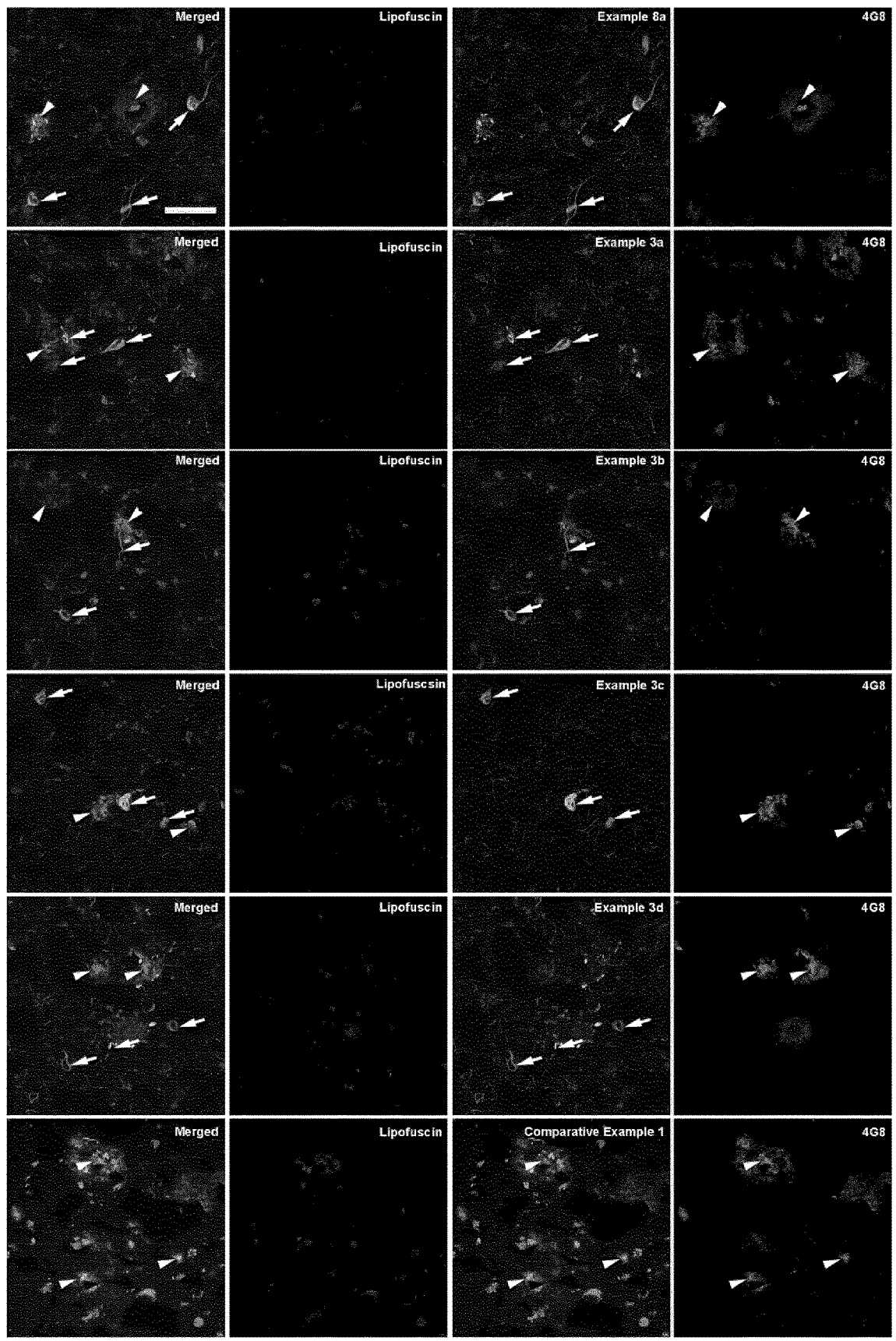
FIG. 1 shows brain tissue sections with Alzheimer's disease pathology stained by Example Compounds 3a, 3b, 3c, 3d and 8a, and Comparative Example 1. Column 2 shows auto-fluorescence from lipofuscin; column 3 shows the staining with Example Compounds 3a, 3b, 3c, 3d or 8a, or Comparative Example 1; and column 4 shows staining with an antibody against Aβ (4G8); column 1 shows the merged results. Scale bar represents 50 μm.

The results are summarized in Table 1, below. The results are also shown in FIGS. 1 and 8 (FIG. 1 shows the staining with Example Compounds and the antibody (4G8); FIG. 8 shows the staining with Example Compounds only).

As can be seen from FIG. 1, and as reported in Table 1, when stained in combination with an antibody (4G8) for Aβ pathology, Example Compounds 3a, 3b, 3c, 3d and 8a showed no correlation with the 4G8 antibody staining.

In more detail, FIG. 1, column 4 shows staining with the antibody (4G8) for Aβ pathology; and FIG. 1, column 3 shows staining with Example Compounds 3a, 3b, 3c, 3d or 8a (rows 1 to 5); and FIG. 1, column 2 shows the autofluorescence from lipofuscin. When each fluorescence is merged, as shown in column 1 of FIG. 1, the staining pattern for the compounds of the invention (rows 1 to 5) is distinct to the staining pattern for the antibody (4G8) for Aβ pathology. The compounds of the invention appeared to stain aggregated species composed of tau, whereas the staining of Aβ pathology was lacking. These results are summarized in Table 1, below.

As reported in Table 1, when stained in combination with an antibody (4G8) for Aβ pathology, Example Compounds 3e, 3f, 3g, 3h, 3i, 3j, 3k, 3m, 3n, 3o, 3p, 3q, 3r, 3s, 3t, and 3u also showed no correlation with the 4G8 antibody staining.

As described above, 100 nM of Comparative Example 1 was also applied for histological staining of brain tissue sections with AD pathology. Comparative example 1 showed overlap with the 4G8 staining as well as some minor staining from dystrophic neurites (FIG. 1, row 6). Thus, in contrast to the results for Example Compounds 3a, 3b, 3c, 3d, 3e, 3f, 3g, 3h, 3i, 3j, 3k, 3m, 3n, 3o, 3p, 3q, 3r, 3s, 3t, 3u and 8a, Comparative Example 1 displayed staining towards immune-positive Aβ aggregates, as well as some weak staining of tau-like pathology. This result is also summarized in Table 1, below.

Figure 3:
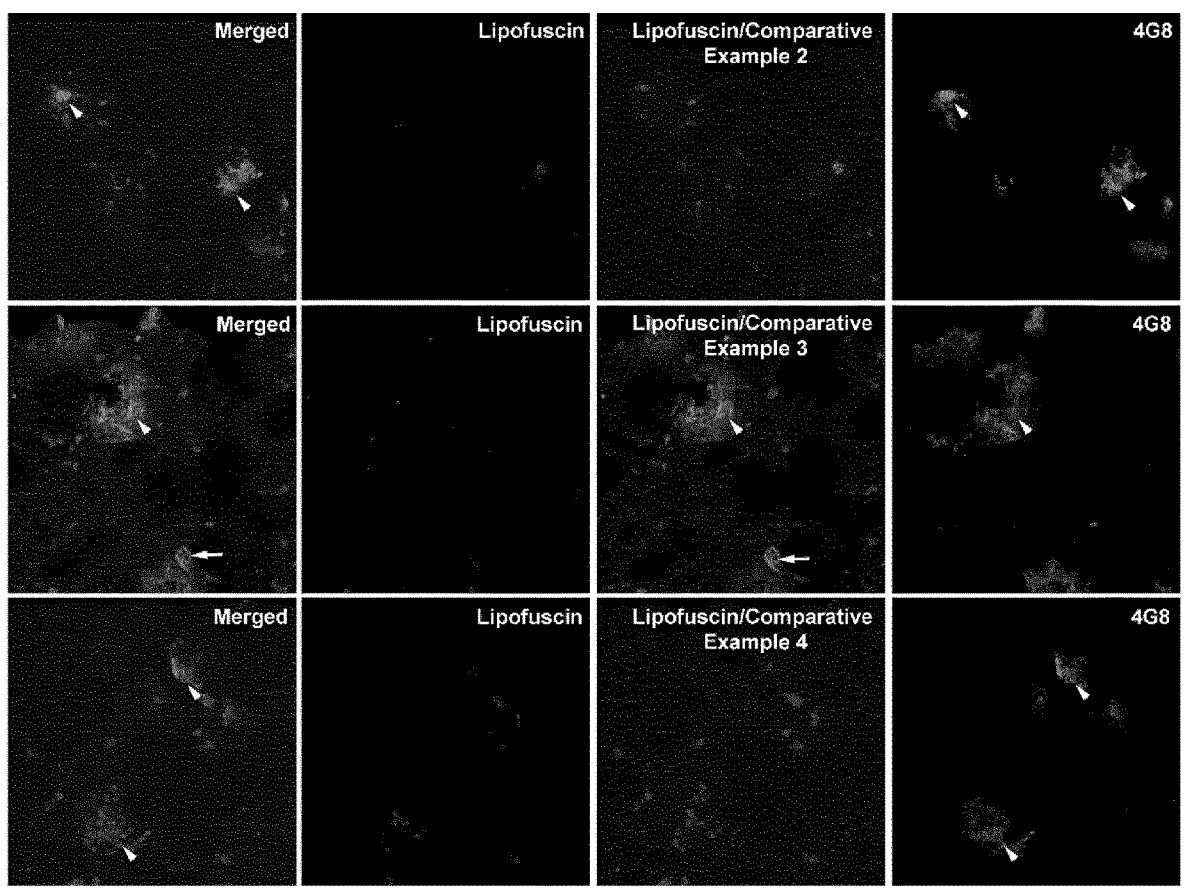
FIG. 3 shows fluorescence images of brain tissue sections with Alzheimer's disease pathology stained by Comparative Examples 2, 3 and 4. Column 2 shows auto-fluorescence from lipofuscin; column 3 shows staining with comparative Example Compounds 2, 3 or 4 (and lipofuscin, which fluoresces in the same band of excitation); and column 4 shows the staining with an antibody towards Aβ (4G8); column 1 shows the merged results.

100 nM of Comparative Examples 2, 3 and 4 were also applied for histological staining of brain tissue sections with AD pathology, as described above. The results are shown in FIG. 3. Comparative examples 2 and 4 did not display any substantial staining of any of the pathological aggregated species in Alzheimer's disease brain (FIG. 3, rows 1 and 3). Comparative example 3 displayed overlap with the 4G8 staining as well as staining from tau-like pathology (FIG. 3, row 2). Thus Comparative Example 3 displayed staining of both Aβ and tau aggregates. These results is also summarized in Table 1, below.

TABLE 1

| Example number or Comparative Example numbers | Fluorescence from tested compound observed | Fluorescence from 4G8 observed | Overlap between Fluorescence from tested compound and fluorescence from 4G8 observed |
| --- | --- | --- | --- |
| Example Compound 3a | yes | yes | no |
| Example Compound 3b | yes | yes | no |
| Example Compound 3c | yes | yes | no |
| Example Compound 3d | yes | yes | no |
| Example Compound 3e | yes | yes | no |
| Example Compound 3f | yes | yes | no |
| Example Compound 3g | yes | yes | no |
| Example Compound 3h | yes | yes | no |
| Example Compound 3i | yes | yes | no |
| Example Compound 3j | yes | yes | no |
| Example Compound 3k | yes | yes | no |
| Example Compound 3m | yes | yes | no |
| Example Compound 3n | yes | yes | no |

TABLE 1-continued

| Example number or Comparative Example numbers | Fluorescence from tested compound observed | Fluorescence from 4G8 observed | Overlap between Fluorescence from tested compound and fluorescence from 4G8 observed |
|---|---|---|---|
| Example Compound 3o | yes | yes | no |
| Example Compound 3p | yes | yes | no |
| Example Compound 3q | yes | yes | no |
| Example Compound 3r | yes | yes | no |
| Example Compound 3s | yes | yes | no |
| Example Compound 3t | yes | yes | no |
| Example Compound 3u | yes | yes | no |
| Example Compound 8a | yes | yes | no |
| Comparative example 1 | Yes (very weak) | yes | yes |
| Comparative example 2 | no | yes | n/a |
| Comparative example 3 | yes | yes | yes |
| Comparative example 4 | no | yes | n/a |

Figure 2:
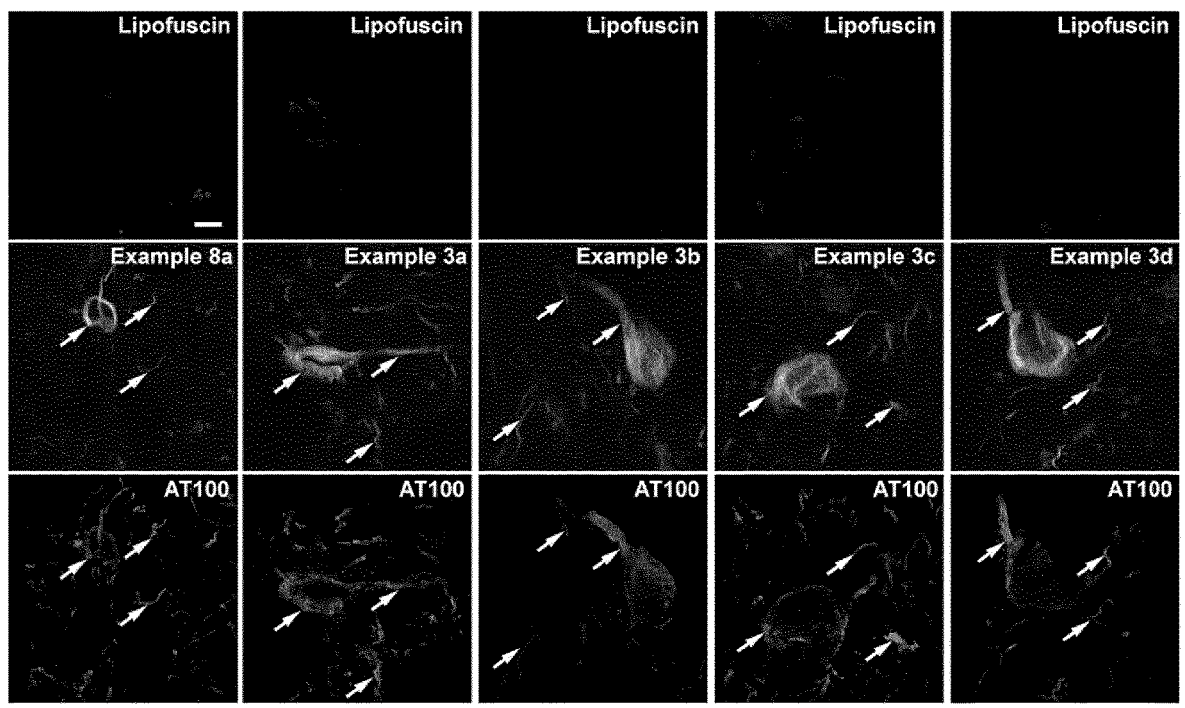
FIG. 2 shows fluorescence images of brain tissue sections with Alzheimer's disease pathology co-stained by Example Compounds 3a, 3b, 3c, 3d and 8a and the tau specific antibody AT100. Row 1 shows auto-fluorescence from lipofuscin; row 2 shows the staining with Example Compounds 3a, 3b, 3c, 3d or 8a; and row 3 shows staining with an antibody towards tau (AT100). Scale bar represents 10 μm.

The Example Compounds' selectivity towards aggregated tau species was also verified with co-staining experiments using the tau-specific antibody AT-100 (FIG. 2 shows the results for Example Compounds 3a, 3b, 3c, 3d and 8a). Each of Example Compounds 3a, 3b, 3c, 3d, 3e, 3f, 3g, 3h, 3i, 3j, 3k, 3m, 3n, 3o, 3p, 3q, 3r, 3s, 3t, 3u and 8a displayed overlap with the AT100 staining (see arrows of FIG. 2 for results for Example Compounds 3a, 3b, 3c, 3d and 8a), verifying that the compounds stained tau pathology in brain tissue sections with AD pathology. All the Example Compounds 3a, 3b, 3c, 3d, 3e, 3f, 3g, 3h, 3i, 3j, 3k, 3m, 3n, 3o, 3p, 3q, 3r, 3s, 3t, 3u and 8a labelled both immune-positive NFTs and dystrophic neurites. These results are summarized in Table 2. FIG. 2 shows the results for Example Compounds 3a, 3b, 3c, 3d and 8a.

TABLE 2

| Example number or comparative example numbers | Fluorescence from tested compound observed | Fluorescence from AT-100 observed | Overlap between Fluorescence from tested compound and fluorescence from AT-100 observed |
|---|---|---|---|
| Example Compound 3a | yes | yes | yes |
| Example Compound 3b | yes | yes | yes |
| Example Compound 3c | yes | yes | yes |
| Example Compound 3d | yes | yes | yes |
| Example Compound 3e | yes | yes | yes |
| Example Compound 3f | yes | yes | yes |
| Example Compound 3g | yes | yes | yes |
| Example Compound 3h | yes | yes | yes |
| Example Compound 3i | yes | yes | yes |
| Example Compound 3j | yes | yes | yes |
| Example Compound 3k | yes | yes | yes |
| Example Compound 3m | yes | yes | yes |
| Example Compound 3n | yes | yes | yes |
| Example Compound 3o | yes | yes | yes |
| Example Compound 3p | yes | yes | yes |
| Example Compound 3q | yes | yes | yes |
| Example Compound 3r | yes | yes | yes |
| Example Compound 3s | yes | yes | yes |
| Example Compound 3t | yes | yes | yes |
| Example Compound 3u | yes | yes | yes |
| Example Compound 8a | yes | yes | yes |

(ii) Optical Characterization of the Compounds of the Invention Bound to Neurofibrillary Tangles Reagents and Procedure Stock solutions of Example Compound 3a, Example Compound 3b, Example Compound 3c, Example Compound 3d and Example Compound 8a (1.5 mM in DMSO) were diluted to 300 nM in phosphate buffered saline (PBS, 10 mM phosphate, 140 mM NaCl, 2.7 mM KCl, pH 7.4) or DMSO. Excitation and emission spectra of the compounds were collected using an Infinite M1000 Pro microplate reader (Tecan, Männedorf, Switzerland).

Results of Optical Characterization of the Compounds of the Invention Bound to Neurofibrillary Tangles In order to elucidate the tau selective staining of the compounds of the invention in more detail, the photo-physical properties of the Example Compounds 3a, 3b, 3c, 3d and 8a bound to tau deposits were evaluated in comparison to the compounds dissolved in DMSO and further diluted in DMSO or PBS.

Figure 4:
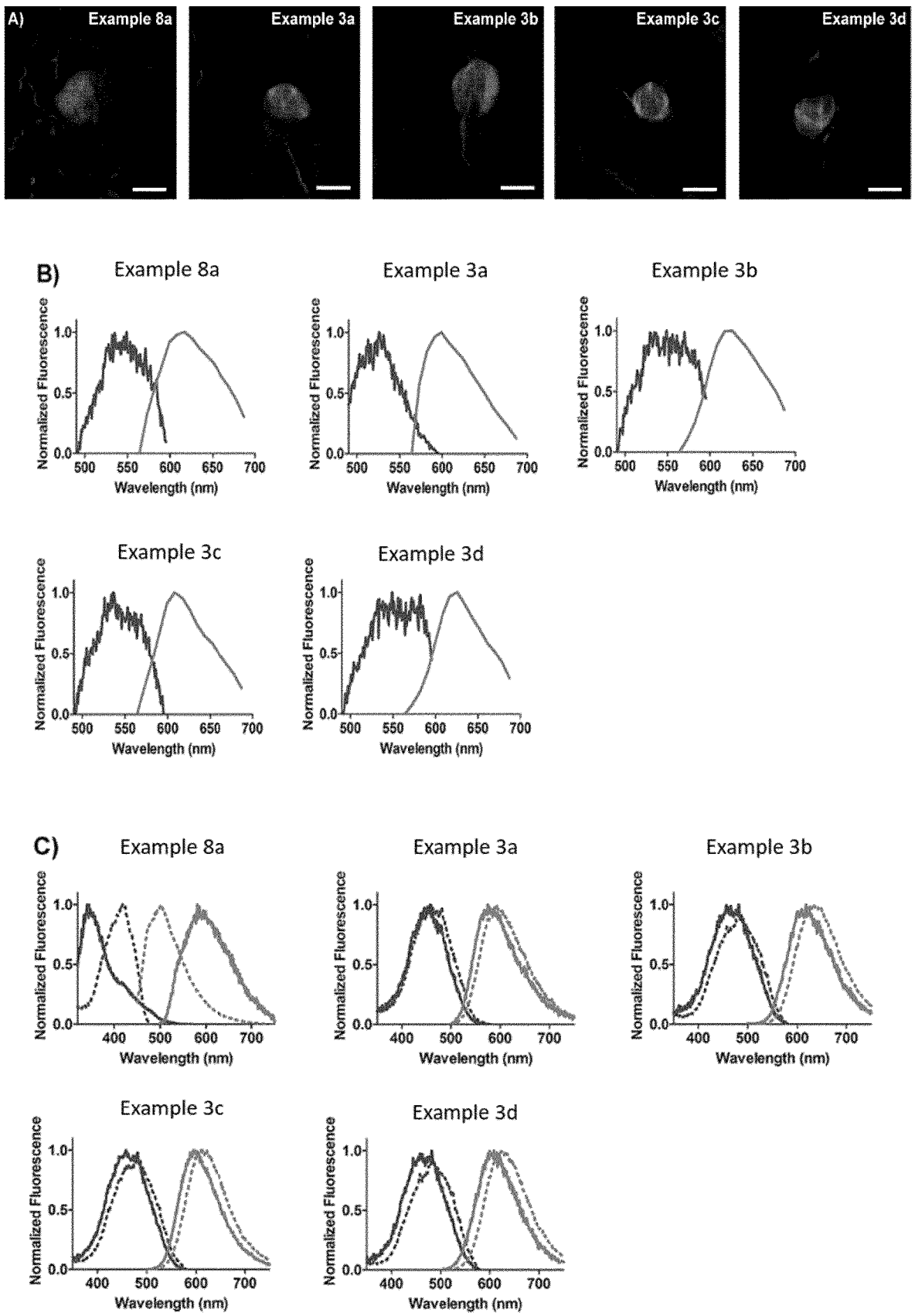
FIG. 4 shows the excitation and emission characteristics of the Example Compounds 3a, 3b, 3c, 3d and 8a bound to NFTs or diluted in DMSO and PBS: (A) Fluorescence images of Example Compounds 3a, 3b, 3c, 3d or 8a stained NFTs. Scale bar represent 10 μm. (B) Excitation (left curve) and emission (left curve) spectra from the Example Compounds 3a, 3b, 3c, 3d and 8a bound to NFTs. (C) Excitation (left curve) and emission (right curve) spectra from Example Compounds 3a, 3b, 3c, 3d or 8a dissolved in DMSO and further diluted in DMSO (dotted line) or in PBS pH 7.4 (solid line) to a final concentration of 300 nM.

Representative spectra from Example Compounds 3a, 3b, 3c, 3d and 8a stained NFTs are shown in FIG. 4. All the compounds displayed an emission spectrum with a maximum around 600 to 630 nm and an excitation spectrum with a maximum around 525 to 550 nm (FIG. 4B and FIG. 5), suggesting that all the compounds bind to the tau deposits in a similar fashion. Furthermore, when analyzing the excitation and emission profiles of the compounds in DMSO (lines) or PBS (dotted lines), the photo-physical behavior was strikingly different (FIG. 4C and FIG. 5). Example Compound 8a exhibited a solvatochromatic behavior rendering a blue-shifted excitation spectrum, as well as a red-shifted emission spectrum, when switching solvent from DMSO to PBS, whereas the other Example Compounds 3a, 3b, 3c, and 3d showed similar spectra in both solvents. Notably, all the compounds displayed a pronounced red-shift of the excitation maxima when bound to NFTs compared to the maxima obtained in the different solvents. Thus, upon interaction with the NFT, the compounds of the invention adopt a distinct conformation that induce a specific optical signature from the compounds. In summary, upon interaction with NFTs, all the compounds of the invention tested displayed distinct excitation and emission-spectra.

(iii) Comparison of Compounds of the Invention with q-FTAA-CN and PBB3

Reagents and Procedure q-FTAA-CN and PBB3 may be synthesized as previously described (M. Maruyama, et al, *Neuron* 2013, 79, 1094-1108; and M. Bäck, et al, *Chemistry*. 2016, 22, 18335-18338).

Co-staining with the Compounds and P883 or q-FTAA-CN

Frozen brain sections (20 µm) were fixed in 96% EtOH, rehydrated in 50% EtOH and de-ionized water and then incubated in phosphate buffered saline (PBS, 10 mM phosphate, 140 mM NaCl, 2.7 mM KCl, pH 7.4) for 10 min. Solutions containing 100 nM PBB3 and 100 nM Example Compound 3b or 100 nM q-FTAA-CN and 100 nM Example Compound 3a in PBS were added to the sections. After 30 min, the sections were washed with PBS and mounted with Dako fluorescent mounting medium (Dako Cytomation, Glostrup, Denmark). The mounting medium was allowed to solidify over night before collecting emission spectra of the compounds bound to misfolded Aβ and tau using an inverted LSM 780 confocal microscope (Carl Zeiss, Oberkochen, Germany) with excitation wavelengths at 405 nm (PBB3 and q-FTAA-CN) and 561 nm (Example Compound 3a and Example Compound 3b).

Compound Staining of Tissue Sections Pre-Incubated with P883 or q-FTAA-CN

Frozen brain sections (20 µm) were fixed in 96% EtOH, rehydrated in 50% EtOH and de-ionized water and then incubated in phosphate buffered saline (PBS, 10 mM phosphate, 140 mM NaCl, 2.7 mM KCl, pH 7.4) for 10 min. The sections were stained with solutions containing 1 µM PBB3 or 1 µM q-FTAA-CN in PBS for 30 min and after rinsing three times with PBS, the sections was stained with a solution containing 10 nM Example Compound 3b. After 30 min, the sections were washed with PBS and mounted with Dako fluorescent mounting medium (Dako Cytomation, Glostrup, Denmark). The mounting medium was allowed to solidify over night before collecting emission spectra of the compounds bound to misfolded Aβ and tau using an inverted LSM 780 confocal microscope (Carl Zeiss, Oberkochen, Germany) with excitation wavelengths at 405 nm (PBB3 and q-FTAA-CN) and 561 nm (Example Compound 3b).

Compound Staining of Tissue Sections with P883

Frozen brain sections (20 µm) were fixed in 96% EtOH, rehydrated in 50% EtOH and de-ionized water and then incubated in phosphate buffered saline (PBS, 10 mM phosphate, 140 mM NaCl, 2.7 mM KCl, pH 7.4) for 10 min. The sections were stained with solutions containing 100 nM PBB3 in PBS for 30 min and after rinsing three times with PBS mounted with Dako fluorescent mounting medium (Dako Cytomation, Glostrup, Denmark). The mounting medium was allowed to solidify over night before collecting emission spectra of the compound bound to misfolded Aβ and tau using an inverted LSM 780 confocal microscope (Carl Zeiss, Oberkochen, Germany) with excitation wavelengths at 405 nm (PBB3).

Results of Comparison of Compounds of the Invention with q-FTAA-CN and PBB3

To further investigate the binding mode of the compounds of the invention to tau deposits, tissue sections with AD pathology were simultaneously stained with 100 nM of Example Compound 3a and 100 nM of q-FTAA-CN. When using Example Compound 3a and q-FTAA-CN a clear distinction between Aβ and tau deposits was achieved. As shown in FIG. 7, q-FTAA-CN fluorescence was observed from Aβ deposits (arrow-heads) whereas tau aggregates (arrows) displayed Example Compound 3a fluorescence (. Thus, as previously reported (M. Bäck, et al, *Chemistry*. 2016, 22, 18335-18338), at this concentration (100 nM), q-FTAA-CN selectively labelled Aβ deposits. In addition, tau pathology could be identified by the spectral signature of Example Compound 3a (See FIG. 7A-D). Thus, by applying two thiophene-based compounds, q-FTAA-CN and Example Compound 3a, specific optical assignment of the two pathological hallmarks of Alzheimer's disease is achieved. These results shown in FIG. 7A-C are also shown in Table 3.

TABLE 3

| Figure No. | Fluorescence from Example 3a observed | Fluorescence from q-FTAA-CN observed | Overlap between Fluorescence from Example 3a and fluorescence from q-FTAA-CN |
|---|---|---|---|
| 7A | yes | yes | no |
| 7B | yes | yes | no |
| 7C | yes | yes | no |

A similar staining experiment using 100 nM of a compound of the invention and 100 nM of PBB3 was performed. As the previously reported in vitro fluorescence staining of AD brain sections with PBB3 was performed under different conditions (10-3% ligands dissolved in 50% ethanol for 1 hour at room temperature) (M. Maruyama, et al, Higuchi. *Neuron* 2013, 79, 1094-1108) compared to the conditions for the present experiment, staining experiments with only 100 nM PBB3 in PBS pH 7.4 was first conducted. With this staining procedure, PBB3 evidently labelled both Aβ and tau deposits, as characteristic fluorescence was observed from both these aggregated species (as shown in FIG. 6A, PBB3 displayed staining of both Aβ (arrow heads) and tau aggregates (arrows)). Due to the spectral properties of PBB3 (FIG. 6B), Example Compound 3b was selected as the thiophene-based ligand for being simultaneously used with PBB3.

As shown in FIG. 7E, when using the simultaneous combination of dyes of 100 nM PBB3 and 100 nM Example Compound 3b, Aβ deposits were visualized by the fluorescence from PBB3 (small arrow-heads), whereas tau deposits, NFTs and dystrophic neurites, displayed characteristic emission from Example Compound 3b (arrows). Thus, under these staining conditions, Example Compound 3b showed a higher selectivity and most likely a higher affinity for tau deposits than PBB3. This result is also shown in Table 4, below.

It also appears these ligands compete for the same binding site to the tau deposits. To verify this, tissue sections were first incubated in PBS or PBS with 1 µM of PBB3 for 1 hour prior to staining with 10 nM of Example Compound 3b. In the section pre-incubated PBB3, both the Aβ and tau deposits exhibited strong PBB3 fluorescence, whereas no observable Example Compound 3b fluorescence was obtained from the tau pathology (see FIG. 7F—PBB3 fluorescence was observed from both Aβ deposits (small arrow-heads) and tau aggregates (arrows) whereas no Example Compound 3b fluorescence was observed. In contrast, for the section pre-incubated in PBS, Example Compound 3b fluorescence was observed from the tau aggregates (see arrows in FIG. 7G)). Hence, the tau staining of Example Compound 3b was abolished by pre-incubating the sections with a 100-fold excess of PBB3, verifying that these two ligands shared a similar mode of binding to tau aggregates. These results are also shown in Table 4, below.

TABLE 4

| Figure No. | Fluorescence from Example Compound 3b observed | Fluorescence from PBB3 observed | Overlap between Fluorescence from Example Compound 3b and fluorescence from PBB3 |
|---|---|---|---|
| 7E | yes | yes | no |
| 7F | no | yes | n/a |
| 7G | yes | n/a | n/a |

As it has been reported that q-FTAA-CN also stained NFTs when using micro-molar concentrations of ligand for histological staining (M. Bäck, et al, *Chemistry*. 2016, 22, 18335-18338), similar competition experiments as described above were also performed using q-FTAA-CN and Example Compound 3b. As shown in FIG. 7H, q-FTAA-CN fluorescence was observed from both Aβ deposits (small arrow-heads) and tau aggregates whereas Example Compound 3b fluorescence was observed from the tau aggregates (arrows).

Therefore, q-FTAA labelled both Aβ deposits and NFTs (FIG. 7H). In addition, even though the section was pre-incubated with 1 μM q-FTAA-CN, the characteristic Example Compound 3b fluorescence from the NFTs could easily be observed from the q-FTAA-CN positive NFTs as well as from q-FTAA-CN negative dystrophic neurites (FIG. 7H). Hence, q-FTAA-CN and Example Compound 3b most likely have alternative modes of binding to tau aggregates. Previous studies have suggested that anionic oligothiophenes, including q-FTAA-CN, have a similar mode of binding to protein aggregates as Congo red and related analogues (M. Bäck, et al, *Chemistry*. 2016, 22, 18335-18338; U.S. Herrmann, et al, *Sci. Transl. Med.* 2015, 7, 299ra123).

TABLE 5

| Figure No. | Fluorescence from Example Compound 3b observed | Fluorescence from q-FTAA-CN observed | Overlap between Fluorescence from Example Compound 3b and fluorescence from q-FTAA-CN |
|---|---|---|---|
| 7H | yes | yes | yes |

Summary of Results

The results of the above experiments (i), (ii) and (iii) show that the compounds of the invention are selective ligands for tau deposits: when brain tissue sections with Alzheimer's disease pathology were stained in combination with an antibody (4G8) for Aβ pathology, none of Example Compounds 3a, 3b, 3c, 3d, 3e, 3f, 3g, 3h, 3i, 3j, 3k, 3m, 3n, 3o, 3p, 3q, 3r, 3s, 3t, 3u or 8a showed correlation with the antibody staining. Instead, the staining pattern observed from each compound resembled classical tau pathology, NFTs and dystrophic neurites. In addition, when brain tissue sections with Alzheimer's disease pathology were stained in combination with q-FTAA-CN, known to be selective for Aβ deposits, Example Compound 3a showed no correlation with the q-FTAA-CN staining, and a clear distinction between Aβ and tau deposits was achieved. (Comparative examples 1 to 4 either showed no selectivity (Comparative Example 3), selectivity for Aβ (Comparative Example 1), or no staining (Comparative Example 2 and 4) when brain tissue sections with Alzheimer's disease pathology were stained in combination with 4G8.)

Further, when brain tissue sections with Alzheimer's disease pathology were stained in combination with a tau-specific antibody (AT-100), Compounds 3a, 3b, 3c, 3d, 3e, 3f, 3g, 3h, 3i, 3j, 3k, 3m, 3n, 3o, 3p, 3q, 3r, 3s, 3t, 3u and 8a all displayed overlap with the AT100 antibody staining. In addition, when brain tissue sections with Alzheimer's disease pathology were simultaneously stained with Example Compound 3b and PBB3 (a compound known to label both Aβ deposits and tau deposits), Aβ deposits were visualized by the fluorescence from PBB3, whereas tau deposits displayed characteristic emission from Example Compound 3b. Thus, under those staining conditions Example Compound 3b showed a higher selectivity (and most likely a higher affinity) for tau deposits than PBB3. In another staining experiment where brain tissue sections with Alzheimer's disease pathology were exposed to PBB3 before Example Compound 3b, it was shown that PBB3 and Example Compound 3b compete for the same tau deposit binding site.

The compounds of the present invention may be defined according to the following clauses:

§ 1. A compound of formula (I) or a pharmaceutically acceptable salt, ester, amide or carbamate thereof, or a salt of such an ester, amide or carbamate,

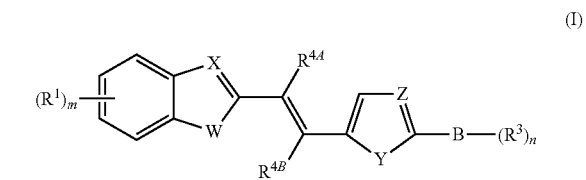

(I)

wherein
W is S, O or Se;
X is N or $N^+\text{—}R^2$;
Y is S or O;
Z is CH or N;
or Y is Se and Z is CH;
B is a 6 to 10 membered aromatic carbocycle or a 5 to 10 membered aromatic heterocycle having 1 to 3 heteroatoms selected from the group consisting of S, N, O and Se;
each $R^1$ is independently selected from the group consisting of O—$C_{1-6}$alkyl, —O-monohalo$C_{1-6}$alkyl, —O-dihalo$C_{1-6}$alkyl, —O-trihalo$C_{1-6}$alkyl, $C_{1-6}$alkyl, monohalo$C_{1-6}$alkyl, dihalo$C_{1-6}$alkyl, trihalo$C_{1-6}$alkyl, OH, F, Cl, Br, I, and CN;
$R^2$ is selected from the group consisting of $C_{1-6}$alkyl, monohalo$C_{1-6}$alkyl, dihalo$C_{1-6}$alkyl, trihalo$C_{1-6}$alkyl, and $C(O)C_{1-6}$alkyl;
each $R^3$ is independently selected from the group consisting of —O—$C_{1-6}$alkyl, —O-monohalo$C_{1-6}$alkyl, —O-dihalo$C_{1-6}$alkyl, —O-trihalo$C_{1-6}$alkyl, —$(CH_2)_p$—O—$C_{1-6}$alkyl, —$(CH_2)_q$—C(O)—$C_{1-6}$alkyl, —$(CH_2)_r$—C(O)—O—$C_{1-6}$alkyl, —$(CH_2)_s$—N$(R^5)_2$, OH, F, Cl, Br, I, —CN, —$C_{1-6}$alkyl, monohalo$C_{1-6}$alkyl, dihalo$C_{1-6}$alkyl, and trihalo$C_{1-6}$alkyl;
$R^{4A}$ and $R^{4B}$ are independently selected from the group consisting of H, OH, F, Cl, Br, I, $C_{1-6}$alkyl, monohalo$C_{1-6}$alkyl, dihalo$C_{1-6}$alkyl, trihalo$C_{1-6}$alkyl, O—$C_{1-6}$alkyl, —O-monohalo$C_{1-6}$alkyl, —O-dihalo$C_{1-6}$alkyl, and —O-trihalo$C_{1-6}$alkyl;
each $R^5$ is independently selected from the group consisting of H and $C_{1-6}$alkyl;
m is 0, 1, 2 or 3; n is 0, 1, 2 or 3;

p is 1, 2 or 3, q is 0, 1, or 2; r is 0, 1, or 2; and s is 0, 1, 2, or 3.

§ 2. The compound of clause 1, wherein the compound of formula (I) is not a compound selected from the group consisting of § 3. The compound of clause 1 or 2, wherein the compound of formula (I) is not a compound selected from the group consisting of:

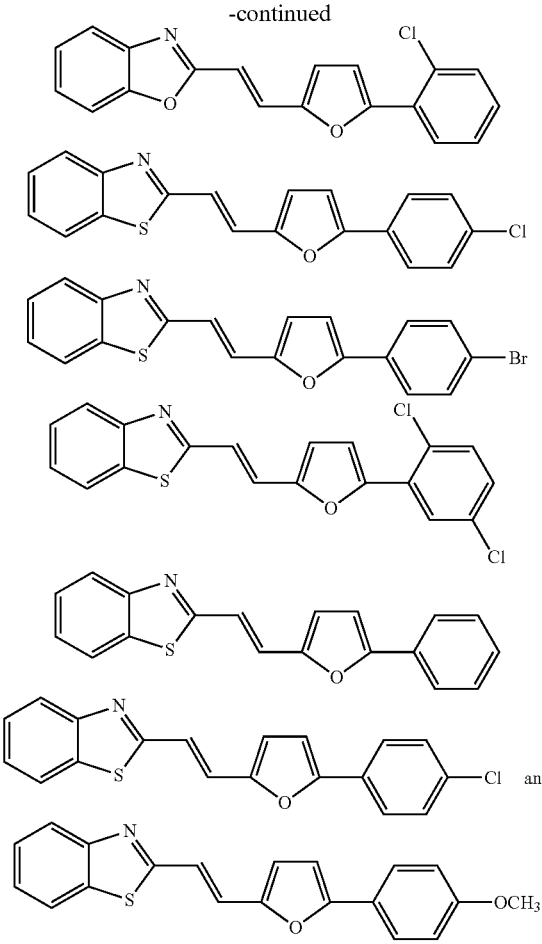

The compound as defined in any one of clauses 1 to 3, wherein the compound of formula (I) comprises one or more radioisotopes selected from the group consisting of tritium ($^3$H), carbon-11 ($^{11}$C), nitrogen-13 ($^{13}$N), oxygen-15 ($^{15}$O), fluorine-18 ($^{18}$F), iodine-120 ($^{120}$I) iodine-123 ($^{123}$I) and iodine-125 ($^{125}$I); and preferably one or more radioisotopes selected from the group consisting of carbon-11 ($^{11}$C), nitrogen-13 ($^{13}$N), oxygen-15 ($^{15}$O), fluorine-18 ($^{18}$F) and iodine-120 ($^{120}$I)

§ 5. The compound as defined in any one of clauses 1 to 4, wherein B is a 5 to 10 membered aromatic heterocycle having 1 to 3 heteroatoms selected from the group consisting of S, N, O and Se.

§ 6. A compound as defined in any one of clauses 1 to 5, wherein each $R^1$ is independently selected from the group consisting of —O—$C_{1-6}$alkyl, —O-monohalo$C_{1-6}$alkyl, monohalo$C_{1-6}$alkyl, trihalo$C_{1-6}$alkyl, OH, F, Br, I, and CN.

§ 7. A compound as defined in any one of clauses 1 to 6, wherein Y is S (and preferably Z is CH); or Y is Se and Z is CH; and more preferably wherein Y is S.

§ 8. A compound as defined in any one of clauses 1 to 7, wherein s is 1, 2, or 3 and each $R^3$ is independently selected from the group consisting of —O—$C_{1-6}$alkyl, —O-monohalo$C_{1-6}$alkyl, —O—$(CH_2)_p$—O—$C_{1-6}$alkyl, —$(CH_2)_q$—C(O)—$C_{1-6}$alkyl, —$(CH_2)_r$—C(O)—O—$C_{1-6}$alkyl, —$(CH_2)_s$—$N(R^5)_2$, —N($C_{1-6}$alkyl)H, N($C_{1-6}$alkyl)$_2$, OH, F, Cl, Br, I, —CN, monohalo$C_{1-6}$alkyl, dihalo$C_{1-6}$alkyl, and trihalo$C_{1-6}$alkyl;

§ 9. A compound as defined in any one of clauses 1 to 8, wherein $R^{4A}$ is selected from the group consisting of H, OH, F, Cl, Br, I, $C_{2-6}$alkyl, monohalo$C_{1-6}$alkyl, trihalo$C_{1-6}$alkyl, O—$C_{1-6}$alkyl, —O-monohalo$C_{1-6}$alkyl, —O-dihalo$C_{1-6}$alkyl, and —O-trihalo$C_{1-6}$alkyl; and $R^{4B}$ is selected from the group consisting of H, OH, F, Cl, Br, I, $C_{1-6}$alkyl, monohalo$C_{1-6}$alkyl, dihalo$C_{1-6p}$alkyl, —O-monohalo$C_{1-6}$alkyl, —O-dihalo$C_{1-6}$alkyl, and —O-trihalo$C_{1-6}$alkyl.

§ 10. The compound of any one of clauses 1 to 9, wherein compound of formula (I) is a compound of formula (Ia)

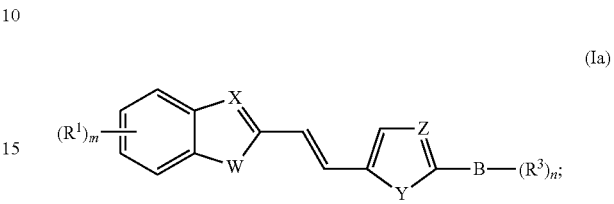

or wherein the compound of formula (I) is the compound of formula (Ib),

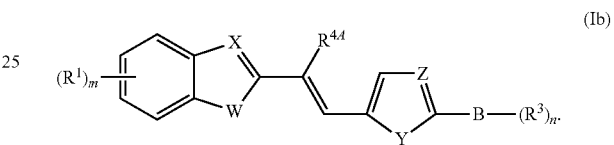

wherein $R^{4A}$ is selected from the group consisting of H, OH, F, Cl, Br, I, $C_{1-6}$alkyl (preferably $C_{2-6}$alkyl), monohalo$C_{1-6}$alkyl, dihalo$C_{1-6}$alkyl, trihalo$C_{1-6}$alkyl, O—$C_{1-6}$alkyl, —O-monohalo$C_{1-6}$alkyl, —O-dihalo$C_{1-6}$alkyl, and —O-trihalo$C_{1-6}$alkyl; or wherein the compound of formula (I) is the compound of formula (Ic),

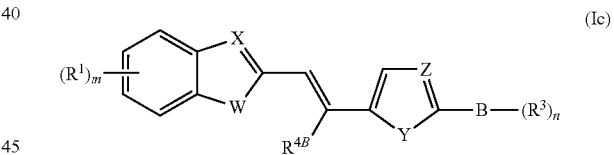

wherein $R^{4B}$ is selected from the group consisting of H, OH, F, Cl, Br, I, $C_{1-6}$alkyl, monohalo$C_{1-6}$alkyl, dihalo$C_{1-6}$alkyl, trihalo$C_{1-6}$alkyl, O—$C_{1-6}$alkyl, —O-monohalo$C_{1-6}$alkyl, —O-dihalo$C_{1-6}$alkyl, and —O-trihalo$C_{1-6}$alkyl.

§ 11. The compound as defined in any one of clauses 1 to 10, wherein W is S or O, and preferably S.

§ 12. The compound as defined in any one of clauses 1 to 11, wherein X is $N^+$—$R^2$.

§ 13. The compound as defined in any one of clauses 1 to 12 wherein m is 0 or 1, i.e. wherein the compound of formula (I) is selected from the group consisting of

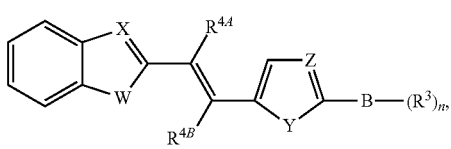

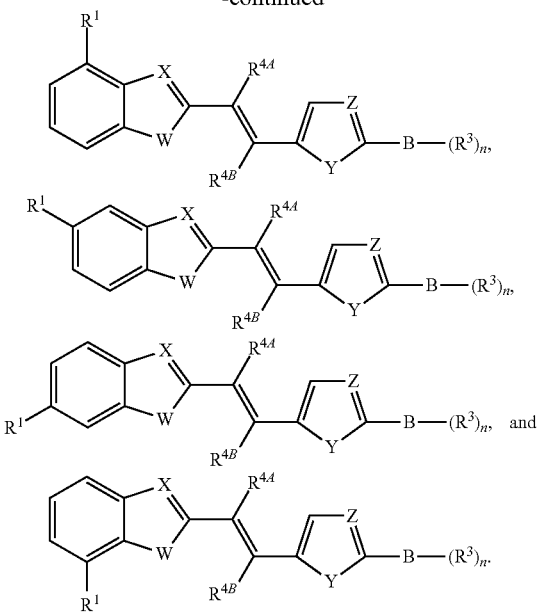

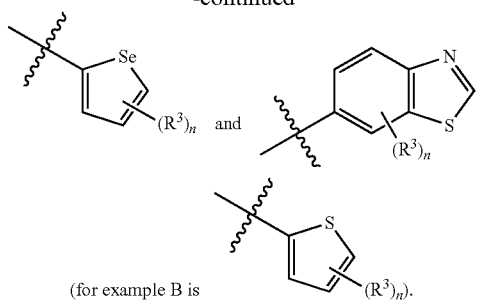

(for example B is 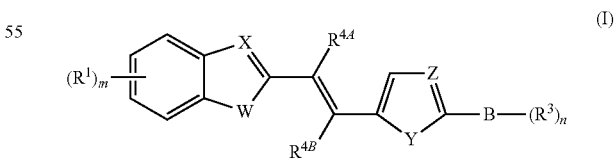 ).

§ 16. The compound as defined in any one of clauses 1 to 15, wherein each $R^3$ is independently selected from the group consisting of O—$C_{1-4}$alkyl, —O-monofluoro$C_{1-4}$alkyl, —O-difluoro$C_{1-4}$alkyl, —O-trifluoro$C_{1-4}$alkyl, —$(CH_2)_p$—O—$C_{1-4}$alkyl, —$(CH_2)_q$—C(O)—$C_{1-4}$alkyl, —$(CH_2)_r$—C(O)—O—$C_{1-4}$alkyl, —$N(R^5)_2$ (wherein preferably one $R^5$ is $C_{1-6}$alkyl (for example $C_{1-4}$alkyl), and the other $R^5$ is H or $C_{1-6}$alkyl (for example $C_{1-4}$alkyl); and even more preferably the other $R^5$ is H), F, Cl, Br, I, and —CN; p is 1; q is 0 or 1; r is 0 or 1; and each $R^5$ is independently selected from the group consisting of H and $C_{1-4}$alkyl.

The compounds defined in clauses 1 to 16 may be provided in a pharmaceutical or diagnostic composition together with a pharmaceutically suitable carrier, and optioanlly with an additional active ingredient, for example an additional therapeutic agent or an additional diagnostic agent. The compounds defined in clauses 1 to 16 (or pharmaceutical or diagnostic composition comprising such compounds) may be used in any use or method defined in the present disclosure, for example: for use as a diagnostic agent wherein the compound comprises one or more radioisotopes selected from $^3H$, $^{11}C$, $^{13}N$, $^{15}O$, $^{18}F$, $^{120}I$, $^{123}I$, and $^{125}I$; for use for the detection of tau deposits; for use as a diagnostic agent in the diagnosis or monitoring of progression of a disease or disorder described herein; for use as a medicament; for use in the prevention or treatment of a disease or disorder described herein; in a method of diagnosing a patient or monitoring disease progression in a patient comprising administering a compound to the patient, wherein the compound of formula (I) comprises one or more radioisotopes selected from $^3H$, $^{11}C$, $^{13}N$, $^{15}O$, $^{18}F$, $^{120}I$, $^{123}I$, and $^{125}I$; in method of diagnosing or monitoring of progression.

The invention claimed is:

1. A compound of formula (I) or a pharmaceutically acceptable salt, ester, amide or carbamate thereof, or a salt of such an ester, amide or carbamate,

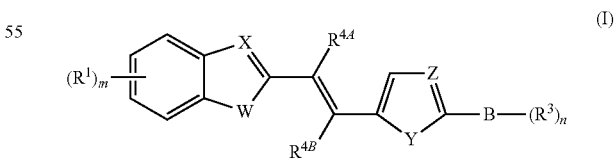

(I)

§ 14. The compound as defined in any one of clauses 1 to 13, wherein B is a 5 or 6 membered monocyclic aromatic heterocycle having 1 to 3 heteroatoms selected from the group consisting of S, N, O and Se; or a 9 or 10 membered bicyclic aromatic heterocycle having 1 to 3 heteroatoms selected from the group consisting of S, N, O and Se; and preferably wherein B is a 5 or 6 membered monocyclic aromatic heterocycle having 1 or 2 heteroatoms selected from the group consisting of S, N, and O (for example, B is selected from the group consisting of furanyl, pyrrolyl, imidazolyl, imidazolyl, pyridinyl, pyrimidinyl, pyridazinyl, pyrazinyl, thiophenyl, thiophenyl, isoxazolyl, dioxazolyl, thiazolyl, and isathiazolyl, and preferably furanyl or thiophenyl or pyridinyl); and more preferably B is a 5 or 6 membered monocyclic aromatic heterocycle having 1 or 2 heteroatoms (preferably 1 heteroatom) selected from the group consisting of S and N (for example thiophenyl or pyridinyl).

§ 15. The compound as defined in any one of clauses 1 to 14, wherein B is selected from the group consisting of:

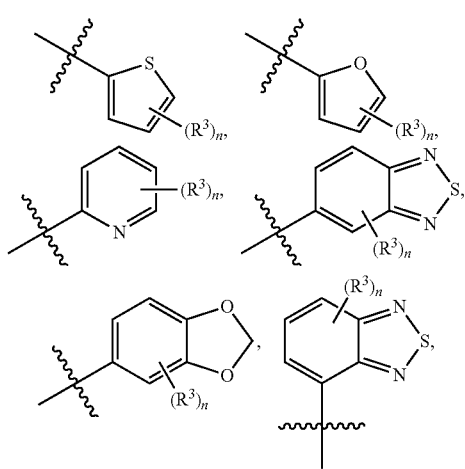

wherein
W is S, O or Se;
X is N or $N^+$—$R^2$;
Y is S or O;
Z is CH or N;
or Y is Se and Z is CH;

B is selected from the group consisting of:

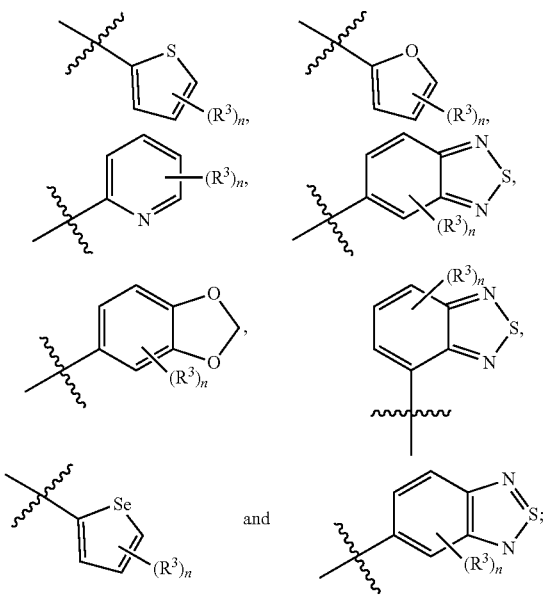

and each R[1] is independently selected from the group consisting of —O—$C_{1-6}$alkyl, —O—monohalo$C_{1-6}$alkyl, —O-dihalo$C_{1-6}$alkyl, —O-trihalo$C_{1-6}$alkyl, $C_{1-6}$alkyl, monohalo$C_{1-6}$alkyl, dihalo$C_{1-6}$alkyl, trihalo$C_{1-6}$alkyl, OH, F, Br, I, and CN;

R[2] is selected from the group consisting of $C_{1-6}$alkyl, monohalo$C_{1-6}$alkyl, dihalo$C_{1-6}$alkyl, trihalo$C_{1-6}$alkyl, and C(O)$C_{1-6}$alkyl;

each R[3] is independently selected from the group consisting of —O—$C_{1-6}$alkyl, —O-monohalo$C_{1-6}$alkyl, —O-dihalo$C_{1-6}$alkyl, —O-trihalo$C_{1-6}$alkyl, —(CH$_2$)$_p$—O—$C_{1-6}$alkyl, —(CH$_2$)$_q$—C(O)—$C_{1-6}$alkyl, —(CH$_2$)$_r$—C(O)—O—$C_{1-6}$alkyl, —(CH$_2$)$_s$—N(R[5])$_2$, OH, F, Cl, Br, I, —CN, —$C_{1-6}$alkyl, monohalo$C_{1-6}$alkyl, dihalo$C_{1-6}$alkyl, and trihalo$C_{1-6}$alkyl;

R[4A] and R[4B] are independently selected from the group consisting of H, OH, F, Cl, Br, I, $C_{1-6}$ alkyl, monohalo$C_{1-6}$alkyl, dihalo$C_{1-6}$alkyl, trihalo$C_{1-6}$alkyl, O—$C_{1-6}$ alkyl, —O-monohalo$C_{1-6}$alkyl, —O-dihalo$C_{1-6}$alkyl, and —O-trihalo$C_{1-6}$alkyl;

each R[5] is independently selected from the group consisting of H and $C_{1-6}$alkyl;

m is 0, 1, 2 or 3; n is 0, 1, 2 or 3;

p is 1, 2 or 3; q is 0, 1, or 2; r is 0, 1, or 2; and s is 0, 1, 2, or 3.

2. The compound of claim 1, wherein the compound of formula (I) comprises one or more radioisotopes selected from the group consisting of tritium ($^3$H), carbon-11 ($^{11}$C), nitrogen-13 ($^{13}$N), oxygen-15 ($^{15}$O), fluorine-18 ($^{18}$F), iodine-120 $^{120}$(I), iodine-123 ($^{123}$I) and iodine-125 ($^{125}$I).

3. The compound as claimed in claim 1, wherein Y is S and Z is CH or N; or Y is Se and Z is CH.

4. The compound as claimed in claim 1, wherein R[4A] and R[4B] are H;

or wherein the compound of formula (I) is the compound of formula (Ib),

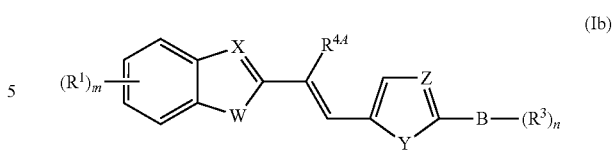

wherein R[4A] is selected from the group consisting of H, OH, F, Cl, Br, I, $C_{1-6}$ alkyl, monohalo$C_{1-6}$alkyl, dihalo$C_{1-6}$alkyl, trihalo$C_{1-6}$alkyl, O—$C_{1-6}$ alkyl, —O-monohalo$C_{1-6}$alkyl, —O-dihalo$C_{1-6}$alkyl, and —O-trihalo$C_{1-6}$alkyl; or wherein the compound of formula (I) is the compound of formula (Ic),

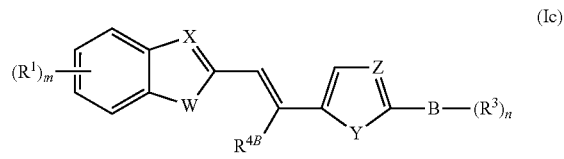

wherein R[4B] is selected from the group consisting of H, OH, F, Cl, Br, I, $C_{1-6}$ alkyl, monohalo$C_{1-6}$alkyl, dihalo$C_{1-6}$alkyl, trihalo$C_{1-6}$alkyl, O—$C_{1-6}$ alkyl, —O-monohalo$C_{1-6}$alkyl, —O-dihalo$C_{1-6}$alkyl, and —O-trihalo$C_{1-6}$alkyl.

5. The compound as claimed in claim 1, wherein W is S or O.

6. The compound as claimed in claim 1, wherein X is N$^+$—R[2].

7. The compound as claimed in claim 1, wherein m is 0 or 1.

8. The compound as claimed in claim 1, wherein each R[3] is independently selected from the group consisting of O—$C_{1-4}$alkyl, —O-monofluoro$C_{1-4}$alkyl, —O-difluoro$C_{1-4}$ alkyl, —O-trifluoro$C_{1-4}$alkyl, —(CH$_2$)$_p$—O—$C_{1-4}$alkyl, —(CH$_2$)$_q$—C(O)—$C_{1-4}$alkyl, —(CH$_2$)$_r$—C(O)—O—$C_{1-4}$ alkyl, —N(R[5])$_2$, F, Cl, Br, I, and —CN; p is 1; q is 0 or 1; r is 0 or 1; and each R[5] is independently selected from the group consisting of H and $C_{1-4}$alkyl.

9. The compound as claimed in claim 1, wherein the compound is selected from the group consisting of:

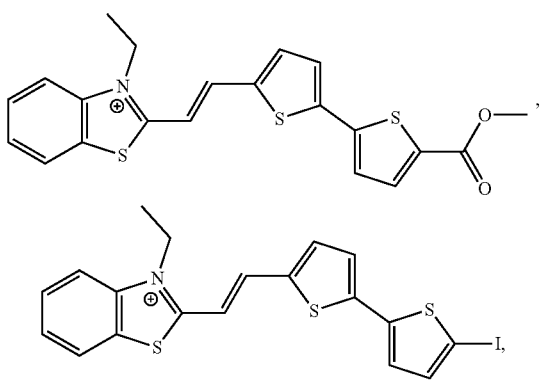

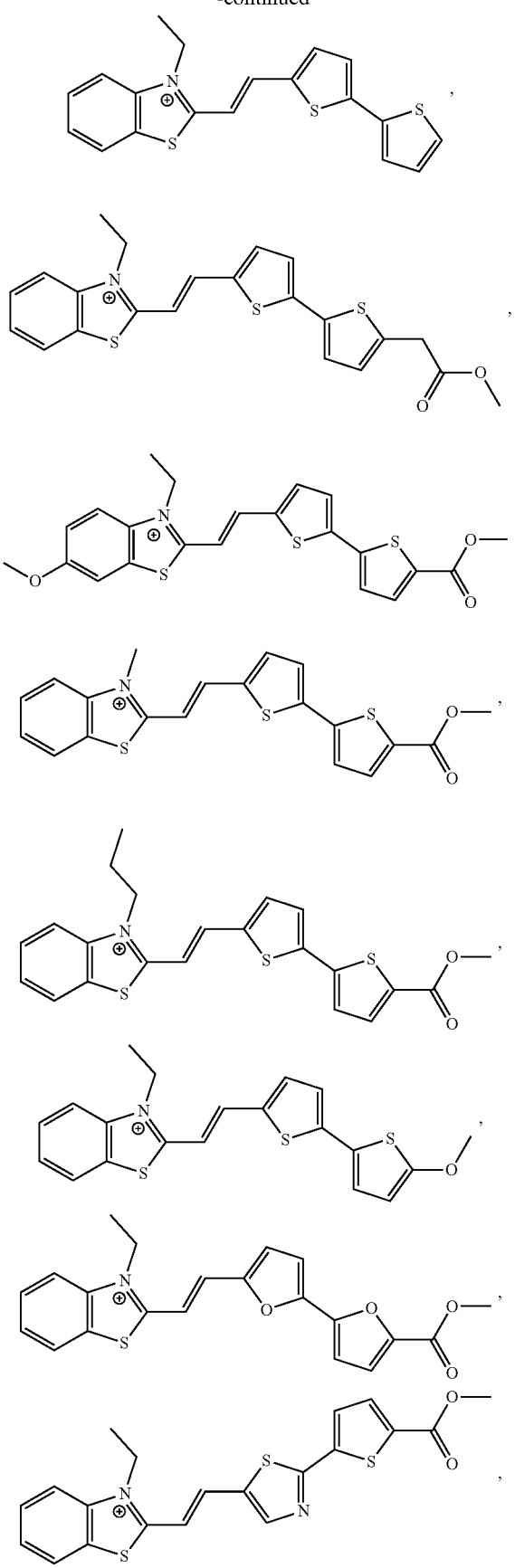
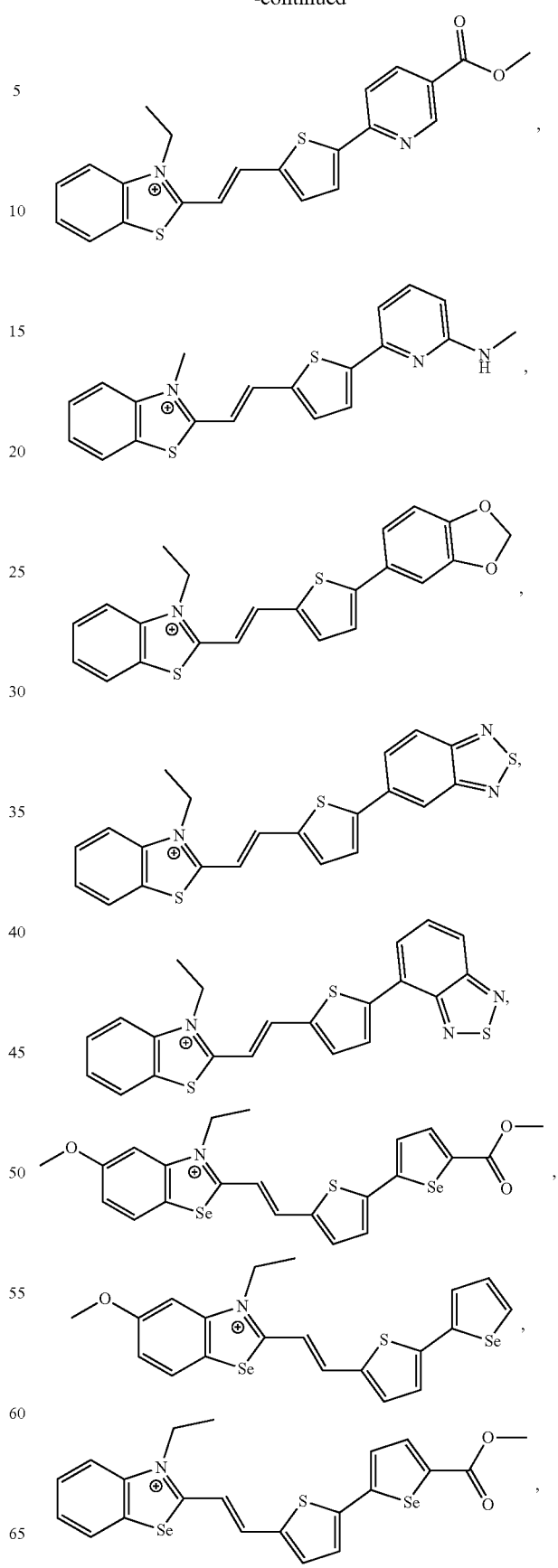

69
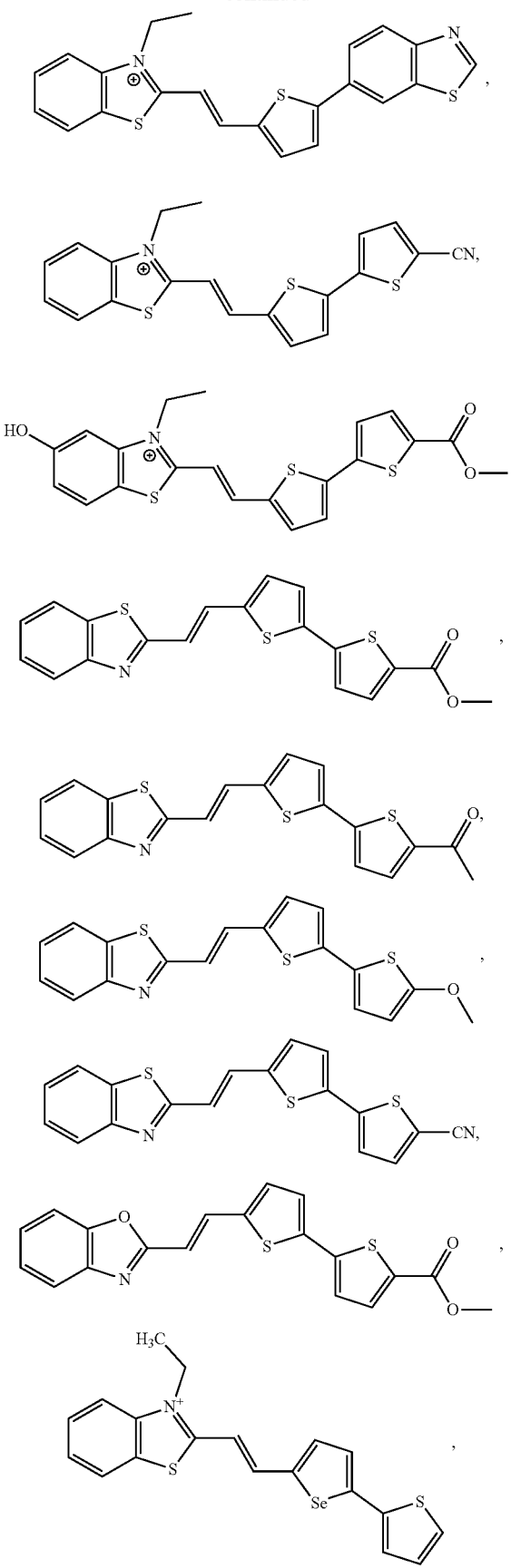
70
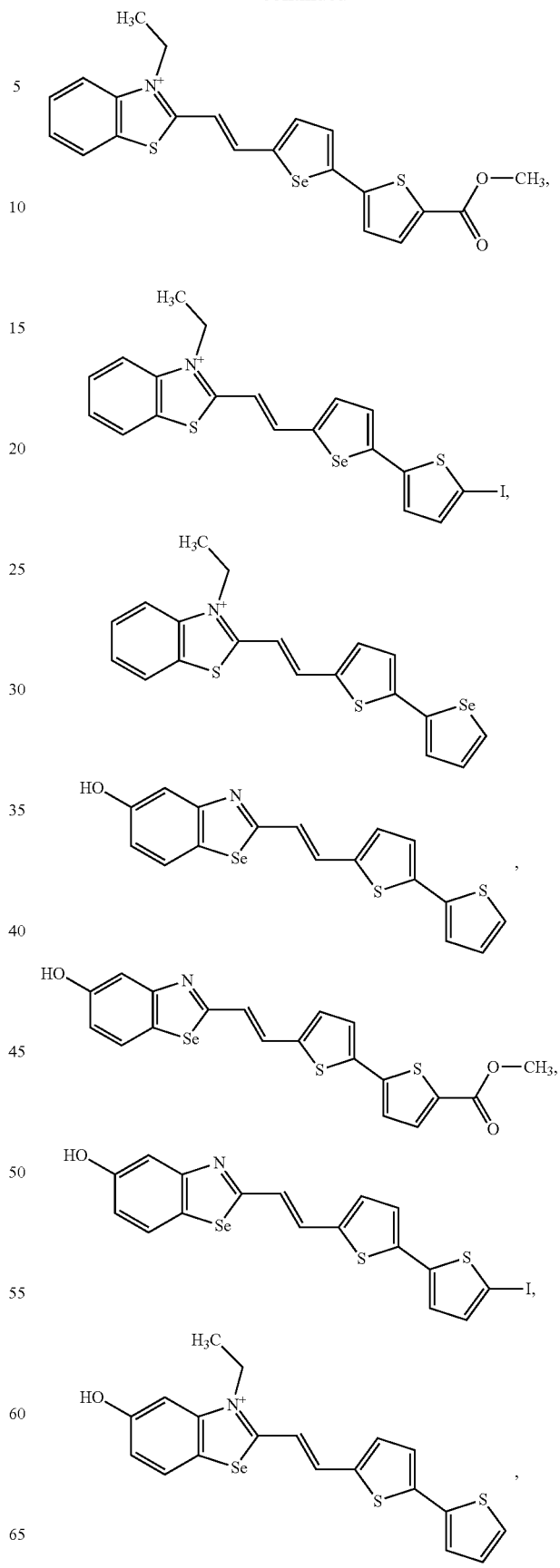

and where appropriate with a suitable counter-ion;

or a pharmaceutically acceptable salt, ester, amide or carbamate thereof, or a salt of such an ester, amide or carbamate; and wherein the compound of may optionally comprise one or more radioisotopes selected from tritium ($^3$H), carbon-11 ($^{11}$C) nitrogen-13 ($^{13}$N), oxygen-15 ($^{15}$O), fluorine-18 ($^{18}$F), iodine-120 ($^{120}$I) iodine-123 ($^{123}$I) and iodine-125 ($^{125}$I).

10. A pharmaceutical or diagnostic composition comprising a compound of formula (I) or a pharmaceutically acceptable salt, ester, amide or carbamate thereof, or a salt of such an ester, amide or carbamate, wherein W is S, O or Se;
X is N or N$^+$—R$^2$;
Y is S or O;
Z is CH or N;
or Y is Se and Z is CH;
B is selected from the group consisting of:

each R$^1$ is independently selected from the group consisting of —O—C$_{1-6}$alkyl, —O-monohaloC$_{1-6}$alkyl, —O-trihaloC$_{1-6}$alkyl, C$_{1-6}$alkyl, monohaloC$_{1-6}$alkyl, dihaloC$_{1-6}$alkyl, trihaloC$_{1-6}$alkyl, OH, F, Br, I, and CN;

R$^2$ is selected from the group consisting of C$_{1-6}$alkyl, monohaloC$_{1-6}$alkyl, dihaloC$_{1-6}$alkyl, trihaloC$_{1-6}$alkyl, and C(O)C$_{1-6}$alkyl;

each R$^3$ is independently selected from the group consisting of —O—C$_{1-6}$alkyl, —O-monohaloC$_{1-6}$alkyl, —O-trihaloC$_{1-6}$alkyl, —(CH$_2$)$_p$—O—C$_{1-6}$alkyl, —(CH$_2$)$_q$—C(O)—C$_{1-6}$alkyl, —(CH$_2$)$_r$—C(O)—O—C$_{1-6}$alkyl, —(CH$_2$)$_s$—N(R$^5$)$_2$, OH, F, Cl, Br, I, —CN, —C$_{1-6}$alkyl, monohaloC$_{1-6}$alkyl, dihaloC$_{1-6}$alkyl, and trihaloC$_{1-6}$alkyl;

R$^{4A}$ and R$^{4B}$ are independently selected from the group consisting of H, OH, F, Cl, Br, I, C$_{1-6}$ alkyl, monohaloC$_{1-6}$alkyl, dihaloC$_{1-6}$alkyl, trihaloC$_{1-6}$alkyl, O—C$_{1-6}$ alkyl, —O-monohaloC$_{1-6}$alkyl, —O-dihaloC$_{1-6}$alkyl, and —O-trihaloC$_{1-6}$alkyl;

each R$^5$ is independently selected from the group consisting of H and C$_{1-6}$alkyl;

m is 0, 1, 2 or 3; n is 0, 1, 2 or 3;

p is 1, 2 or 3, q is 0, 1, or 2; r is 0, 1, or 2; and s is 0, 1, 2 or 3;

together with a pharmaceutically suitable carrier.

11. A method for detecting tau deposits comprising using a compound of formula (I) or a pharmaceutically acceptable salt, ester, amide or carbamate thereof, or a salt of such an ester, amide or carbamate,

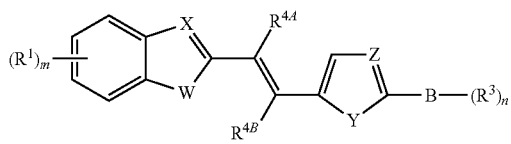

wherein:
W is S, O or Se;
X is N or N$^+$—R$^2$;
Y is S or O;
Z is CH or N;
or Y is Se and Z is CH;
B is selected from the group consisting of:

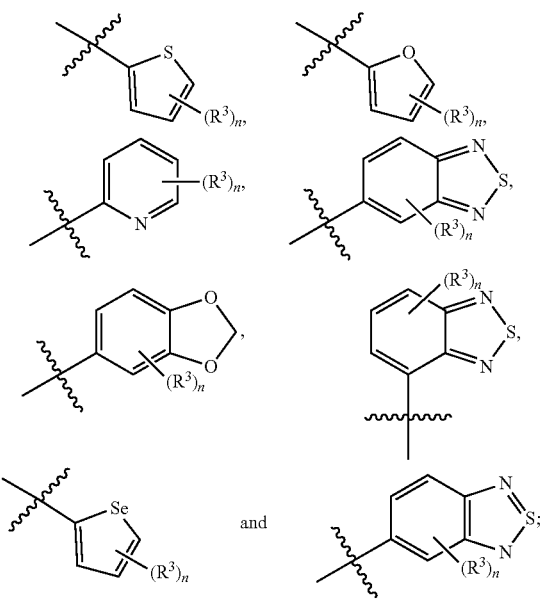

and each R$^1$ is independently selected from the group consisting of —O—C$_{1-6}$alkyl, —O-monohaloC$_{1-6}$alkyl, —O-trihaloC$_{1-6}$alkyl, C$_{1-6}$alkyl, monohaloC$_{1-6}$alkyl, dihaloC$_{1-6}$alkyl, trihaloC$_{1-6}$alkyl, OH, F, Cl, Br, I, and CN;
R$^2$ is selected from the group consisting of C$_{1-6}$alkyl, monohaloC$_{1-6}$alkyl, dihaloC$_{1-6}$alkyl, trihaloC$_{1-6}$alkyl, and C(O)C$_{1-6}$alkyl;
each R$^3$ is independently selected from the group consisting of —O—C$_{1-6}$alkyl, —O-monohaloC$_{1-6}$alkyl, —O-trihaloC$_{1-6}$alkyl, —(CH$_2$)$_p$—O—C$_{1-6}$alkyl, —(CH$_2$)$_q$—C(O)—C$_{1-6}$alkyl, —(CH$_2$)$_r$—C(O)—O—C$_{1-6}$alkyl, —(CH$_2$)$_s$—N(R$^5$)$_2$, OH, F, Cl, Br, I, —CN, —C$_{1-6}$alkyl, monohaloC$_{1-6}$alkyl, dihaloC$_{1-6}$alkyl, and trihaloC$_{1-6}$alkyl;
R$^{4A}$ and R$^{4B}$ are independently selected from the group consisting of H, OH, F, Cl, Br, I, C$_{1-6}$ alkyl, monohaloC$_{1-6}$alkyl, dihaloC$_{1-6}$alkyl, trihaloC$_{1-6}$alkyl, O—C$_{1-6}$ alkyl, —O-monohaloC$_{1-6}$alkyl, —O-dihaloC$_{1-6}$alkyl, and —O-trihaloC$_{1-6}$alkyl;

each R$^5$ is independently selected from the group consisting of H and C$_{1-6}$alkyl;
m is 0, 1, 2 or 3; n is 0, 1, 2 or 3;
p is 1, 2 or 3; q is 0, 1, or 2; r is 0, 1, or 2; and s is 0, 1, 2 or 3.

12. A method of treatment or monitoring the progression of a tauopathy in a subject, wherein the method comprises administering to a subject in need thereof a compound of formula (I) or a pharmaceutically acceptable salt, ester, amide or carbamate thereof, or a salt of such an ester, amide or carbamate,

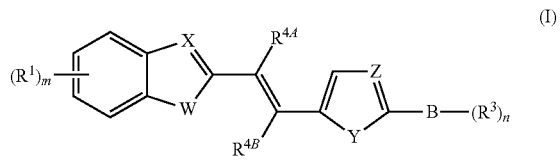

wherein
W is S, O or Se;
X is N or N$^+$—R$^2$;
Y is S or O;
Z is CH or N;
or Y is Se and Z is CH;
B is selected from the group consisting of:

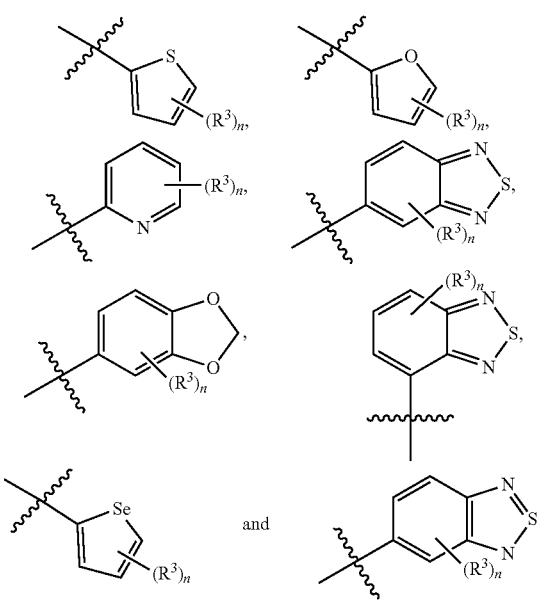

and each R$^1$ is independently selected from the group consisting of —O—C$_{1-6}$alkyl, —O-monohaloC$_{1-6}$alkyl, —O-trihaloC$_{1-6}$alkyl, C$_{1-6}$alkyl, monohaloC$_{1-6}$ alkyl, dihaloC$_{1-6}$alkyl, trihaloC$_{1-6}$alkyl, OH, F, Cl, Br, I, and CN;
R$^2$ is selected from the group consisting of C$_{1-6}$alkyl, monohaloC$_{1-6}$alkyl, dihaloC$_{1-6}$alkyl, trihaloC$_{1-6}$alkyl, and C(O)C$_{1-6}$alkyl;
each R$^3$ is independently selected from the group consisting of —O—C$_{1-6}$alkyl, —O-monohaloC$_{1-6}$alkyl, —O-trihaloC$_{1-6}$alkyl, —(CH$_2$)$_p$—O—C$_{1-6}$alkyl, —(CH$_2$)$_q$—C(O)—C$_{1-6}$alkyl, —(CH$_2$)$_r$—C(O)—O—C$_{1-6}$alkyl, —(CH$_2$)$_s$—N(R$^5$)$_2$, OH, F, Cl, Br, I, —CN, —$C_{1-6}$alkyl, monohalo$C_{1-6}$alkyl, dihalo$C_{1-6}$alkyl, and trihalo$C_{1-6}$alkyl;

$R^{4A}$ and $R^{4B}$ are independently selected from the group consisting of H, OH, F, Cl, Br, I, $C_{1-6}$ alkyl, monohalo$C_{1-6}$alkyl, dihalo$C_{1-6}$alkyl, trihalo$C_{1-6}$alkyl, O—$C_{1-6}$ alkyl, —O-monohalo$C_{1-6}$alkyl, —O-dihalo$C_{1-6}$alkyl, and —O-trihalo$C_{1-6}$alkyl;

each $R^5$ is independently selected from the group consisting of H and $C_{1-6}$alkyl;

m is 0, 1, 2 or 3; n is 0, 1, 2 or 3; and p is 1, 2 or 3; q is 0, 1, or 2; r is 0, 1, or 2; and s is 0, 1, 2 or 3;

wherein the tauopathy is selected from the group consisting of: Alzheimer's disease, corticobasal degeneration, Pick's disease, progressive supranuclear palsy, Parkinson's disease, argyrophilic grain disease, frontotemporal dementia and Parkinsonism linked to chromosome 17, Guadeloupean parkinsonism, globular glial tauopathies, ageing-related tau astrogliopathy, Parkinsonism-dementia complex of Guam, myotonic dystrophy, Down's syndrome, British dementia, familial Danish dementia, Lewy body disorders, and Prion disease.

\* \* \* \* \*